United States Patent
Gotoh et al.

(10) Patent No.: US 10,278,641 B2
(45) Date of Patent: May 7, 2019

(54) ACTIVITY METER, ACTIVITY AMOUNT MEASUREMENT DEVICE, PORTABLE TERMINAL, INFORMATION SHARING ASSISTANCE DEVICE, INFORMATION SHARING SYSTEM, ACTIVITY ASSISTANCE DEVICE, AND ACTIVITY ASSISTANCE SYSTEM

(71) Applicant: Sharp Kabushiki Kaisha, Sakai, Osaka (JP)

(72) Inventors: Wataru Gotoh, Sakai (JP); Yutaka Otsubo, Sakai (JP); Masahiro Yamauchi, Sakai (JP); Kaoru Hieda, Sakai (JP); Shigeo Akamatsu, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 0 days.

(21) Appl. No.: 15/968,882

(22) Filed: May 2, 2018

(65) Prior Publication Data

US 2018/0249949 A1    Sep. 6, 2018

Related U.S. Application Data

(62) Division of application No. 14/917,628, filed as application No. PCT/JP2014/074735 on Sep. 18, 2014, now Pat. No. 9,999,389.

(30) Foreign Application Priority Data

Sep. 20, 2013 (JP) ................................. 2013-196034
Sep. 20, 2013 (JP) ................................. 2013-196035

(Continued)

(51) Int. Cl.
*A61B 5/00* (2006.01)
*A61B 5/11* (2006.01)
(Continued)

(52) U.S. Cl.
CPC ............ *A61B 5/486* (2013.01); *A61B 5/0022* (2013.01); *A61B 5/1118* (2013.01);
(Continued)

(58) Field of Classification Search
CPC ..... A61B 5/681; A61B 5/0002; A61B 5/0022; A61B 5/1118; A61B 5/4812
See application file for complete search history.

(56) References Cited

U.S. PATENT DOCUMENTS 4,797,864 A * 1/1989 Stano ..................... G04F 10/00
368/107
2012/0290109 A1* 11/2012 Engelberg ........... G06F 19/3481
700/91

OTHER PUBLICATIONS

Gotoh et al., "Activity Meter, Activity Amount Measurement Device, Portable Terminal, Information Sharing Assistance Device, Information Sharing System, Activity Assistance Device, and Activity Assistance System", U.S. Appl. No. 14/917,628, filed Jun. 27, 2016.

* cited by examiner

*Primary Examiner* — Omeed Alizada
(74) *Attorney, Agent, or Firm* — Keating & Bennett, LLP

(57) ABSTRACT

An activity meter (100) includes (i) a sleep level judging section (112) for repeatedly detecting a sleep level of a user and (ii) a notifying section (113) for automatically notifying the user of specific information only during a period during which a most recent sleep level is less than a predetermined level.

3 Claims, 29 Drawing Sheets

(30) Foreign Application Priority Data

Sep. 25, 2013 (JP) .................................. 2013-198790
Sep. 26, 2013 (JP) .................................. 2013-200446

(51) Int. Cl.
*G08B 5/22* (2006.01)
*G06F 19/00* (2018.01)
*G16H 20/30* (2018.01)
*G16H 20/40* (2018.01)

(52) U.S. Cl.
CPC .......... *A61B 5/4812* (2013.01); *A61B 5/4815* (2013.01); *A61B 5/681* (2013.01); *G06F 19/3481* (2013.01); *G08B 5/225* (2013.01); *G16H 20/30* (2018.01); *G16H 20/40* (2018.01); *A61B 5/0002* (2013.01); *A61B 2560/0242* (2013.01)

FIG. 11
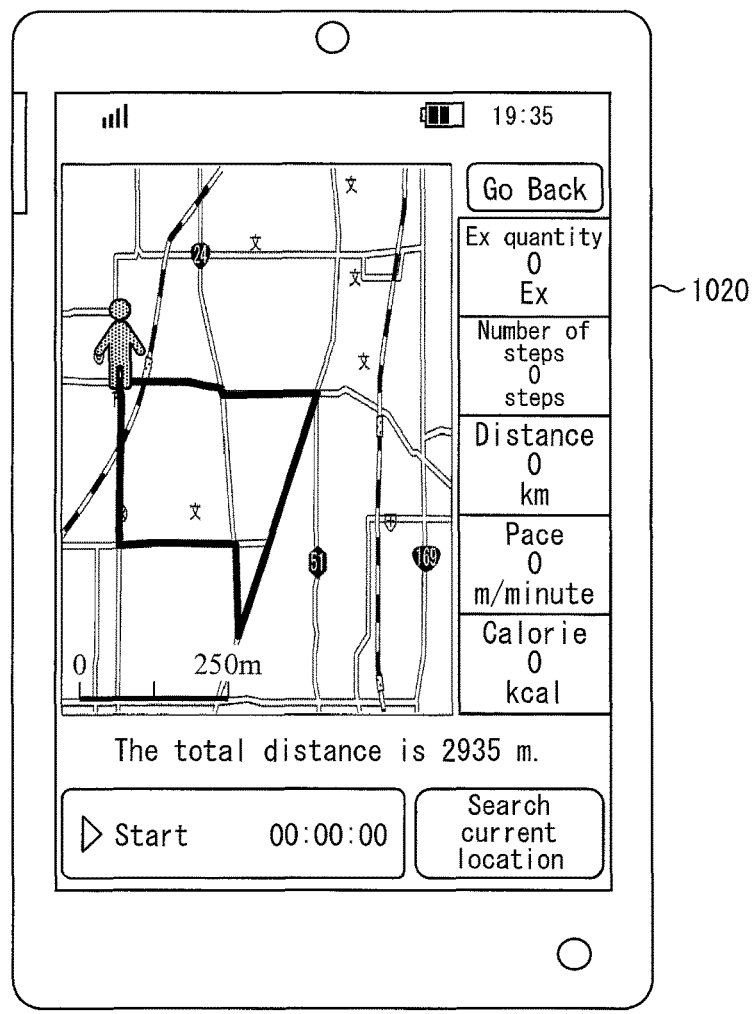
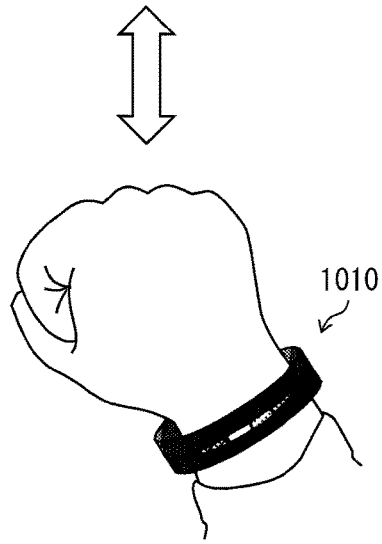

FIG. 24

| |
|---|
| {"timestamp":"2013-05-09T07:38:40+0900","latitude":"35.618634","longitude":"140.066995","altitude":"9.000000","accuracy":"10.000000"}, |
| {"timestamp":"2013-05-09T07:38:41+0900","latitude":"35.618634","longitude":"140.066995","altitude":"9.000000","accuracy":"10.000000"}, |
| {"timestamp":"2013-05-09T07:38:42+0900","latitude":"35.618634","longitude":"140.066995","altitude":"9.000000","accuracy":"10.000000"}, |
| {"timestamp":"2013-05-09T07:38:43+0900","latitude":"35.618585","longitude":"140.067009","altitude":"9.000000","accuracy":"10.000000"}, |
| {"timestamp":"2013-05-09T07:38:44+0900","latitude":"35.618585","longitude":"140.067009","altitude":"9.000000","accuracy":"10.000000"}, |
| {"timestamp":"2013-05-09T07:38:45+0900","latitude":"35.618585","longitude":"140.067009","altitude":"9.000000","accuracy":"10.000000"}, |
| {"timestamp":"2013-05-09T07:38:46+0900","latitude":"35.618585","longitude":"140.067009","altitude":"9.000000","accuracy":"10.000000"}, |
| {"timestamp":"2013-05-09T07:38:47+0900","latitude":"35.618585","longitude":"140.067009","altitude":"9.000000","accuracy":"10.000000"}, |
| {"timestamp":"2013-05-09T07:38:48+0900","latitude":"35.618585","longitude":"140.067009","altitude":"9.000000","accuracy":"10.000000"}, |
| {"timestamp":"2013-05-09T07:38:49+0900","latitude":"35.618585","longitude":"140.067009","altitude":"9.000000","accuracy":"5.000000"}, |
| {"timestamp":"2013-05-09T07:38:50+0900","latitude":"35.618585","longitude":"140.067009","altitude":"9.000000","accuracy":"5.000000"}, |
| {"timestamp":"2013-05-09T07:38:51+0900","latitude":"35.618585","longitude":"140.067009","altitude":"9.000000","accuracy":"5.000000"}, |
| {"timestamp":"2013-05-09T07:38:52+0900","latitude":"35.618585","longitude":"140.067009","altitude":"9.000000","accuracy":"5.000000"}, |
| {"timestamp":"2013-05-09T07:38:53+0900","latitude":"35.618585","longitude":"140.067009","altitude":"9.000000","accuracy":"5.000000"}, |
| {"timestamp":"2013-05-09T07:38:54+0900","latitude":"35.618585","longitude":"140.067009","altitude":"9.000000","accuracy":"5.000000"}, |
| {"timestamp":"2013-05-09T07:38:55+0900","latitude":"35.618585","longitude":"140.067009","altitude":"9.000000","accuracy":"5.000000"}, |
| {"timestamp":"2013-05-09T07:38:56+0900","latitude":"35.618585","longitude":"140.067009","altitude":"9.000000","accuracy":"5.000000"}, |
| {"timestamp":"2013-05-09T07:38:57+0900","latitude":"35.618585","longitude":"140.067009","altitude":"9.000000","accuracy":"5.000000"}, |
| {"timestamp":"2013-05-09T07:38:58+0900","latitude":"35.618585","longitude":"140.067009","altitude":"9.000000","accuracy":"5.000000"}, |
| {"timestamp":"2013-05-09T07:38:59+0900","latitude":"35.618585","longitude":"140.067009","altitude":"9.000000","accuracy":"5.000000"}, |
| {"timestamp":"2013-05-09T07:39:00+0900","latitude":"35.618585","longitude":"140.067009","altitude":"9.000000","accuracy":"5.000000"}, |
| {"timestamp":"2013-05-09T07:39:01+0900","latitude":"35.618585","longitude":"140.067009","altitude":"9.000000","accuracy":"5.000000"}, |

| USER INFORMATION | HEIGHT | WEIGHT | AGE | GENDER | STRIDE |
|---|---|---|---|---|---|
| ROUTE INFORMATION | START POINT | DESTINATION | ROUTE CONDITION | | |
| ENVIRONMENT INFORMATION | WEATHER | AIR TEMPERATURE | HUMIDITY | | |

(b)

| | ACTIVITY AMOUNT INFORMATION | | | | ACTIVITY AMOUNT AUXILIARY INFORMATION | | | | |
|---|---|---|---|---|---|---|---|---|---|
| TIME INFORMATION | NUMBER OF STEPS | EXERCISE AMOUNT | Ex QUANTITY | CALORIE | LATITUDE | LONGITUDE | ALTITUDE | ACCURACY |
| t1 | a1 | b1 | c1 | d1 | e1 | f1 | g1 | h1 |
| t2 | a2 | b2 | c2 | d2 | e2 | f2 | g2 | h2 |
| t(n-1) | a(n-1) | b(n-1) | c(n-1) | d(n-1) | e(n-1) | f(n-1) | g(n-1) | h(n-1) |
| tn | an | bn | cn | dn | en | fn | gn | hn |

ACTIVITY METER, ACTIVITY AMOUNT
MEASUREMENT DEVICE, PORTABLE
TERMINAL, INFORMATION SHARING
ASSISTANCE DEVICE, INFORMATION
SHARING SYSTEM, ACTIVITY ASSISTANCE
DEVICE, AND ACTIVITY ASSISTANCE
SYSTEM

TECHNICAL FIELD

The present invention mainly relates to (i) an activity meter and (ii) a mobile device which serves as an activity meter.

The present invention relates to an activity amount measuring device which (i) measures an activity amount of a user and (ii) transmits, to a mobile device, activity amount information indicative of the activity amount. The present invention further relates to a mobile device which (i) receives activity amount information from an activity amount measuring device and (ii) presents, to a user, an activity amount indicated by the activity amount information.

The present invention further relates to an information sharing support device, an activity amount measuring device, an information sharing system, and a method of supporting sharing of information which method is to be carried out by the information sharing support device. The present invention further relates to (i) a program for controlling a computer to operate as an information sharing support device and (ii) a storage medium in which such a program is stored.

The present invention further relates to an activity support device, a mobile device, and an activity support system.

BACKGROUND ART

Due to growing health consciousness, various techniques concerning an activity meter have been developed today (see, for example, Patent Literature 1).

Examples of the activity meter encompass (i) an activity meter capable of measuring information such as a consumed calorie, the number of steps, exercise intensity (METS), and quality of sleep and (ii) an activity meter capable of controlling a PC (personal computer), a smartphone, or a given server to store daily data on the information.

An activity meter includes a device (e.g., a vibrator, a buzzer, an LCD, an LED, etc.) for notifying a user of various kinds of information. There also exists an activity meter which periodically notifies a user of information regarding an activity amount.

Such an activity meter has an advantage of improving user's awareness regarding an activity amount of the user.

There have recently been known activity meters that (i) a user wears on his/her wrist or waist and (ii) measures a daily activity amount (the number of steps, a consumed calorie, etc.) of the user.

Patent Literature 2 discloses a number-of-steps measuring device for (i) measuring (a) the number of steps in accordance with a walking event which has been detected and (b) a walking timing which is information regarding time at which the walking event occurs and (ii) wirelessly transmitting, to an external wireless communication device, the number of steps and the walking timing which have been thus measured. According to the number-of-steps measuring device disclosed in Patent Literature 2, the wireless communication device can (i) carry out walking estimation in accordance with the number of steps and the walking timing which have been received from the number-of-steps measuring device and (ii) display the number of steps thus estimated. Therefore, even in a case where the number of steps and the walking timing are less frequently transmitted from the number-of-steps measuring device to the wireless communication device, it is still possible to update a count of the number of steps so that the count is similar to what is experienced by the user.

Patent Literature 3 discloses a pedometer capable of (i) counting a plurality of pieces of data on the number of steps which plurality of pieces of data are accumulated for respective periods and (ii) starting or stopping counting any one of the plurality of pieces of data on the number of steps. According to the pedometer disclosed in Patent Literature 3, it is possible to accurately measure data on the number of steps which data is desired by a wearer of the pedometer and is among (i) data on the number of steps which data has been accumulated over a plurality of days and (ii) data on the number of steps which has been measured during a predetermined period.

Non-Patent Literature 1 discloses an activity meter which (i) has a stopwatch mode for measuring an activity amount during a specific exercise time and (ii) controls a smartphone to display the activity amount thus measured.

There has conventionally been prevalence of activity meters for measuring a user's exercise amount such as the number of steps, a consumed calorie, and a walking distance.

In recent years, due to growing health consciousness, attention has been increasingly drawn to a system which allows users to share their activities with each other.

For example, Patent Literature 4 discloses a configuration in which it is possible to display, on a display by operating a digital music player (or a mobile phone etc.), (i) exercise data which has been measured by an exercise parameter measuring device of a user and (ii) exercise data which has been measured by an exercise parameter measuring device of another user. With the configuration, Patent Literature 4 makes it possible to compare the exercise data of the user with the exercise data of the another user.

Further, there has conventionally been prevalence of activity meters for measuring a user's exercise amount such as the number of steps, a consumed calorie, and a walking distance. For example, Patent Literature 5 discloses a technique for (i) measuring data on a user's exercise (e.g., walking slowly, walking at normal speed, etc.) and (ii) calculating exercise intensity (METs), a consumed calorie, and the like.

Meanwhile, an activity meter is desired to be small in size and light in weight so that a user can easily wear the activity meter. However, an activity meter which is small in size and light in weight places limitations on functions such as a calculation capability, a memory, and a battery. This makes it difficult to present a user's exercise amount with high accuracy.

In view of this, there has recently been prevalence of mobile devices and systems which are capable of simulating a function of an activity meter by executing an application for calculating a consumed calorie based on a walking distance of a user.

For example, Patent Literature 6 discloses a system for calculating an activity amount based on, for example, user location information which has been obtained by use of GPS.

CITATION LIST

Patent Literature

[Patent Literature 1]
Japanese Patent Application Publication, Tokukai, 2013-102870 (Publication Date: May 30, 2013)
[Patent Literature 2]
Japanese Patent Application Publication, Tokukai, 2012-203452 (Publication Date: Oct. 22, 2012)
[Patent Literature 3]
International Publication No. WO2010/082667 (Publication Date: Jul. 22, 2010)
[Patent Literature 4]
Japanese Translation of PCT International Publication, Tokuhyo, 2013-503694 (Publication Date: Feb. 4, 2013)
[Patent Literature 5]
Japanese Patent Application Publication, Tokukai, 2009-28312 (Publication Date: Feb. 12, 2009)
[Patent Literature 6]
Japanese Patent Application Publication, Tokukai, 2013-126586 (Publication Date: Jun. 27, 2013)

Non-Patent Literature

[Non-Patent Literature 1]
Jawbone, "UP", [online], accessed on Aug. 14, 2013, the Internet (URL: http://jawbone.com/up)

SUMMARY OF INVENTION

Technical Problem

A user of an activity meter having a function of measuring quality of sleep is assumed to wear the activity meter even in sleep. Even a user of an activity meter having no function of measuring quality of sleep may sleep while wearing the activity meter and while on the move by public transportation.

Therefore, an activity meter having a function to periodically notify a user of a measurement result by sound or vibration has a problem (first problem) of disturbing a user in a sleep by notifying the user of the measurement result.

The present invention has been made in view of the first problem. A first object of the present invention is to provide an activity meter which (i) is equipped with a function to automatically notify a user of specific information and (ii) is unlikely to disturb the user in a deep sleep by notifying the user of the notification.

A period during which the activity amount measuring device measures an activity amount may preferably be short or long. For example, a user desires to know an activity amount in real time while walking. In such a case, therefore, the period, in which the activity amount measuring device measures the activity amount, is preferably short. Meanwhile, there is a problem that measurement of the activity amount in a short period increases electric power consumption of the activity amount measuring device. In addition, an amount of measured data also increases, and therefore poses another problem that a memory capacity for storing the measured data also needs to be increased. Therefore, in a case where a user desires to know an activity amount of the user during one of ordinary days, for example, the period during which the activity amount measuring device measures the activity amount is preferably long.

However, the technique disclosed in Patent Literature 2 allows an activity amount to be measured only in a short period.

According to the technique disclosed in Patent Literature 3 and the activity meter disclosed in Non-Patent Literature 1, it is possible to carry out measurement in a short period or a long period. However, a user needs to change, by directly operating the activity meter, a period during which the measurement is to be carried out. In recent years, there have been applications or the like for smartphones, which applications present a route for walking or jogging according to a distance and/or time that a user desires. According to the technique disclosed in Patent Literature 3 and the activity meter disclosed in Non-Patent Literature 1, in a case where such an application is used, both of a smartphone and an activity meter need to be operated. This poses a problem (second problem) of causing an operation of a user to be complicated.

The present invention has been made in view of the second problem. A second object of the present invention is to allow an activity amount measuring device, which measures an activity amount, to change, via a mobile device, a period during which an activity amount is to be measured.

According to the system disclosed in Patent Literature 4, a digital music player needs to be operated so that exercise data measured by an exercise parameter measuring device of each user is shared. This poses a problem that it becomes complicated to share the exercise data. In particular, there is a problem (third problem) that it is difficult for a user to obtain exercise data of another user while the user is carrying out exercise (e.g., while the user is running).

The present invention has been made in view of the third problem. A third object of the present invention is to provide an information sharing support device capable of allowing activity amount measuring devices to easily share activity amount information without causing a user to operate any devices.

Furthermore, there is a problem (fourth problem) that, according to a conventional technique for presenting, to a user who does not possess an activity meter, an activity amount which has been automatically calculated by use of generally defined parameters, the user cannot know an accurate activity amount of his/her own. For example, in a case where an activity amount of walking from a start point to a goal point is calculated based on (i) a distance from the start point to the goal point and (ii) a time required for the walking, a difference in altitude such as a slope or the like is not taken into account, and therefore an accurate activity amount cannot be calculated.

The present invention has been made in view of the fourth problem. A fourth object of the present invention is to provide an activity support device capable of providing, to a mobile device of a user who does not possess an activity amount measuring device, an accurate activity amount corresponding to an actual activity amount obtained in a case where a predetermined exercise has been carried out.

Solution to Problem

In order to attain the first object, an activity meter according to an aspect of the present invention is an activity meter to be worn by a user, including: a judging section for repeatedly judging a sleep level of the user; and a notifying section for automatically notifying the user of specific information only during a period during which a most recent sleep level is less than a predetermined level.

In order to attain the second object, an activity amount measuring device according to an aspect of the present invention is an activity amount measuring device for measuring an activity amount of a user and transmitting, to a mobile device, activity amount information that indicates the activity amount thus measured, the activity amount measuring device having (i) a first measuring mode in which measurement of the activity amount is carried out during a first period and (ii) a second measuring mode in which, in addition to the measurement during the first period, measurement of the activity amount is carried out during a second period which is shorter than the first period, said activity amount measuring device including: a receiving section for receiving, from the mobile device, a command that instructs a change in a measuring mode; and a measuring section for measuring the activity amount, the measuring section changing the measuring mode in accordance with the command thus received by the receiving section.

In order to attain the second object, a mobile device according to an aspect of the present invention is a mobile device for (i) receiving, from an activity amount measuring device, activity amount information which indicates an activity amount of a user and (ii) presenting, to the user, the activity amount indicated by the activity amount information thus received, the activity amount measuring device having (i) a first measuring mode in which measurement of the activity amount is carried out during a first period and (ii) a second measuring mode in which, in addition to the measurement during the first period, measurement of the activity amount is carried out during a second period which is shorter than the first period, said mobile device including: a transmitting section for transmitting, in a case where a predetermined user operation has been detected, a command to the activity amount measuring device, a command that instructs a change in a measuring mode in which the activity amount measuring device measures the activity amount, the command being transmitted to the activity amount measuring device.

In order to attain the third object, an information sharing support device according to an aspect of the present invention is an information sharing support device including: an obtaining section for obtaining, from a first mobile device, first activity amount information which indicates an activity amount measured by a first activity amount measuring device that measures an activity amount of a first user, the first mobile device communicating with the first activity amount measuring device via short-distance wireless communication; a generating section for generating a reporting instruction which (i) instructs reporting in accordance with the first activity amount information and (ii) instructs reporting by a second activity amount measuring device that measures an activity amount of a second user who is different from the first user; and a transmitting section for transmitting the reporting instruction to a second mobile device which communicates with the second activity amount measuring device via short-distance wireless communication.

In order to attain the third object, an activity amount measuring device according to an aspect of the present invention is an activity amount measuring device for measuring an activity amount of a user, including: a receiving section for obtaining activity amount information which indicates an activity amount of another user, the activity amount of the another user being measured by another activity amount measuring device other than the activity amount measuring device, the receiving section receiving the activity amount information from an information sharing support device via a mobile device which communicates with the activity amount measuring device via short-distance wireless communication; and a reporting section for reporting in accordance with the activity amount information thus obtained by the receiving section.

In order to attain the third object, an information sharing system according to an aspect of the present invention is an information sharing system, including: a first activity amount measuring device for measuring an activity amount of a first user; a second activity amount measuring device for measuring an activity amount of a second user; a first mobile device for communicating with the first activity amount measuring device via short-distance wireless communication; a second mobile device for communicating with the second activity amount measuring device via short-distance wireless communication; and an information sharing support device for communicating with the first mobile device and with the second mobile device, the information sharing support device transmitting a reporting instruction to the second activity amount measuring device via the second mobile device, the reporting instruction being an instruction which (i) instructs reporting in accordance with activity amount information indicative of the activity amount of the first user, the activity amount information having been transmitted from the first activity amount measuring device via the first mobile device and (ii) instructs reporting by the second activity amount measuring device, and the second activity amount measuring device reporting in accordance with the reporting instruction.

In order to attain the fourth object, an activity support device according to an aspect of the present invention is an activity support device including: a providing section for providing, in a case where a target user carries out predetermined exercise, a mobile device of the target user with target user activity amount information indicative of a target user activity amount corresponding to the predetermined exercise; and an obtaining section for obtaining another user activity amount information indicative of an another user activity amount of the predetermined exercise carried out by another user, the obtaining section obtaining the another user activity amount information from another mobile device which corresponds to an activity amount measuring device that measures the another user activity amount of the another user, the providing section providing, as the target user activity amount information, the another user activity amount information which has been obtained by the obtaining section.

In order to attain the fourth object, a mobile device according to an aspect of the present invention is a mobile device including: a presenting section for presenting, in a case where a target user carries out predetermined exercise, a target user activity amount corresponding to the predetermined exercise; and a receiving section for receiving another user activity amount information indicative of another user activity amount of the predetermined exercise carried out by another user, the receiving section receiving the another user activity amount information from another mobile device via an activity support device, which another mobile device corresponds to an activity amount measuring device that measures the another user activity amount of the another user, the presenting section presenting, as the target user activity amount information, an activity amount indicated by the another user activity amount information which has been received by the receiving section.

In order to attain the fourth object, an activity support system according to an aspect of the present invention is an activity support system including: a mobile device for presenting, in a case where a target user carries out predetermined exercise, a target user activity amount corresponding to the predetermined exercise; another mobile device corresponding to an activity amount measuring device that measures another user activity amount of another user; and an activity support device for communicating with the mobile device and with the another mobile device, the activity support device transmitting, to the mobile device, another user activity amount information which has been obtained from the another mobile device and which indicates another user activity amount of the predetermined exercise carried out by the another user, and the mobile device presenting, as the target user activity amount information, the another user activity amount indicated by the another user activity amount information transmitted from the activity support device.

Advantageous Effects of Invention

An activity meter according to an aspect of the present invention, which is an activity meter equipped with a function to automatically notify a user of specific information, has such an advantage as being unlikely to disturb the user in a deep sleep by notifying the user of the specific information. Therefore, the first object can be attained.

According to an aspect of the present invention, an activity amount measuring device can change, via a mobile device, a period during which an activity amount is to be measured. This attains the second object.

According to an aspect of the present invention, the information sharing support device is capable allowing the first and second activity amount measuring devices to easily share the first activity amount information without causing a user to operate any devices. This attains the third object.

According to an aspect of the present invention, the activity support device is capable of providing, to the mobile device of the user who does not possess an activity amount measuring device, an accurate activity amount corresponding to an actual activity amount obtained in a case where the predetermined exercise has been carried out. This attains the fourth object.

BRIEF DESCRIPTION OF DRAWINGS

FIG. 11 is a view illustrating an appearance of the activity amount measuring system according to Embodiment 4.

Figure 16:
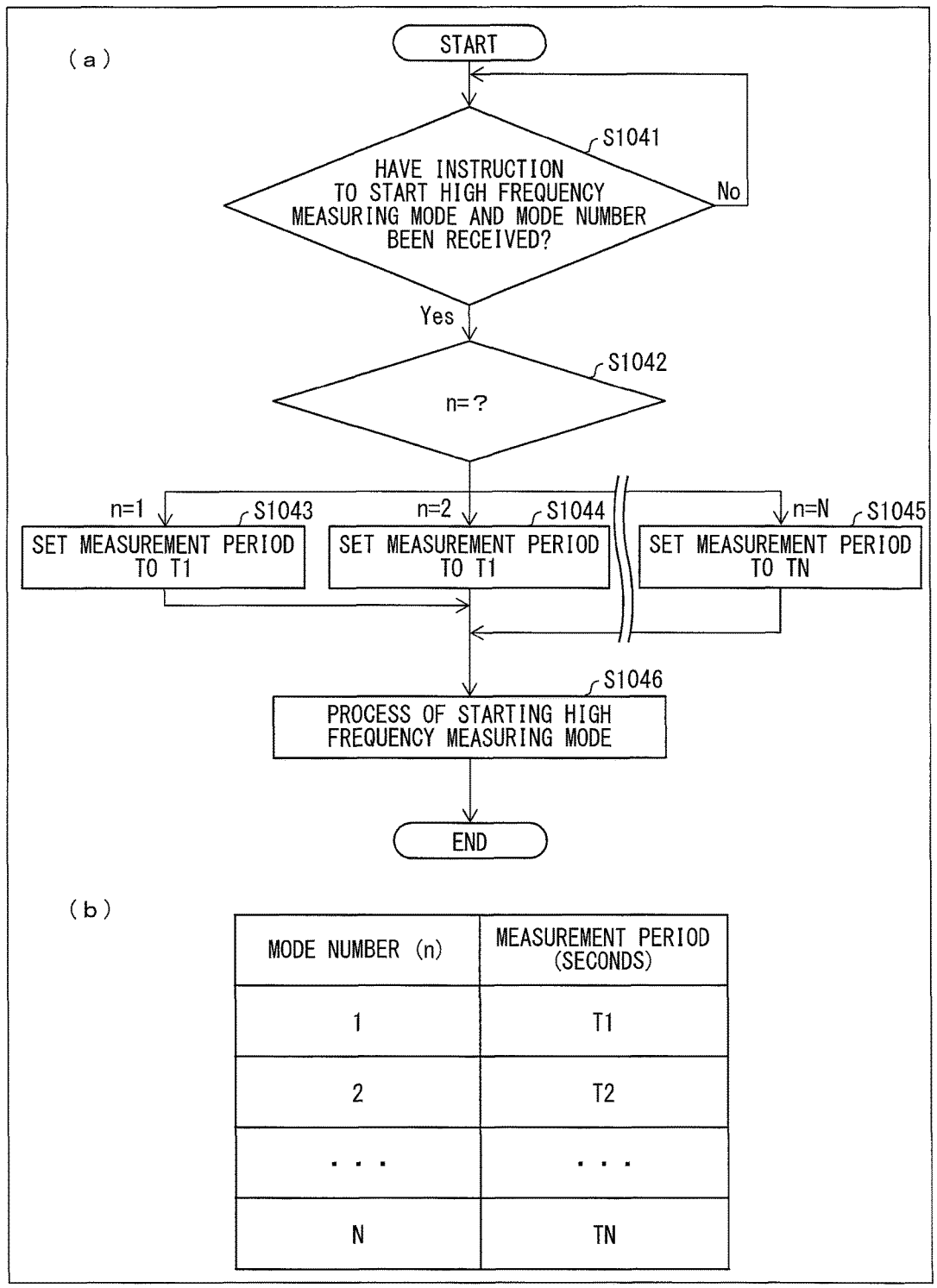

(a) of FIG. 16 is a flow chart illustrating a flow of a frequency measuring mode process carried out at a start of a high frequency measuring mode, which process is carried out by an activity meter included in an activity amount measuring system according to Embodiment 8. (b) of FIG. 16 illustrates a table which shows relationships between mode numbers and corresponding measurement periods.

Figure 17:
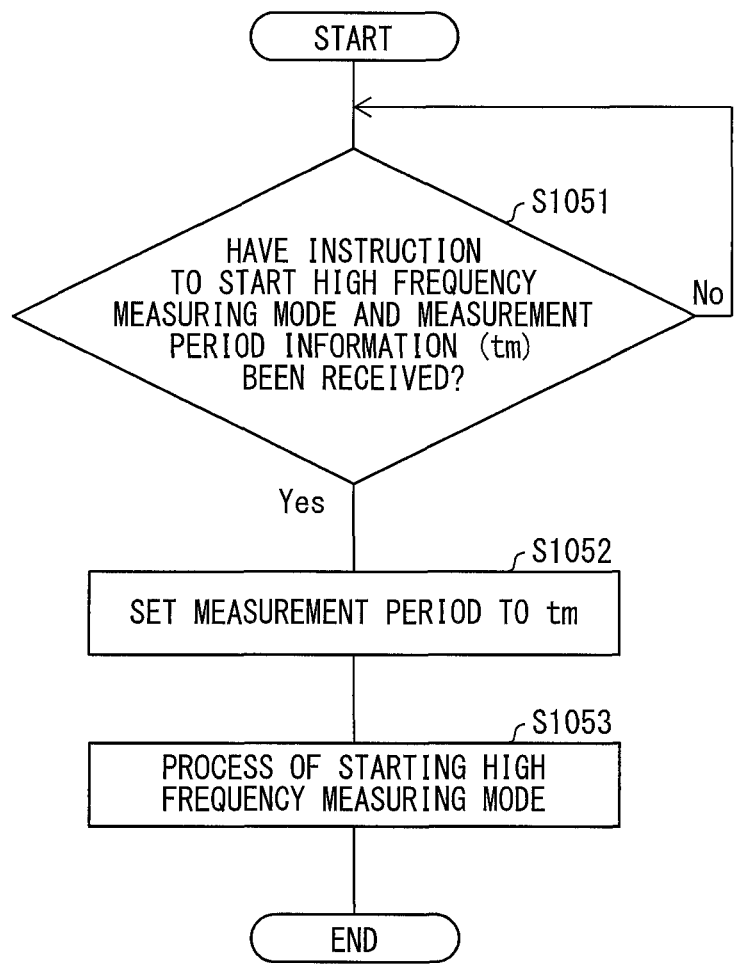

FIG. 17 is a flow chart illustrating a flow of a frequency measuring mode process carried out at a start of a high frequency measuring mode, which process is carried out by an activity meter included in an activity amount measuring system according to Embodiment 9.

Figure 18:
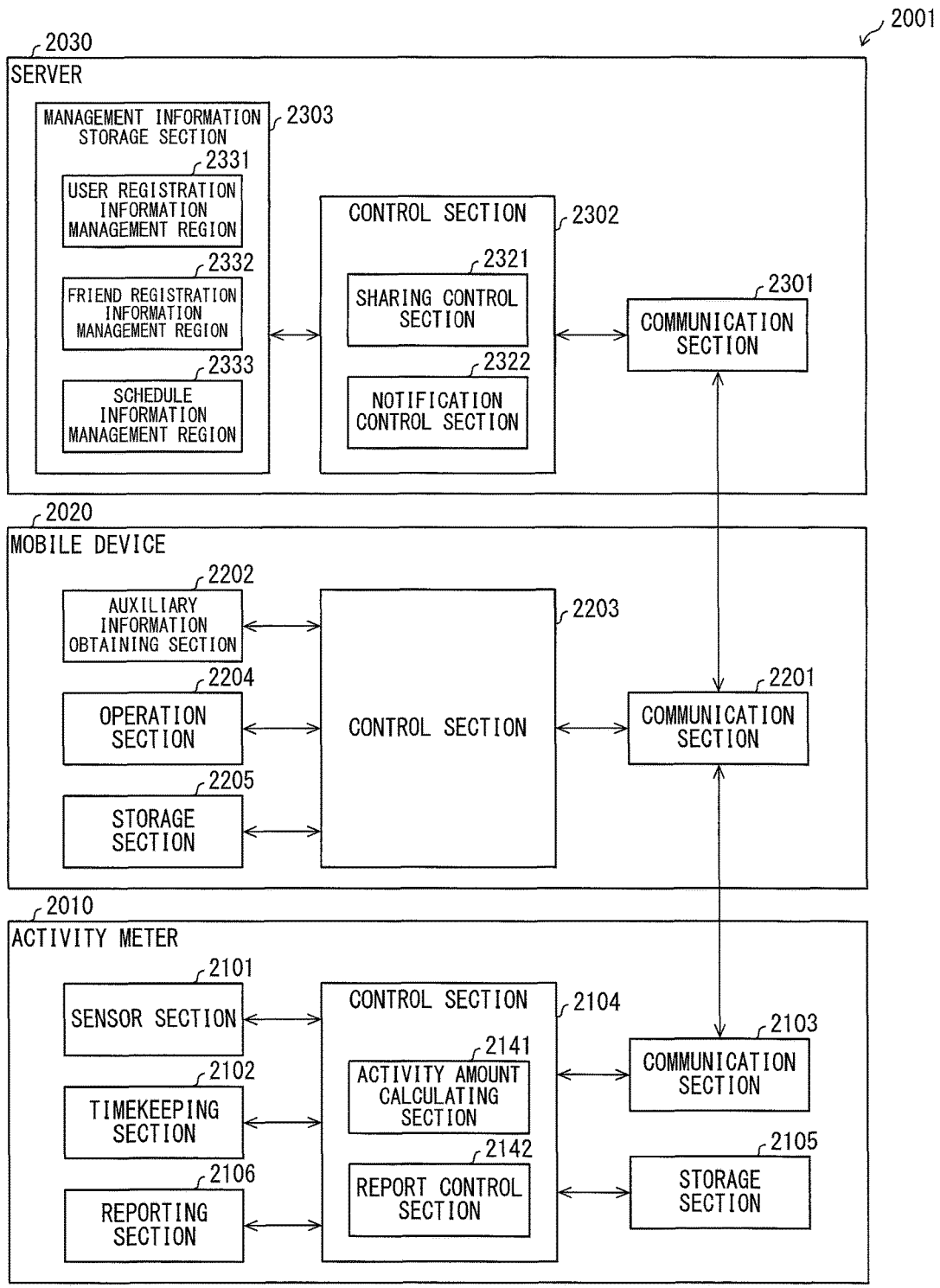

FIG. 18 is a block diagram illustrating configurations an activity meter, a mobile device, and a server which are included in an information sharing system according to Embodiment 10.

Figure 19:
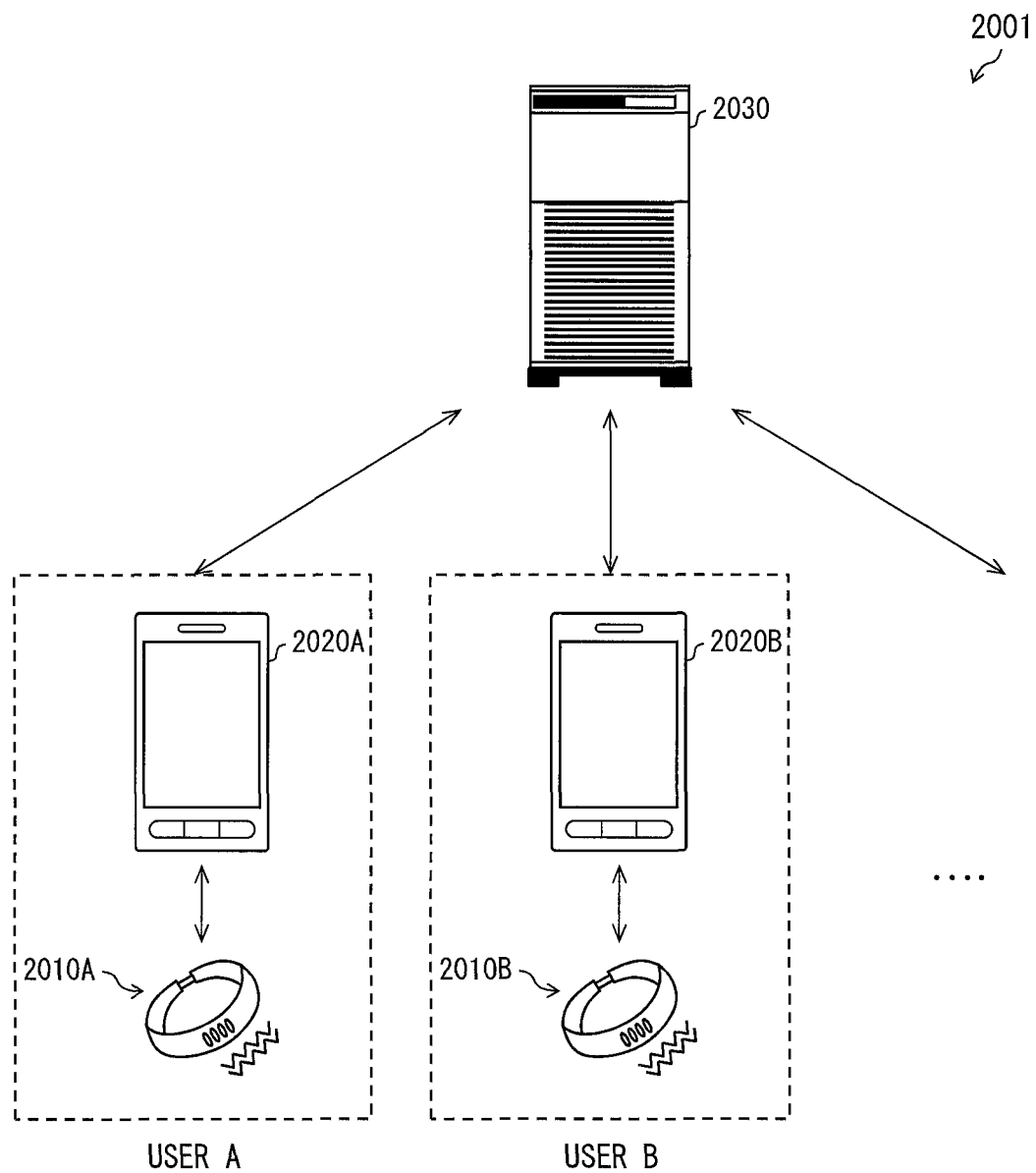

FIG. 19 is a view illustrating an appearance of an information sharing system according to an aspect of the present invention.

Figure 20:
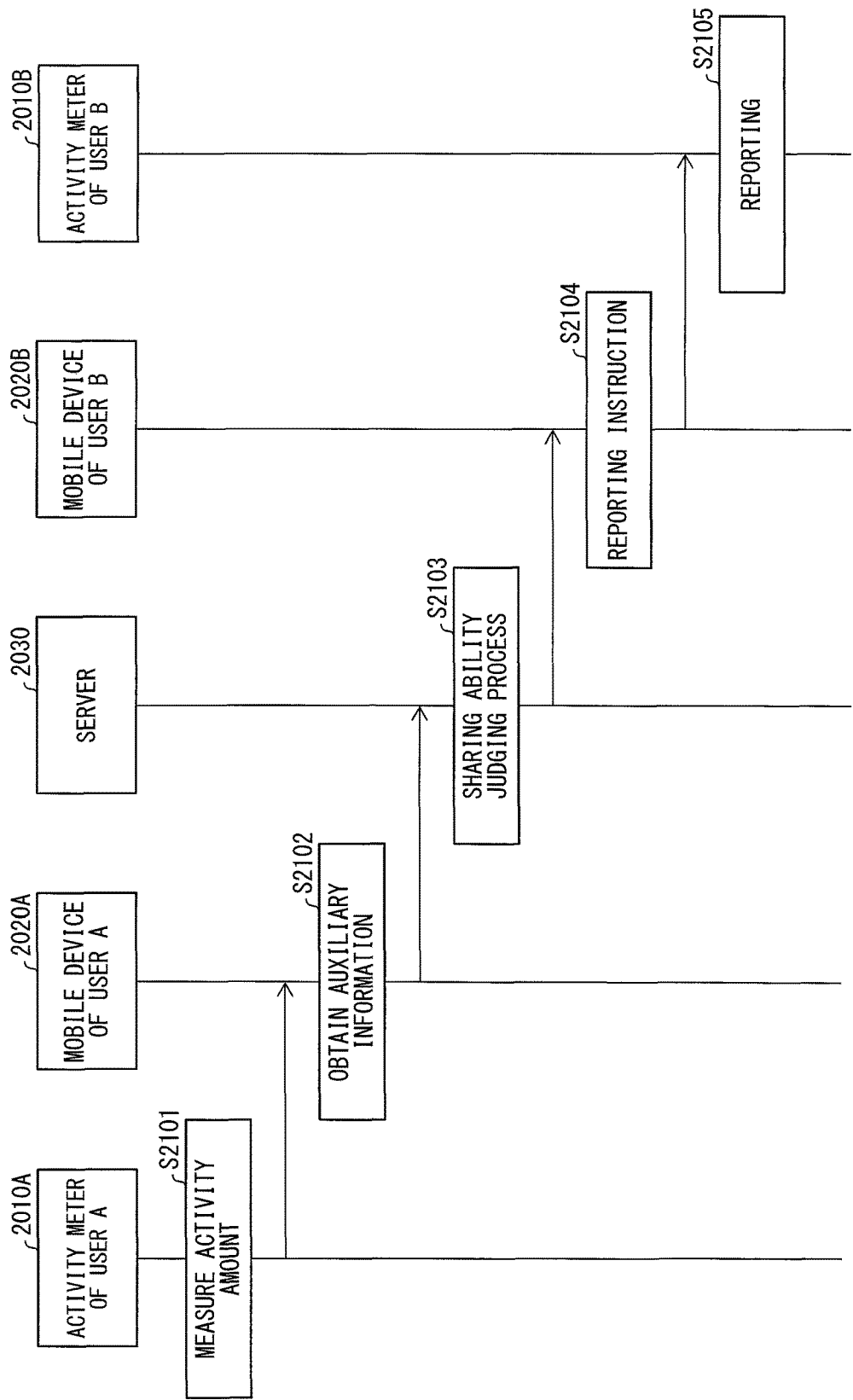

FIG. 20 is a sequence diagram illustrating an exerciser information sharing/reporting process carried out by an information sharing system according to an aspect of the present invention.

Figure 21:
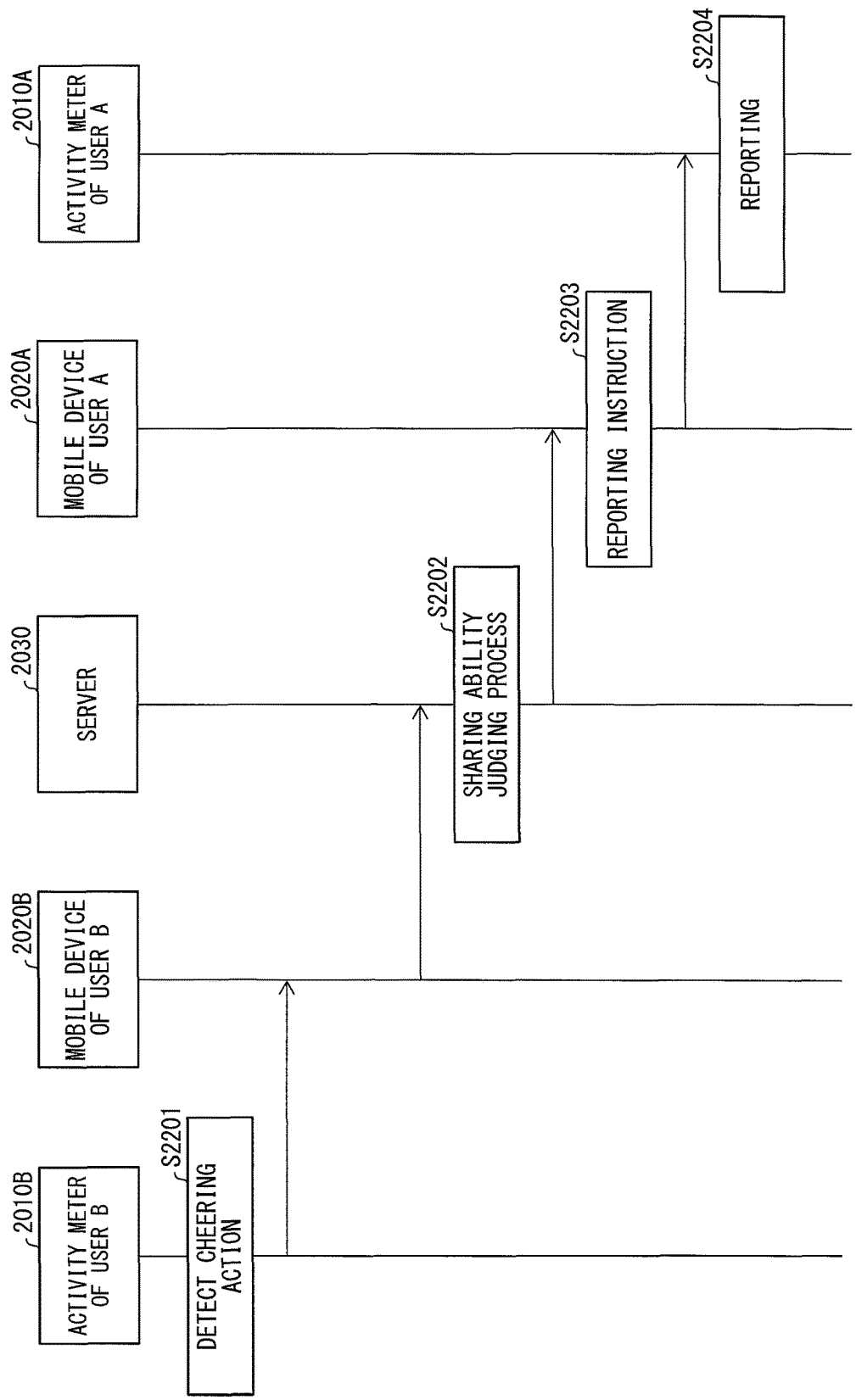

FIG. 21 is a sequence diagram illustrating an exerciser information sharing/reporting process carried out by an information sharing system according to an aspect of the present invention.

Figure 22:
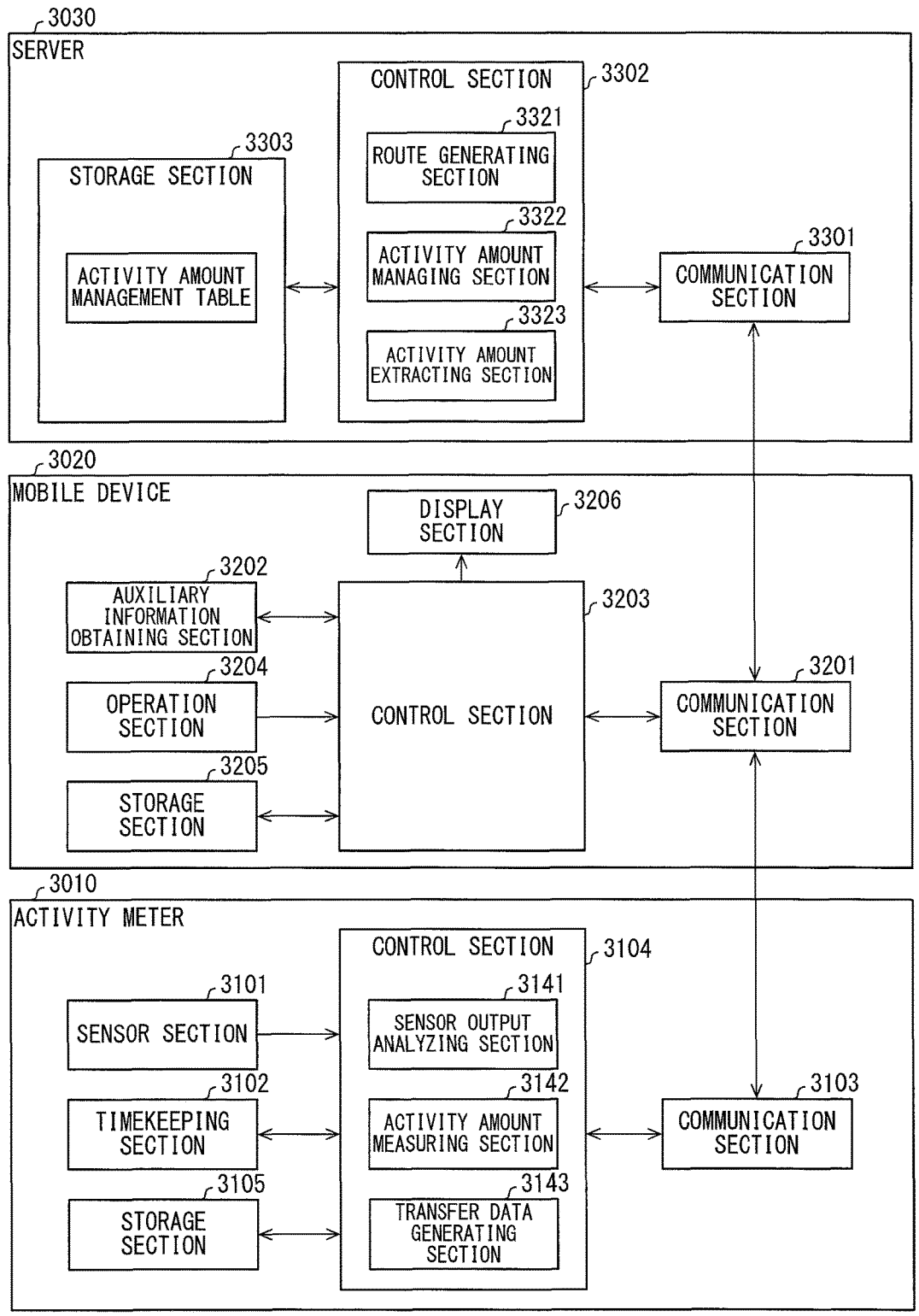

FIG. 22 is a block diagram illustrating configurations an activity meter, a mobile device, and a server which are included in an activity support system according to an aspect of the present invention.

Figure 23:
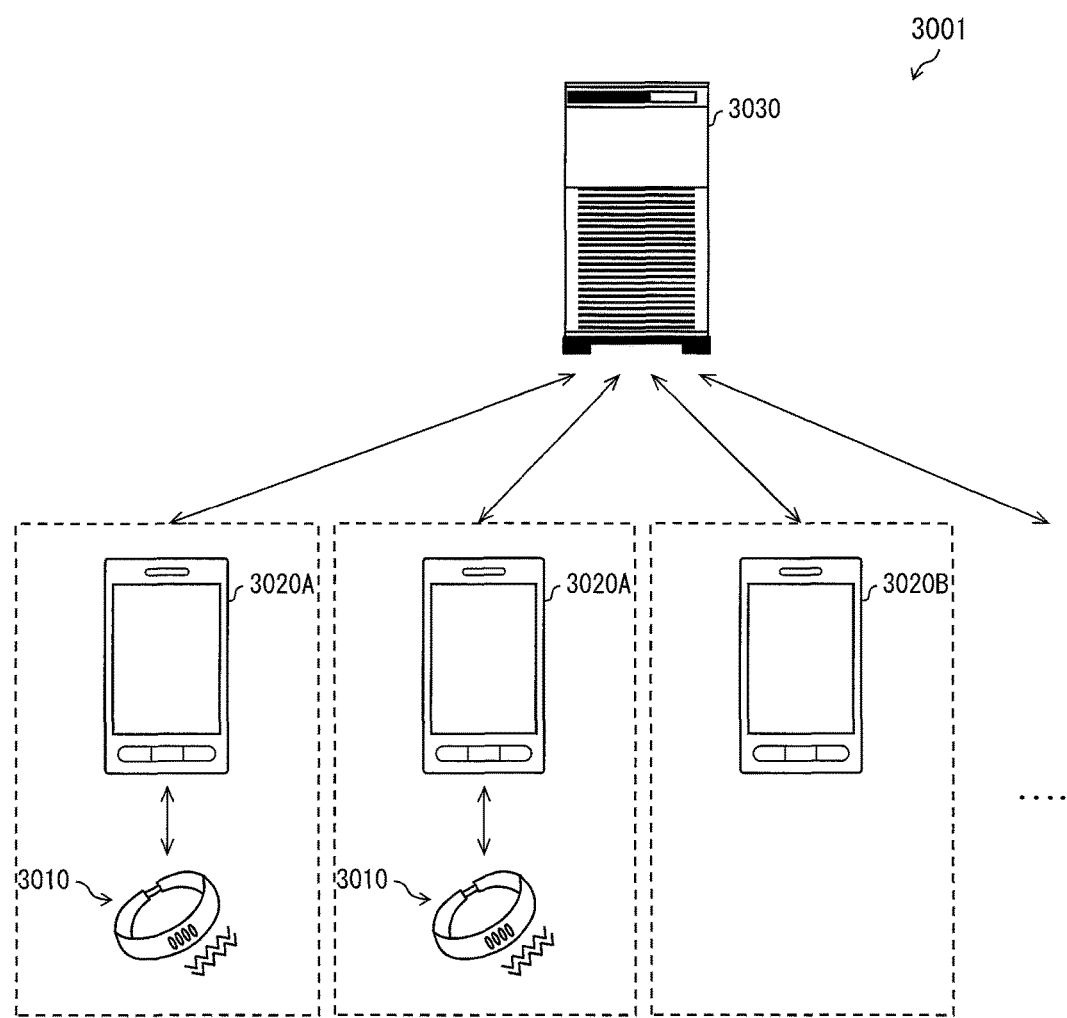

FIG. 23 is a view illustrating an appearance of an activity support system according to an aspect of the present invention.

FIG. 24 is a view illustrating data that is indicated by activity amount auxiliary information transmitted from a mobile device to a server, according to an aspect of the present invention.

Figure 25:
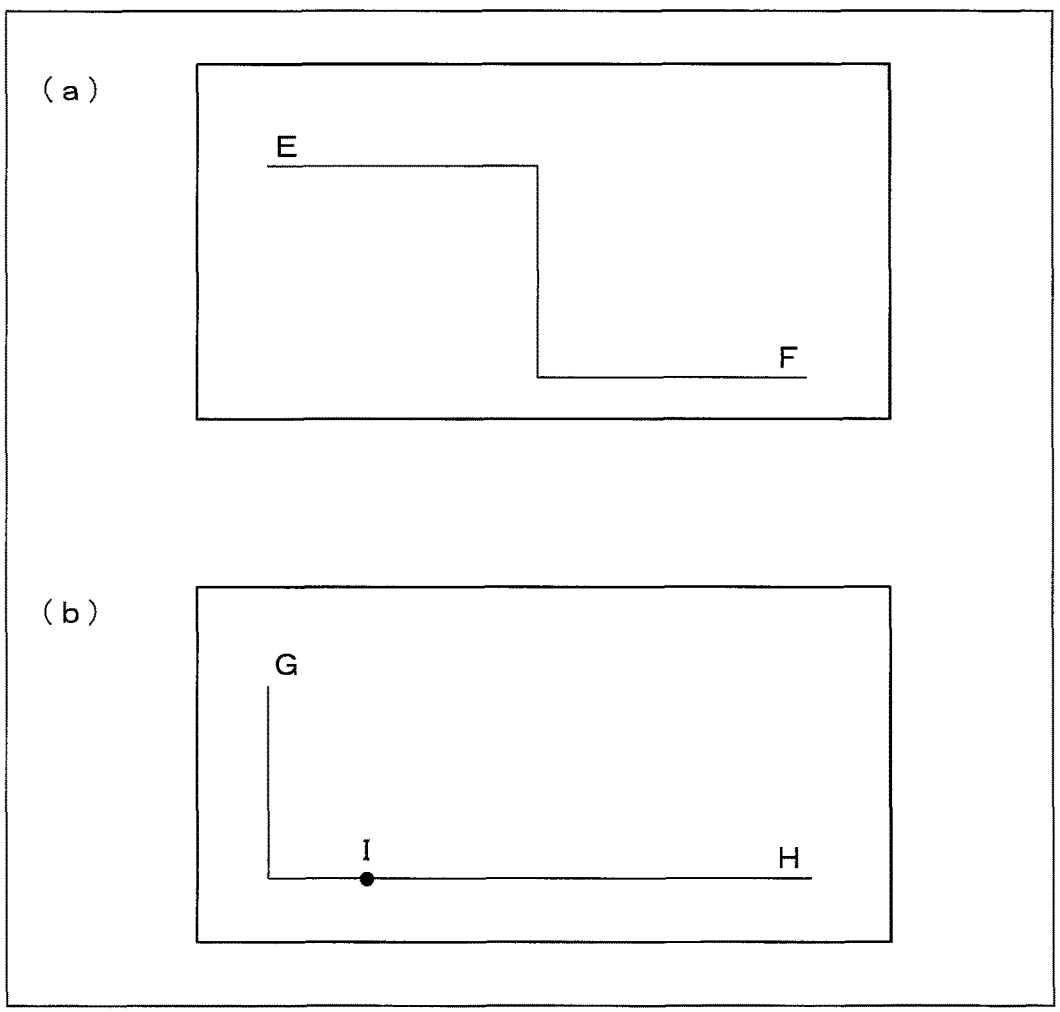

FIG. 25 is a view schematically illustrating a map which includes a walking route and which is displayed on a section of a mobile device according to an aspect of the present invention. (a) of FIG. 25 illustrates a map in which a start point is a point E, a destination is a point F, and a route condition is set so that a distance becomes 1 km. (b) of FIG.

25 illustrates a map in which a start point is a point G, a destination is a point H, and a route condition is set so that the route passes through a point I.

FIG. 26 is a view illustrating the activity amount management table according to Embodiment 13. (a) of FIG. 26 illustrates a fixed data table in the activity amount management table, and (b) of FIG. 26 illustrates a variable data table in the activity amount management table.

Figure 27:
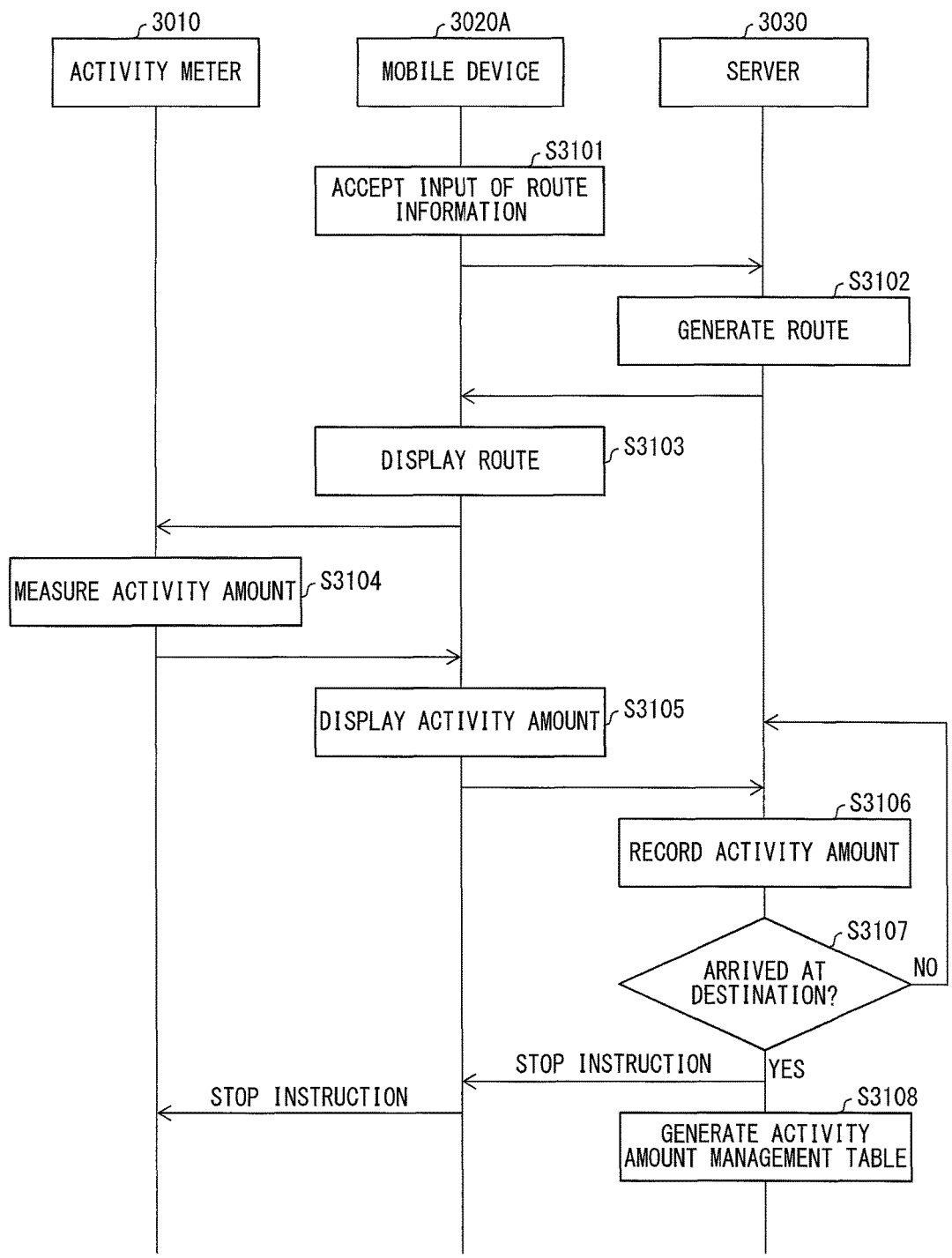

FIG. 27 is a sequence diagram illustrating an activity amount presenting process which is carried out in an activity support system with respect to a user who uses an activity meter according to an aspect of the present invention.

Figure 28:
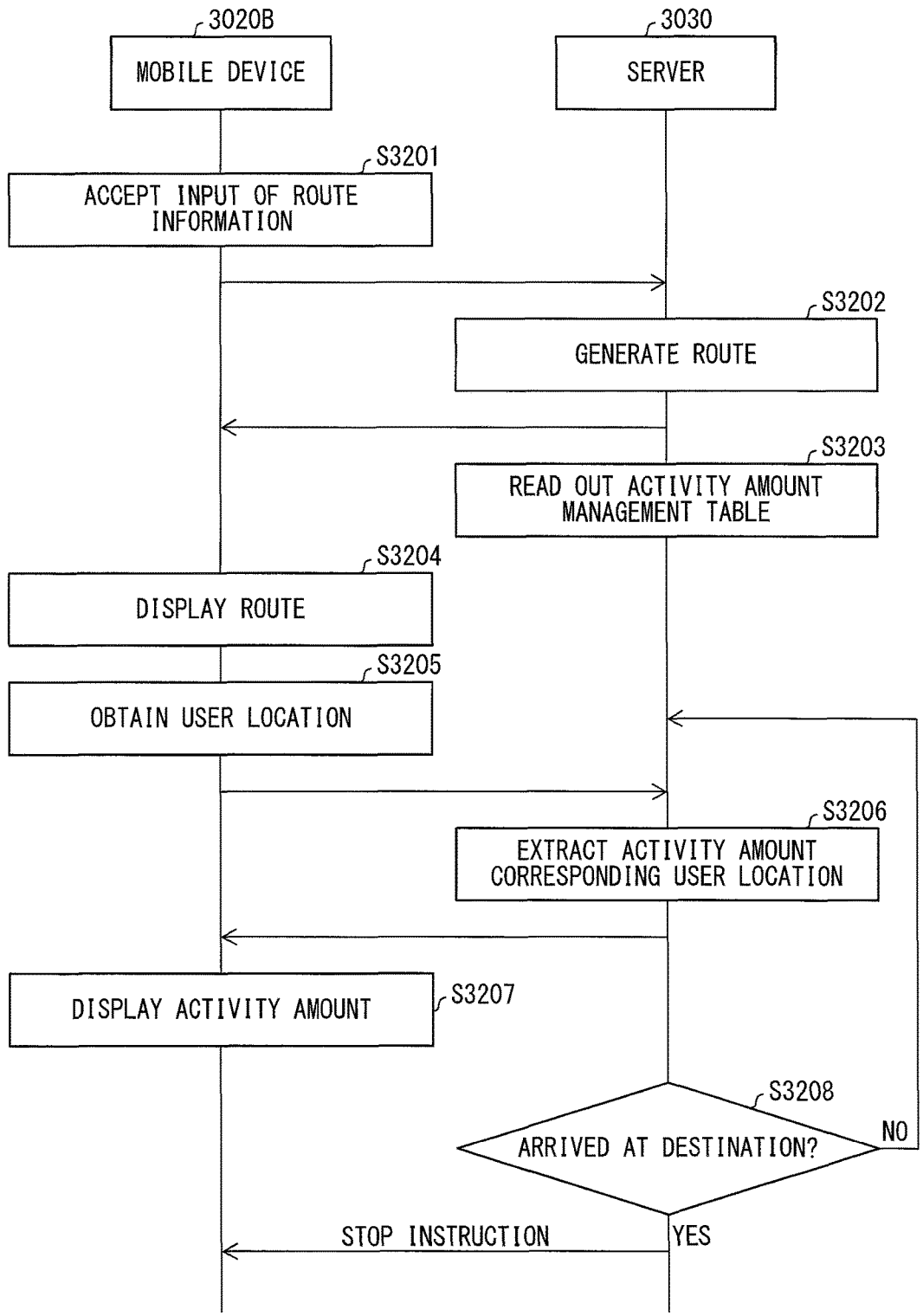

FIG. 28 is a sequence diagram illustrating an activity amount presenting process which is carried out in the activity support system with respect to a user who does not use the activity meter according to the aspect of the present invention.

Figure 29:
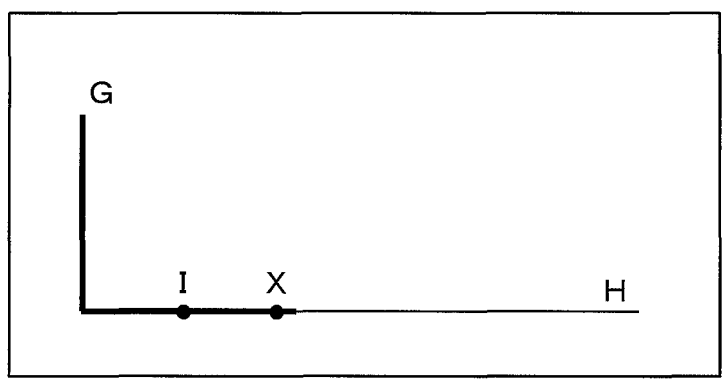

FIG. 29 is a view schematically illustrating a map which includes a walking route and which is displayed on a section of a mobile device according to an aspect of the present invention.

DESCRIPTION OF EMBODIMENTS

Embodiment 1

The following description will discuss, with reference to FIGS. 1 through 4, an activity meter and a smartphone according to an embodiment of the present invention.

Figure 1:
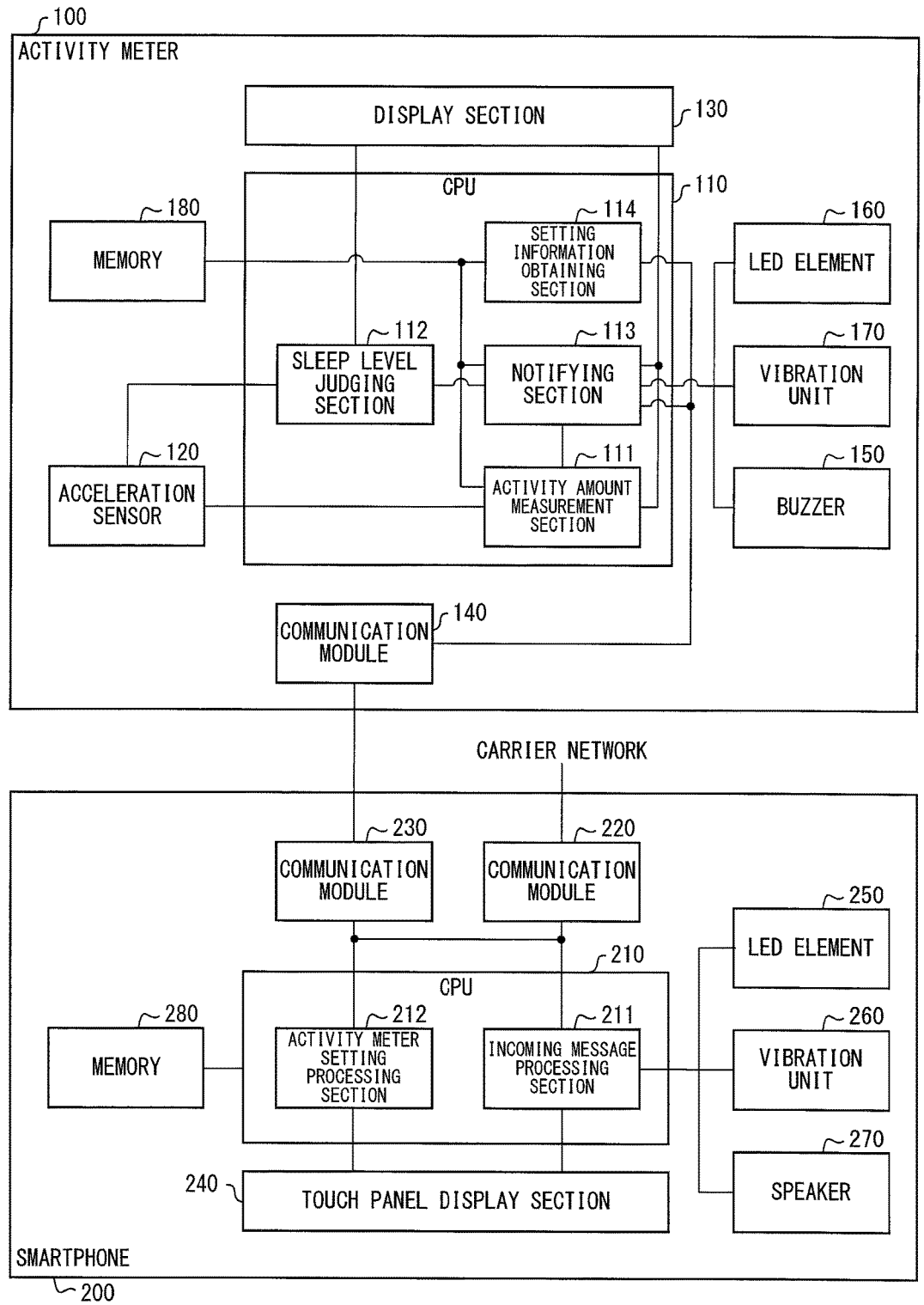
FIG. 1 is a block diagram illustrating main configurations an activity meter and a smartphone according to Embodiment 1 of the present invention.
Figure 2:
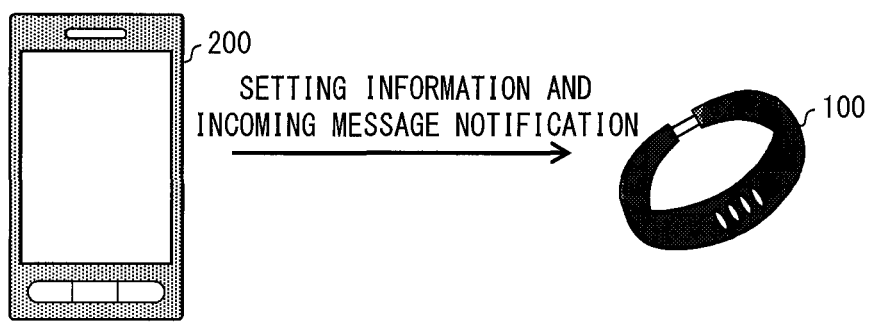
FIG. 2 is a view illustrating appearances of the activity meter and the smartphone illustrated in FIG. 1.
Figure 3:
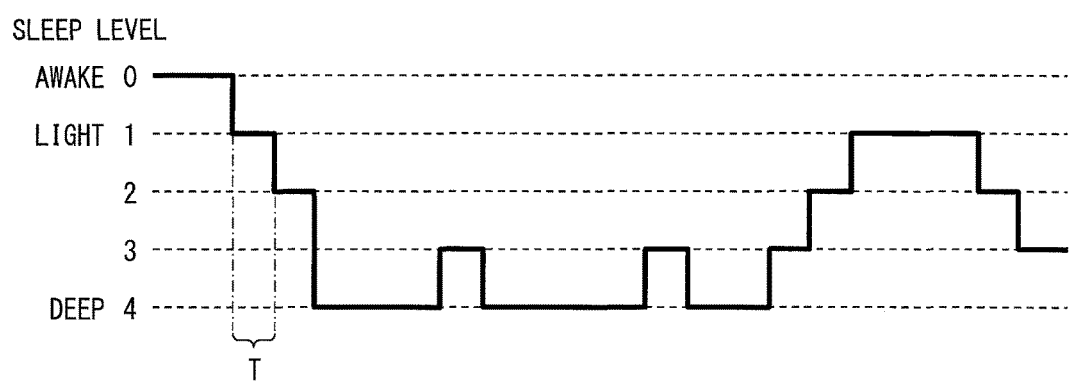
FIG. 3 is a view illustrating, in a graph format, a sleep level which is measured by the activity meter illustrated in FIG. 1.

First, the following description will discuss, with reference to FIGS. 1 through 3, configurations of the activity meter and the smartphone according to Embodiment 1.

FIG. 1 is a block diagram illustrating main configurations of the activity meter and the smartphone according to Embodiment 1. FIG. 2 is a view illustrating appearances of the activity meter and the smartphone according to Embodiment 1. FIG. 3 is a view illustrating, in a graph format, a sleep level which is measured by the activity meter according to Embodiment 1.

(Activity Meter 100)

As illustrated in FIG. 1, an activity meter 100 according to Embodiment 1 includes a CPU 110, an acceleration sensor 120, a display section 130, a communication module 140, a buzzer 150, an LED element 160, a vibration unit 170, and a memory 180.

As illustrated in FIG. 2, the activity meter 100 is a dedicated activity meter which includes a wrist band serving as a mounting fixture.

Note that the activity meter of the present invention is not limited to a dedicated activity meter, but can be a mobile device having various functions including a function of measuring an activity amount. For example, the activity meter of the present invention can be a smartphone (or a feature phone, a tablet device, a mobile PC, etc.) including the CPU 110, the acceleration sensor 120, the display section 130, the communication module 140, the buzzer 150, the LED element 160, the vibration unit 170, and the memory 180.

The activity meter 100 can further include another kind of mounting fixture (e.g., a clip, a strap, or a neck-worn object) other than the wrist band.

(CPU 110)

After a power supply of the activity meter 100 is turned on, the CPU 110 reads a program from the memory 180 so as to start serving as an activity amount measurement section 111, a sleep level judging section 112, a notifying section 113, and a setting information obtaining section 114.

(Activity Amount Measurement Section 111)

The activity amount measurement section 111 measures an activity amount according to information supplied from the acceleration sensor 120. The activity amount is a numerical value which is obtained by quantifying an intensity of an activity of a user. Examples of the activity amount encompass the number of steps, an exercise amount (METs, Metabolic equivalents), an exercise (EX) quantity, a walking distance, a walking pace, a consumed calorie, the number of steps taken while walking (the number of steps having an exercise amount of 3 METs or more), the number of steps taken while jogging (the number of steps having an exercise amount of 6 METs or more), and an activity time (a period of time during which a user does an activity causing an exercise amount of 3 METs or more.

(Sleep Level Judging Section 112)

The sleep level judging section 112 (judging section) periodically judges, during a period T of several minutes to several tens of minutes (e.g., every five minutes), a sleep level of a user during a most recent period T (e.g., a most recent five-minute period) in accordance with information supplied from the acceleration sensor 120.

Specifically, in a case where a user is awake, the sleep level judging section 112 judges that a sleep level of the user is "0". In a case where a user is asleep, the sleep level judging section 112 judges that a sleep level of the user is "1", "2", "3", or "4", depending on depth of the user's sleep.

Every time the sleep level judging section 112 judges the sleep level, the sleep level judging section 112 stores, in the memory 180, information indicative of a judgement result. This causes information regarding sleep levels of the user up to a current time to be always stored in the memory 180 (see FIG. 3).

Note that a configuration of the sleep level judging section 112 is not limited to a configuration in which a sleep level of a user is indicated in five levels. That is, the sleep level judging section 112 can be configured so that a sleep level of a user is indicated in N levels (N≥6) or so that a sleep level of a user is indicated in two, three, or four levels. For example, the sleep level judging section 112 can (i) judge that a sleep level of a user is "0" in a case where the user is awake and (ii) judge that a sleep level of a user is "1" in a case where the user is asleep.

Alternatively, the sleep level judging section 112 can judge a sleep level of a user during a most recent period T according to not only the information supplied from the acceleration sensor 120 but also information supplied from one or more other kinds of sensors and/or a signal supplied from a microphone input. Examples of the other kinds of sensors encompass a heart rate sensor, a pulse sensor, and a temperature sensor.

(Notifying Section 113)

According to setting information stored in the memory 180, the notifying section 113 (notifying section) provides, to the user, a notification at time (default drive start time (described later)) set by a user with the use of a smartphone 200, the notification being based on a measurement value of an activity amount which measurement value has been measured by the activity amount measurement section 111 until a current time. Specifically, the notifying section 113 (i) displays, on the display section 130, content to be notified and (ii) drives the buzzer 150, the LED element 160, or the vibration unit 170.

In a case where the notifying section 113 (receiving section) receives an incoming message notification from the smartphone 200, the notifying section 113 (i) displays, on the display section 130, information which indicates that the smartphone 200 has received an incoming message and (ii) drives the buzzer 150, the LED element 160, or the vibration unit 170.

Note that in a case where a sleep level of a user during a most recent period T is a predetermined threshold TH (specifically, "1") or greater at the time set by the user, the notifying section 113 does not provide a notification. Similarly, the notifying section 113 does not provide a notification in a case where a sleep level of the user during a most recent period T is the predetermined threshold TH or greater at time at which the notifying section 113 receives the incoming message notification from the smartphone 200.

(Setting Information Obtaining Section 114)

The setting information obtaining section 114 (i) obtains, from the smartphone 200, setting information including information indicative of default drive start time (described later) and (ii) stores the setting information in the memory 180.

(Acceleration Sensor 120)

The acceleration sensor 120 is a three-axis sensor. The acceleration sensor 120 can be a single-axis sensor or a two-axis sensor. Note, however, that the acceleration sensor 120 is preferably a sensor having three or more axes (e.g., a six-axis sensor or a nine-axis sensor).

(Display Section 130)

The display section 130 is a display for displaying information regarding an activity amount of a user.

(Communication Module 140)

The communication module 140 (receiving section) is a short-distance communication device which is provided for communicating with the smartphone 200. The communication module 140 can be a Bluetooth (registered trademark) communication module, an infrared communication module, a WiFi communication module, an ANT communication module, or another communication module. The Bluetooth (registered trademark) communication module can be, for example, a communication module for Bluetooth (registered trademark) 4.0 (so-called Bluetooth Low Energy).

(Buzzer 150)

The buzzer 150, which is one of three notifying devices included in the activity meter 100, is controlled by the notifying section 113 so as to emit a buzzer sound.

(LED Element 160)

The LED element 160, which is another one of the three notifying devices included in the activity meter 100, is controlled by the notifying section 113 so as to emit light.

(Vibration Unit 170)

The vibration unit 170, which is the other one of the three notifying devices included in the activity meter 100, is controlled by the notifying section 113 so as to vibrate the activity meter 100.

(Memory 180)

The memory 180 is a storage device in which a program is stored in advance. In the memory 180, the setting information is to be stored.

The activity meter 100 is thus configured as described above. Note that the number of notifying devices included in the activity meter 100 is not limited to three. That is, the activity meter 100 can include four or more notifying devices or include only a single notifying device or two notifying devices. The activity meter 100 can further include a physical switch for stopping a notifying device which is being driven.

The following description will discuss a configuration of the smartphone 200.

(Smartphone 200)

As illustrated in FIG. 1, the smartphone 200 includes a CPU 210, communication modules 220 and 230, a touch panel display section 240, an LED element 250, a vibration unit 260, a speaker 270, and a memory 280.

(CPU 210)

After a power supply of the smartphone 200 is turned on, the CPU 210 starts serving as an incoming message processing section 211 by reading a program from the memory 180. After a user carries out an operation to start an application (hereinafter abbreviated as "app") for the activity meter 100, the CPU 210 starts serving as an activity meter setting processing section 212 by reading a program for the app from the memory 280.

(Incoming Message Processing Section 211)

In a case where the smartphone 200 receives an incoming call or an incoming mail, the incoming message processing section 211 (i) notifies, by displaying an incoming message screen on the touch panel display section 240, the activity meter 100 that the smartphone 200 has received the incoming call or the incoming mail (see FIG. 2) and (ii) carries out the following process according to an incoming message setting of the smartphone 200.

That is, the incoming message processing section 211 carries out a process for vibrating the vibration unit 260, a process for controlling the speaker 270 to emit an incoming message sound, or both of the processes.

(Activity Meter Setting Processing Section 212)

The activity meter setting processing section 212 transmits setting information to the activity meter 100 (see FIG. 2), which setting information depends on an operation which is carried out by a user on a setting screen for setting an app for the activity meter 100. Specifically, the activity meter setting processing section 212 sets up the notifying devices in the activity meter 100, by transmitting, to the activity meter 100, setting information indicative of the following four points.

Which of the three notifying devices included in the activity meter 100 is to serve as a device (hereinafter referred to as "target device") to be used for providing a notification Default drive start time (e.g., 10:00 every night) and default drive end time (e.g., 10:01 every night) of the target device What information regarding a measurement result of the activity meter 100 a user is to be notified by the target device A value L which indicates a length of a most recent fixed period in a case where the target device notifies a user of information regarding an exercise amount during the most recent fixed period (Communication Module 220)

The communication module 220 is a communication module for communicating with a base station which is managed by a carrier. Note that the communication module 220 can be a 3G communication module, a WiMAX communication module, an LTE communication module, a PHS communication module, or another communication module.

(Communication Module 230)

The communication module 230 is a short-distance communication device. The communication module 230 can be an infrared ray module, a Bluetooth (registered trademark) communication module, an ANT communication module, or another communication module. The Bluetooth (registered trademark) communication module can be, for example, a communication module for Bluetooth (registered trademark) 4.0 (so-called Bluetooth Low Energy). The Bluetooth (registered trademark) communication module can be another kind of wireless communication module.

(Touch Panel Display Section 240)

The touch panel display section 240 is a display device which also serves as an input device.

(LED Element 250)

The LED element 250 is controlled by the incoming message processing section 211 so as to emit light.

(Vibration Unit 260)

The vibration unit 260 is controlled by the incoming message processing section 211 so as to vibrate the smartphone 200.

(Speaker 270)

The speaker 270 is a sound output device for outputting a sound. The speaker 270 is controlled by the incoming message processing section 211 so as to output an incoming message sound.

(Memory 280)

The memory 280 is a storage device for storing therein various programs.

The smartphone 200 is thus configured as described above.

Note that the app for the activity meter 100 can have a function so that the app stops, by an operation of a user, a notifying device which (i) is included in the activity meter 100 and (ii) is being driven.

(Operation of Activity Meter 100)

Figure 4:
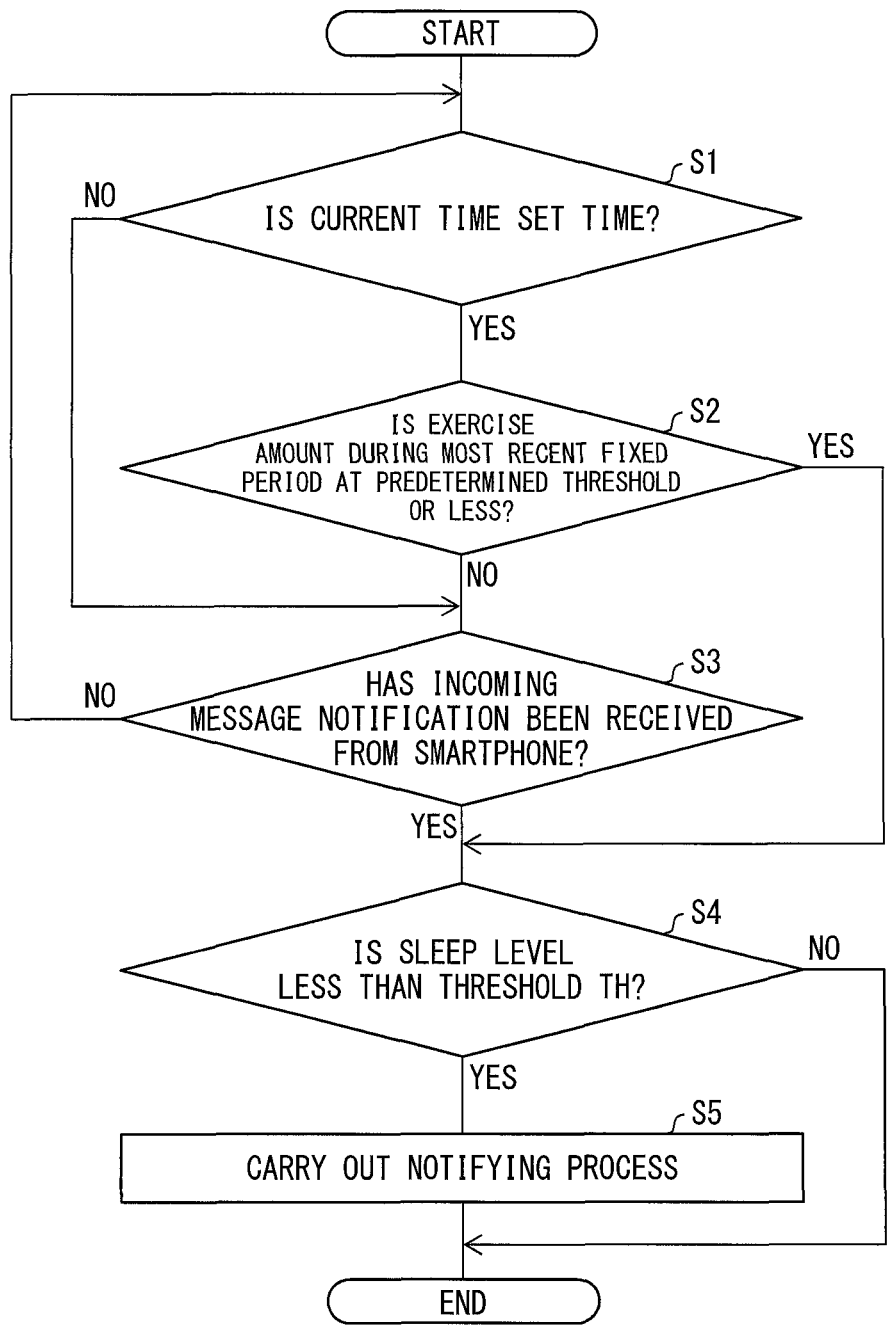
FIG. 4 is a flow chart illustrating an operation in which the activity meter illustrated in FIG. 1 provides a notification to a user.

The following description will discuss, with reference to FIG. 4, an operation in which the activity meter 100 notifies a user of information regarding a measurement result. Note that the activity meter 100 carries out a measurement operation similar to that of a known activity meter. The following description will not discuss the measurement operation of the activity meter 100.

According to the activity meter 100, the target device is set so that in a case where an exercise amount during a most recent single-day period is insufficient, the target device carries out, every day, a process of notifying a user of information which indicates that the exercise amount is insufficient. That is, the value L is set to a "single-day period".

FIG. 4 is a flow chart illustrating an operation in which the activity meter 100 provides a notification to a user.

As illustrated in FIG. 4, the notifying section 113 judges whether or not a current time is time which has been set by a user (specifically, drive start time at which to start driving the target device) (step S1).

In a case where it is judged in the step S1 that the current time is the drive start time for the target device, the activity meter 100 proceeds to a step S2. In a case where it is judged in the step S1 that the current time is not the drive start time for the target device, the activity meter 100 proceeds to a step S3.

In the step S2, the activity amount measurement section 111 judges whether or not an exercise amount during a most recent fixed period (specifically, an exercise amount during a most recent single-day period) is a predetermined threshold or less.

In a case where it is judged in the step S2 that the exercise amount during the most recent single-day period is the predetermined threshold or less, the activity meter 100 proceeds to a step S4. In a case where it is judged in the step S2 that the exercise amount during the most recent single-day period is greater than the predetermined threshold, the activity meter 100 proceeds to the step S3.

In the step S3, the notifying section 113 judges whether or not an incoming message notification has been received from the smartphone 200.

In a case where it is judged in the step S3 that the incoming message notification has been received from the smartphone 200, the activity meter 100 proceeds to the step S4. In a case where it is judged in the step S3 that no incoming message notification has been received from the smartphone 200, the activity meter 100 returns to the step S1.

In the step S4, the sleep level judging section 112 identifies a judgement result of a most recent sleep level of the user. In a case where the judgement result indicates that the most recent sleep level is less than the threshold TH (specifically, "1"), the activity meter 100 proceeds to a step S5. In a case where the judgement result indicates that the most recent sleep level is the threshold TH or greater, the activity meter 100 ends the process in accordance with the flow chart shown in FIG. 4.

In the step S5, the notifying section 113 controls the target device to operate so that the user can recognize content of the notification. In a case where the step S1 has been carried out immediately before the step S3, which is a most recent step, the content of the notification is that the exercise amount during the most recent single-day period is insufficient. In a case where the step S2 has been carried out immediately before the step S3, which is the most recent step, the content of the notification is that the smartphone 200 has received an incoming message.

Note that in a case where the target device is the buzzer 150, the notifying section 113 can control, in the step S5, the buzzer 150 to emit a different buzzer sound in accordance with the content of the notification. In a case where the target device is the LED element 160, the notifying section 113 can control, in the step S5, a light emitting pattern and/or a light emitting color of the LED element 160 to be different in accordance with the content of the notification. Similarly, in a case where the target device is the vibration unit 170, the notifying section 113 can control, in the step S5, a vibration pattern of the vibration unit 170 to be different in accordance with the content of the notification.

After the step S5, the activity meter 100 ends the process in accordance with the flow chart shown in FIG. 4.

Note that the activity meter 100 is configured so that in a case where the activity meter 100 ends the process in accordance with the flow chart shown in FIG. 4, the activity meter 100 starts again the process in accordance with the flow chart shown in FIG. 4.

As is clear from the above description of the operation of the activity meter 100 (particularly the descriptions of the steps S4 and S5), the activity meter 100 is configured so that only in a case where the activity meter 100 judges that the user is awake, the activity meter 100 operates the target device so that the user can recognize the content of the notification.

(Additional Matter 1 Regarding Embodiment 1 and Embodiments 2 Through 3 (Described Later))

According to Embodiment 1, the threshold TH is assumed to be "1". However, the threshold TH is not limited to "1" but can be, for example, "3". That is, it is possible that only in a case where the activity meter judges that a user is awake or the user is in a light sleep, the activity meter operates the target device so that the user (the user who is awake or the user who was awoken by the operation of the target device) can recognize the content of the notification.

(Additional Matter 2 Regarding Embodiment 1 and Embodiments 2 Through 3 (Described Later))

In a case where the smartphone receives an incoming call or mail, the incoming message processing section can transmit, to the activity meter, notification information including (i) a message indicating that the smartphone has received the incoming call or mail and (ii) information for specifying an incoming message sender (e.g., a telephone number and a name of the incoming message sender).

Then, in a case where a specific incoming message sender is indicated by the information, the notifying section can control, at a time point at which the notification information is received, the target device to operate so that the user can recognize that the smartphone has received an incoming message, the notifying section thus controlling the target device regardless of a most recent sleep level.

Note that examples of the case where a specific incoming message sender is indicated by the information encompass a case where a telephone number or a name of the incoming message sender is registered in the activity meter. Further, the activity meter can include an operation accepting section (not illustrated) for accepting a registration of the telephone number or the name.

(Additional Matter 3 Regarding Embodiment 1 and Embodiments 2 Through 3 (Described Later))

The smartphone can be configured so that the threshold TH can be set via the setting screen for the app for the activity meter. The smartphone can be configured so that in a case where a user carries out setting for causing the notifying device to provide a plurality of kinds of notifications, the threshold TH can be set for each of the plurality of kinds of notifications.

For example, the smartphone can be configured so that (i) the threshold TH is set to "1" for a notification of information indicating that an exercise amount is insufficient and (ii) the threshold TH is set to "3" for a notification that the smartphone has received an incoming message.

In such a case, only during a period during which a most recent sleep level indicates that a user is not in an asleep state, the notifying section notifies the user of the information indicating that the exercise amount is insufficient. Further, only during a period during which the most recent sleep level indicates that the user is not in a deep sleep state, the notifying section notifies the user of the information indicating that the smartphone has received an incoming message.

(Additional Matter 4 Regarding Embodiment 1 and Embodiments 2 Through 3 (Described Later))

At set time at which an alarm is set, the smartphone can notify the activity meter of information which indicates that a current time is the set time for the alarm. In such a case, the notifying section of the activity meter having received the notification carries out the following operations regardless of a most recent sleep level at a time point at which the activity meter receives the notification: (i) display the notified information on the display section 130 and (ii) drive the target device.

In a case where the smartphone receives disaster information (e.g., an emergency earthquake warning), the smartphone can notify the activity meter of information which indicates that the smartphone has received the disaster information. In such a case, the notifying section of the activity meter having received the notification carries out the following operations regardless of a most recent sleep level at a time point at which the activity meter receives the notification: (i) display the notified information on the display section 130 and (ii) drive the target device.

(Additional Matter 5 Regarding Embodiment 1 and Embodiments 2 Through 3 (Described Later))

In order to work the present invention, it is possible to use, instead of the smartphone 200, other kinds of mobile devices (e.g., a feature phone, a tablet device, a mobile PC, etc.) which have characteristics similar to that of the smartphone 200.

(Advantage of Activity Meter 100)

As described above, the activity meter 100 includes the sleep level judging section 112 and the notifying section 113. The sleep level judging section 112 repeatedly judges a sleep level of a user wearing the activity meter 100. The notifying section 113 automatically notifies the user of specific information (according to Embodiment 1, information indicating that the exercise amount is insufficient and information indicating that the smartphone 200 has received an incoming message) only during a period during which a most recent sleep level is less than a predetermined level.

According to the configuration, the activity meter 100 does not notify the user of the specific information during a period during which the most recent sleep level of the user is the predetermined level or greater.

Therefore, the activity meter 100 has such an advantage of being unlikely to disturb a user in a deep sleep by notifying the user of the specific information.

Embodiment 2

Figure 5:
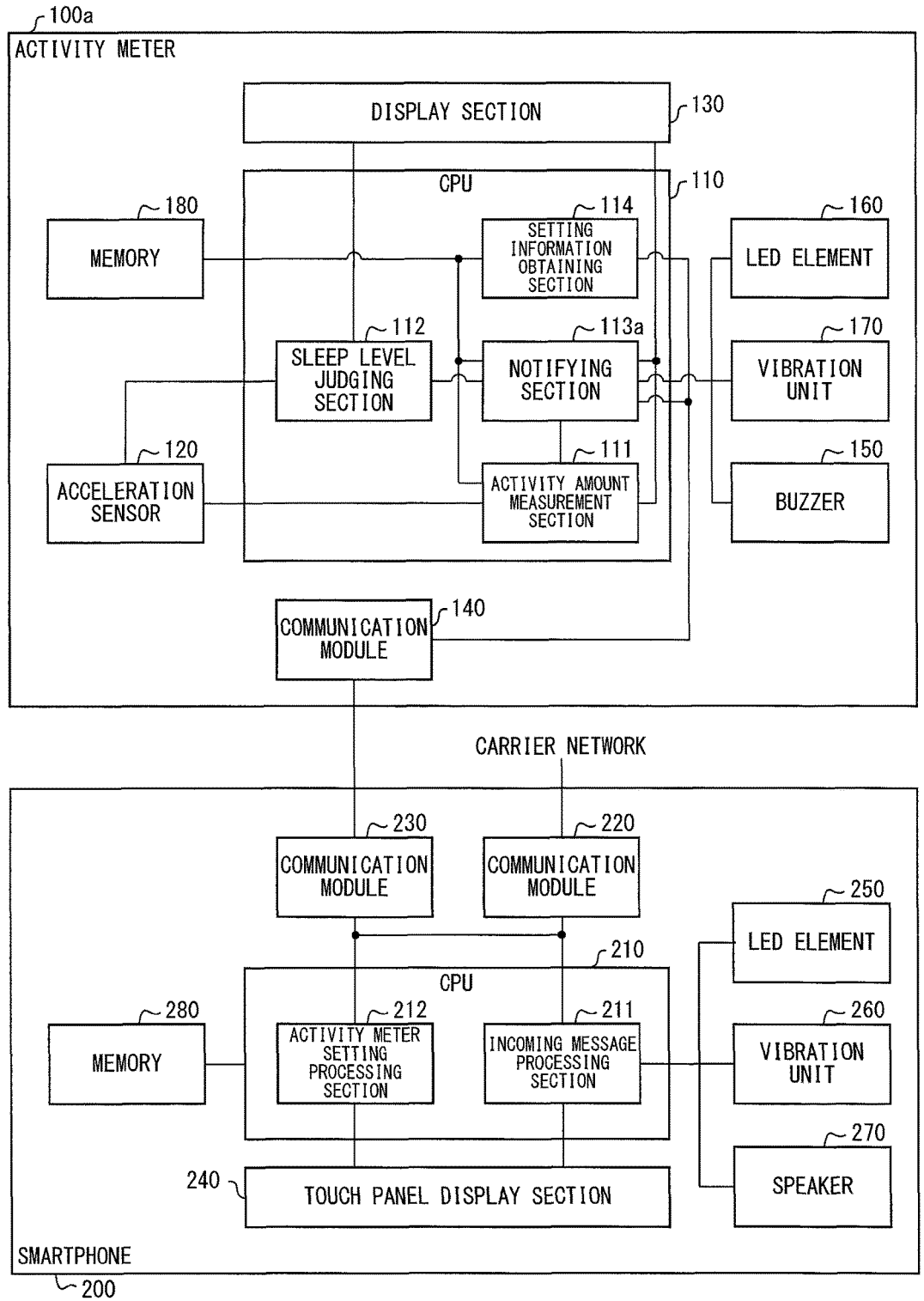
FIG. 5 is a view illustrating main configurations of an activity meter and a smartphone according to Embodiment 2 of the present invention.
Figure 6:
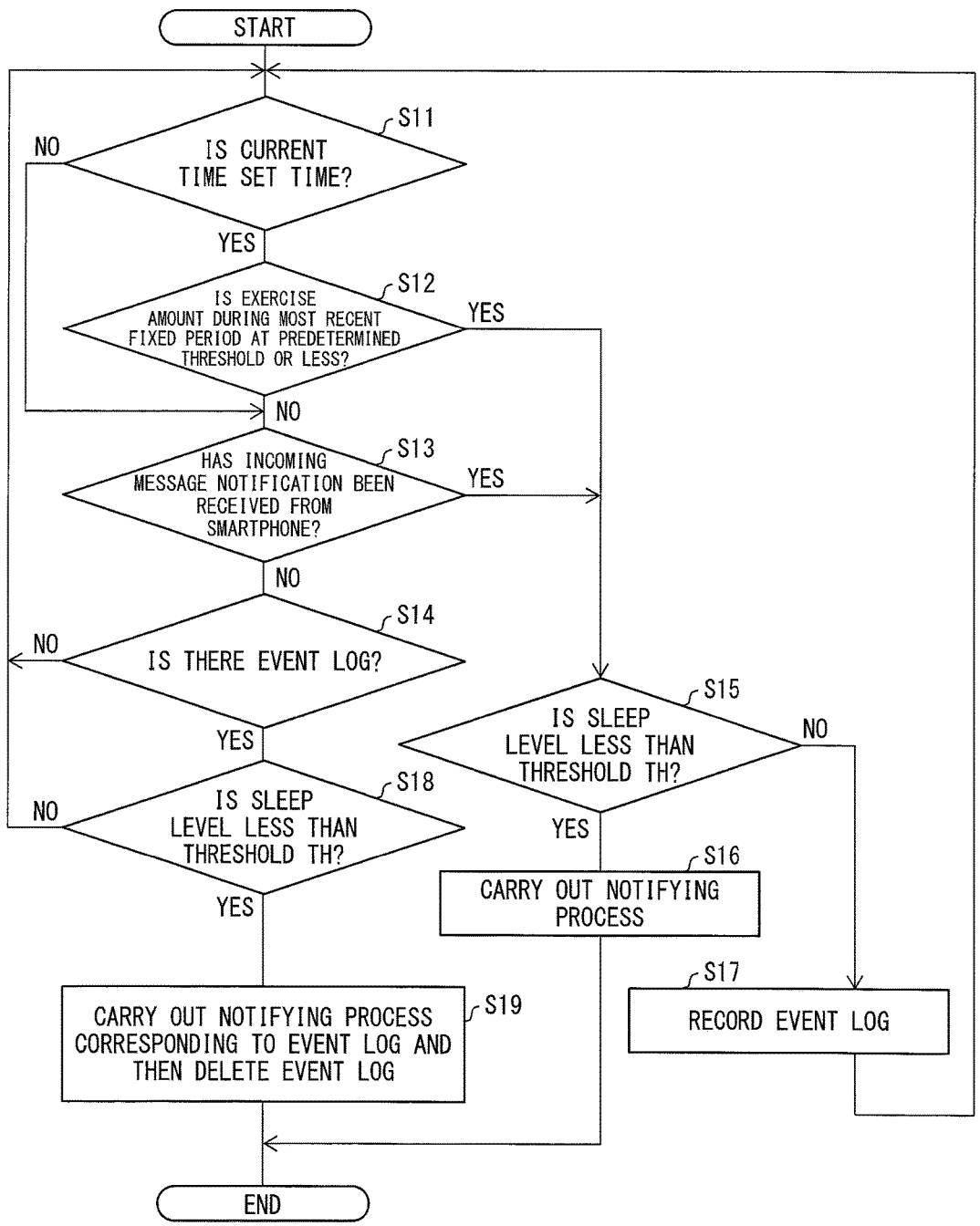
FIG. 6 is a flow chart illustrating an operation in which the activity meter illustrated in FIG. 5 provides a notification to a user.

The following description will discuss, with reference to FIGS. 5 and 6, an activity meter and a smartphone according to another embodiment of the present invention. Note that for convenience, members having functions completely or substantially identical to those described in Embodiment 1 will be given the same reference signs, and descriptions of such members will be omitted as a general rule.

First, the following description will discuss, with reference to FIG. 5, configurations of the activity meter and the smartphone according to Embodiment 2.

FIG. 5 is a block diagram illustrating main configurations of the activity meter and the smartphone according to Embodiment 2.

(Activity Meter 100a)

As illustrated in FIG. 5, an activity meter 100a according to Embodiment 2 includes a CPU 110, an acceleration sensor 120, a display section 130, a communication module 140, a buzzer 150, an LED element 160, a vibration unit 170, and a memory 180.

(CPU 110)

In a case where a power supply of the activity meter 100a is turned on, the CPU 110 starts serving as an activity amount measurement section 111, a sleep level judging section 112, a notifying section 113a, and a setting information obtaining section 114.

(Notifying Section 113a)

At time set by a user with use of a smartphone 200, the notifying section 113a provides, to the user, a notification based on a measurement value of an activity amount which measurement value has been measured by the activity amount measurement section 111 until a current time. Specifically, the notifying section 113a (i) displays, on the display section 130, content to be notified and (ii) drives the buzzer 150, the LED element 160, or the vibration unit 170.

In a case where the notifying section 113a receives an incoming message notification from the smartphone 200, the notifying section 113a (i) displays, on the display section 130, information which indicates that the smartphone 200 has received the incoming message and (ii) drives the buzzer 150, the LED element 160, or the vibration unit 170.

Note that in a case where a sleep level of the user during a most recent period T is a predetermined threshold TH or greater at the time set by the user, the notifying section 113a provides a notification in accordance with the measurement value of the activity amount at a later time point at which the sleep level of the user during a most recent period T has become less than the predetermined threshold TH. The same applies to a case where a sleep level of the user during a most recent period T is the predetermined threshold TH or greater at time at which the notifying section 113 receives the incoming message notification from the smartphone 200.

(Smartphone 200)

The smartphone 200 according to Embodiment 2 is identical in configuration to the smartphone 200 according to Embodiment 1, and therefore the description of the smartphone 200 according to Embodiment 2 will be omitted.

(Operation of Activity Meter 100a)

The following description will discuss, with reference to FIG. 6, an operation in which the activity meter 100a notifies a user of information regarding a measurement result.

Note that, according to the activity meter 100a, as with the activity meter 100, the target device is set so that in a case where an exercise amount in a most recent single-day period is insufficient, the target device carries out, every day, a process of notifying a user of information which indicates that the exercise amount is insufficient. That is, the value L is set to a "single-day period".

FIG. 6 is a flow chart illustrating an operation in which the activity meter 100a provides a notification to a user.

As illustrated in FIG. 6, the notifying section 113a judges whether or not a current time is time which has been set by a user (specifically, drive start time at which to start driving the target device) (step S11).

In a case where it is judged in the step S11 that the current time is the drive start time for the target device, the activity meter 100a proceeds to a step S12. In a case where it is judged in the step S11 that the current time is not the drive start time for the target device, the activity meter 100a proceeds to a step S13.

In the step S12, the activity amount measurement section 111 judges whether or not an exercise amount during a most recent fixed period (specifically, an exercise amount during a most recent single-day period) is a predetermined threshold or less.

In a case where it is judged in the step S12 that the exercise amount during the most recent single-day period is the predetermined threshold or less, the activity meter 100a proceeds to a step S15. In a case where it is judged in the step S12 that the exercise amount during the most recent single-day period is greater than the predetermined threshold, the activity meter 100 proceeds to the step S13.

In the step S13, the notifying section 113a judges whether or not an incoming message notification has been received from the smartphone 200.

In a case where it is judged in the step S13 that the incoming message notification has been received from the smartphone 200, the activity meter 100a proceeds to the step S15. In a case where it is judged in the step S3 that no incoming message notification has been received from the smartphone 200, the activity meter 100 proceeds to a step S14.

In the step S14, the notifying section 113a judges whether or not an event log (described later) is stored in the memory 180.

In a case where it is judged in the step S14 that the event log is stored in the memory 180, the activity meter 100a proceeds to a step S18. In a case where it is judged in the step S14 that no event log is stored in the memory 180, the activity meter 100a returns to the step S11.

In the step S15, the sleep level judging section 112 identifies a judgement result of a most recent sleep level of the user. In a case where the judgement result indicates that the most recent sleep level is less than the threshold TH (specifically, "1"), the activity meter 100a proceeds to a step S16. In a case where the judgement result indicates that the most recent sleep level is the threshold TH or greater, the activity meter 100a proceeds to a step S17.

In the step S16, the notifying section 113a controls the target device to operate so that the user can recognize content of the notification. After the step S16, the activity meter 100a ends the process in accordance with the flow chart shown in FIG. 6.

In step S17, the notifying section 113a stores, in the memory 180, an event log including (i) a current time and (ii) content to be notified at a time point at which a most recent sleep level of the user becomes less than the threshold TH (i.e., soon after the user wakes up). After the step S17, the activity meter 100a returns to the step S11.

In the step S18, the sleep level judging section 112 identifies a judgement result of a most recent sleep level of the user. In a case where the judgement result indicates that the most recent sleep level is less than the threshold TH, the activity meter 100a proceeds to a step S19. In a case where the judgement result indicates that the most recent sleep level is the threshold TH or greater, the activity meter 100a returns to the step S11.

In the step S19, for each of one or more event logs stored in the memory 180, the notifying section 113a controls a target device to operate so that the user can recognize the content of the notification included in the each of one or more event logs. In the step S19, the notifying section 113a deletes all of the one or more event logs stored in the memory 180. After the step S19, the activity meter 100a ends the process in accordance with the flow chart shown in FIG. 6.

Note that the activity meter 100a is configured so that in a case where the activity meter 100a ends the process in accordance with the flow chart shown in FIG. 6, the activity meter 100a starts again the process in accordance with the flow chart shown in FIG. 6.

As is clear from the description of the operation of the activity meter 100a, in a case where the most recent sleep level of the user at a time point at which the communication module 140 receives an incoming message notification indicates that the user is in an asleep state, the notifying section 113a operates as follows: the notifying section 113a provides the received incoming message notification to the user at the start of a period during which the most recent sleep level of the user indicates that the user is not in an asleep state.

(Advantage of Activity Meter 100a)

As described above, as with the activity meter 100, the activity meter 100a includes the sleep level judging section 112 and the notifying section 113a. The sleep level judging section 112 repeatedly judges a sleep level of a user wearing the activity meter 100. The notifying section 113a automatically notifies the user of specific information (according to Embodiment 2, information indicating that the exercise amount is insufficient and information indicating that the smartphone 200 has received an incoming message) only during a period during which a most recent sleep level is less than a predetermined level.

Therefore, as with the activity meter 100, the activity meter 100a has an advantage of being unlikely to disturb a user in a deep sleep by notifying the user of the specific information.

In addition, as described above, in a case the activity meter 100a is required to provide a notification to a user while the user is in a deep sleep (e.g., an incoming message is received by the smartphone 200), the activity meter 100a provides a notification (e.g., an incoming message notification) to the user soon after the user wakes up. Therefore, in a case the activity meter 100a is required to provides a notification to a user occurs while the user is in a deep sleep, the activity meter 100a brings about another effect of allowing the user to recognize content of the notification soon after the user wakes up.

Embodiment 3

Figure 7:
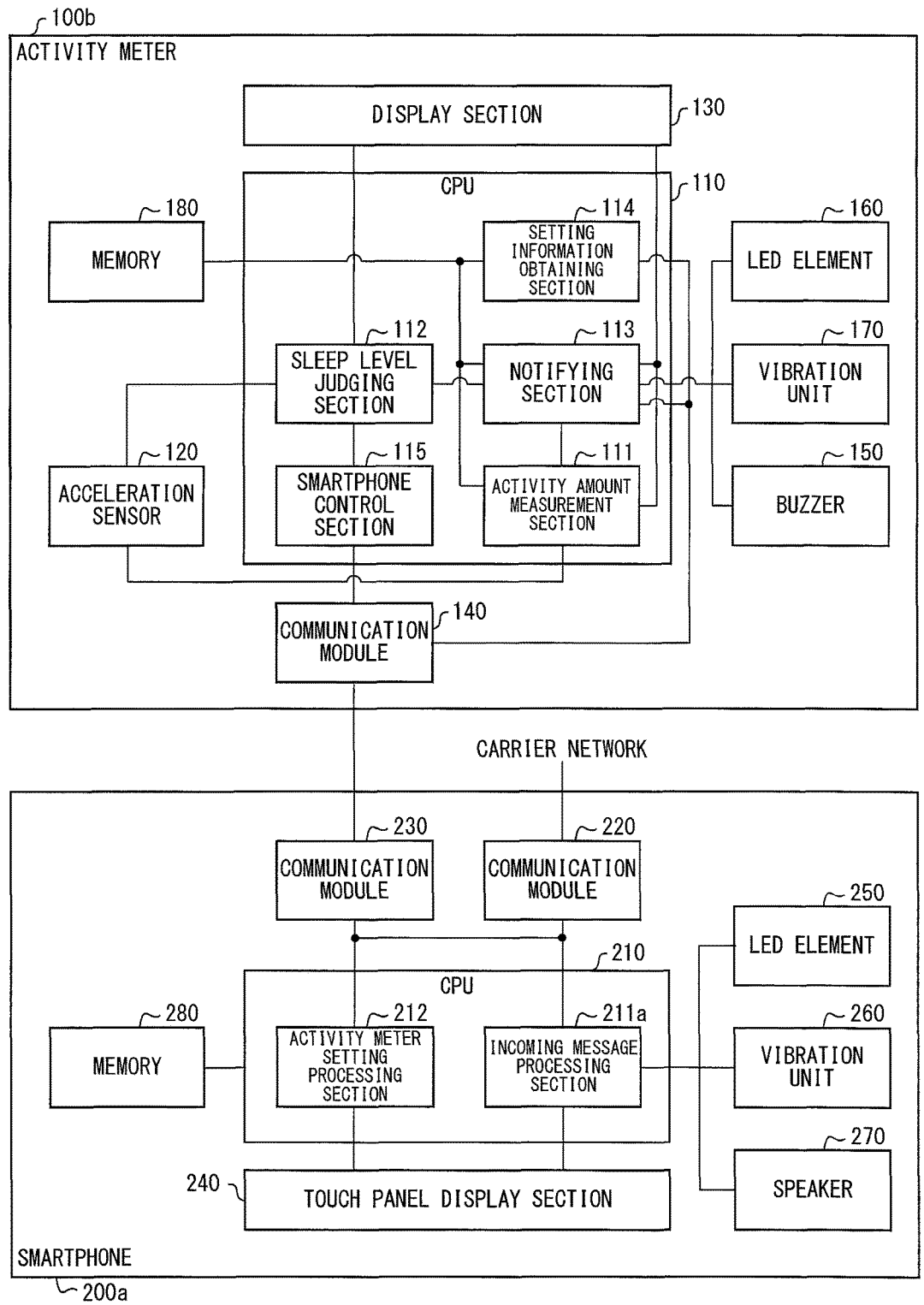
FIG. 7 is a block diagram illustrating main configurations an activity meter and a smartphone according to Embodiment 3 of the present invention.
Figure 8:
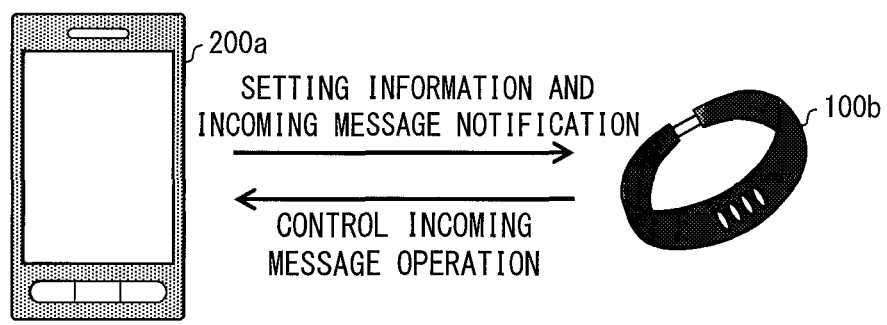
FIG. 8 is a view illustrating appearances of the activity meter and the smartphone illustrated in FIG. 7.
Figure 9:
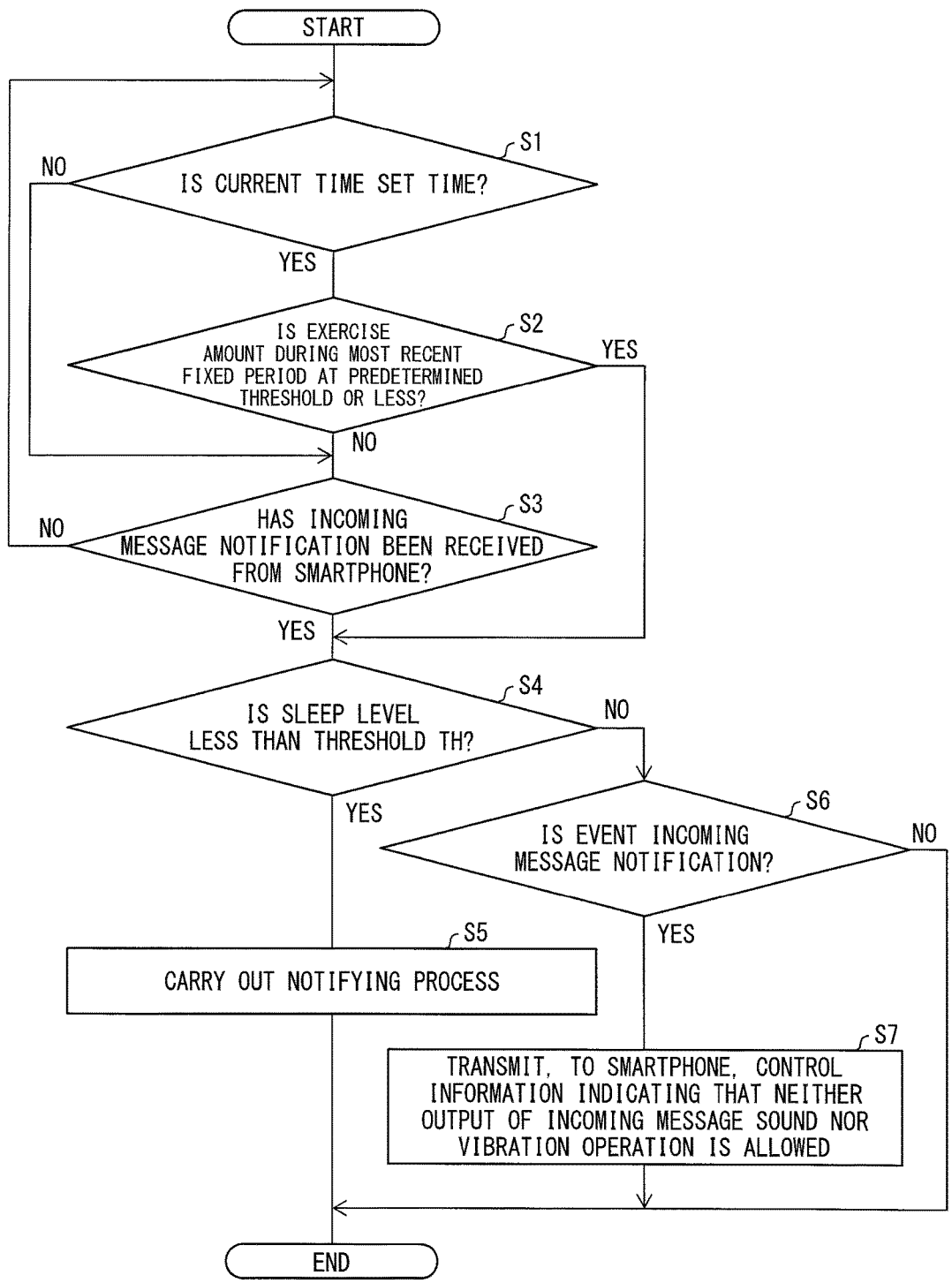
FIG. 9 is a flow chart illustrating an operation in which the activity meter illustrated in FIG. 7 provides a notification to a user.

The following description will discuss, with reference to FIGS. 7 through 9, another embodiment of the present invention. Note that for convenience, members having functions completely or substantially identical to those described in Embodiments 1 and 2 will be given the same reference signs, and descriptions on such members will be omitted.

First, the following description will discuss, with reference to FIGS. 7 and 8, configurations of an activity meter and a smartphone according to Embodiment 3.

FIG. 7 is a block diagram illustrating main configurations of the activity meter and the smartphone according to Embodiment 3. FIG. 8 is a view illustrating appearances the activity meter and the smartphone according to Embodiment 3.

(Activity Meter 100b)

As illustrated in FIG. 7, an activity meter 100b according to Embodiment 3 includes a CPU 110, an acceleration sensor 120, a display section 130, a communication module 140, a buzzer 150, an LED element 160, a vibration unit 170, and a memory 180.

(CPU 110)

In a case where a power supply of the activity meter 100b is turned on, the CPU 110 starts serving as an activity amount measurement section 111, a sleep level judging section 112, a notifying section 113, and a setting information obtaining section 114, and a smartphone control section 115.

(Smartphone Control Section 115)

In a case where a smartphone control section 115 (control section) receives, from a smartphone 200a, a notification that the smartphone 200a has received an incoming message, the smartphone control section 115 controls an incoming message operation in the smartphone 200a in accordance with a judgement result of a most recent sleep level of a user (see FIG. 8).

Specifically, in a case where the most recent sleep level of the user is a threshold TH or greater, the smartphone control section 115 transmits, to the smartphone 200a, control information which indicates that neither an output of an incoming message sound nor a vibration operation is allowed. Note that regardless of the threshold TH, the smartphone control section 115 can transmit the control information to the smartphone 200a in a case where the most recent sleep level of the user is 3 or greater.

The following description will discuss a configuration of the smartphone 200a.

(Smartphone 200a)

As illustrated in FIG. 7, the smartphone 200a includes a CPU 210, communication modules 220 and 230, a touch panel display section 240, an LED element 250, a vibration unit 260, a speaker 270, and a memory 280.

(CPU 210)

After the power supply of the smartphone 200 is turned on, the CPU 210 starts serving as an incoming message processing section 211. After a user carries out an operation to start an app for the activity meter 100b, the CPU 210, which has been serving as the incoming message processing section 211, starts serving as an incoming message processing section 211a and an activity meter setting processing section 212.

(Incoming Message Processing Section 211a)

In a case where the smartphone 200 receives an incoming call or mail, the incoming message processing section 211a notifies, by displaying an incoming message screen on the touch panel display section 240, the activity meter 100b that the smartphone 200a has received the incoming call or mail (see FIG. 2).

Immediately after a fixed period has passed after the incoming message processing section 211a notifies the activity meter 100b that the smartphone 200a has received the incoming call or mail, the incoming message processing section 211a carries out the following process in accordance with an incoming message setting of the smartphone 200a except for a case where the incoming message processing section 211a receives control information from the activity meter 100b within the fixed period, the control information indicating that neither an output of an incoming message sound nor a vibration operation is allowed.

Specifically, the incoming message processing section 211a carries out a process for vibrating the vibration unit 260, a process for controlling the speaker 270 to emit an incoming message sound, or both of the processes.

The smartphone 200a is thus configured as described above.

(Operation of Activity Meter 100b)

The following description will discuss, with reference to FIG. 9, an operation in which the activity meter 100b notifies a user of information regarding a measurement result.

According to the activity meter 100b, as with the activity meter 100 and the activity meter 100a, the target device is set so that in a case where an exercise amount in a most recent single-day period is insufficient, the target device carries out, every day, a process of notifying a user of information which indicates that the exercise amount is insufficient. That is, the value L is set to a "single-day period".

FIG. 9 is a flow chart illustrating an operation in which the activity meter 100b provides a notification to a user.

The activity meter 100b carries out a process in a step S1 through a step S4, exactly as with the activity meter 100.

In a case where a judgement result indicates that a most recent sleep level is less than a threshold TH (specifically, "1"), the activity meter 100b proceeds to a step S5. In a case where the judgement result indicates that the most recent sleep level is the threshold TH or greater, the activity meter 100b proceeds to a step S7.

In the step S5, the notifying section 113 controls a target device to operate so that a user can recognize content of a notification. After the step S5, the activity meter 100b ends the process in accordance with the flow chart shown in FIG. 9.

In a step S6, the notifying section 113 checks whether or not the content of the notification indicates that the smartphone 200a has received an incoming message.

In a case where the content of the notification indicates that the smartphone 200a has received an incoming message, the activity meter 100b proceeds to the step S7. In a case where the content of the notification does not indicate that the smartphone 200a has received an incoming message, the activity meter 100b ends the process in accordance with the flow chart shown in FIG. 9.

In the step S7, the smartphone control section 115 transmits, to the smartphone 200a, control information which indicates that neither an output of an incoming message sound nor a vibration operation is allowed. After the step S7, the activity meter 100b ends the process in accordance with the flow chart shown in FIG. 9.

Note that the activity meter 100b is configured so that in a case where the activity meter 100b ends the process in accordance with the flow chart shown in FIG. 9, the activity meter 100 starts again the process in accordance with the flow chart shown in FIG. 9.

(Additional Matter 1 Regarding Embodiment 3)

In a case where the most recent sleep level of the user is less than the threshold TH, the smartphone control section 115 transmits, to the smartphone 200a, the control information indicating that both an output of an incoming message sound and a vibration operation are allowed.

In a case where the incoming message processing section 211a receives the control information from the activity meter 100b within a fixed period after the incoming message processing section 211a notifies the activity meter 100b that the smartphone 200a has received the incoming call or mail, the incoming message processing section 211a can carry out, immediately after the activity meter 100b has received the control information, the above-mentioned process in accordance with the incoming message setting of the smartphone 200a.

(Additional Matter 2 Regarding Embodiment 3)

In a case where the smartphone 200a receives an incoming call or mail, the incoming message processing section 211a can transmit, to the activity meter 100b, notification information including (i) a message indicating that the smartphone 200a has received the incoming call or mail and (ii) information for specifying an incoming message sender.

In a case where the information indicates a specific incoming message sender, the smartphone control section 115 can transmit, regardless of a most recent sleep level, control information to the smartphone 200a, the control information indicating that both an output of an incoming message sound and a vibration operation are allowed.

Embodiment 4

Figure 10:
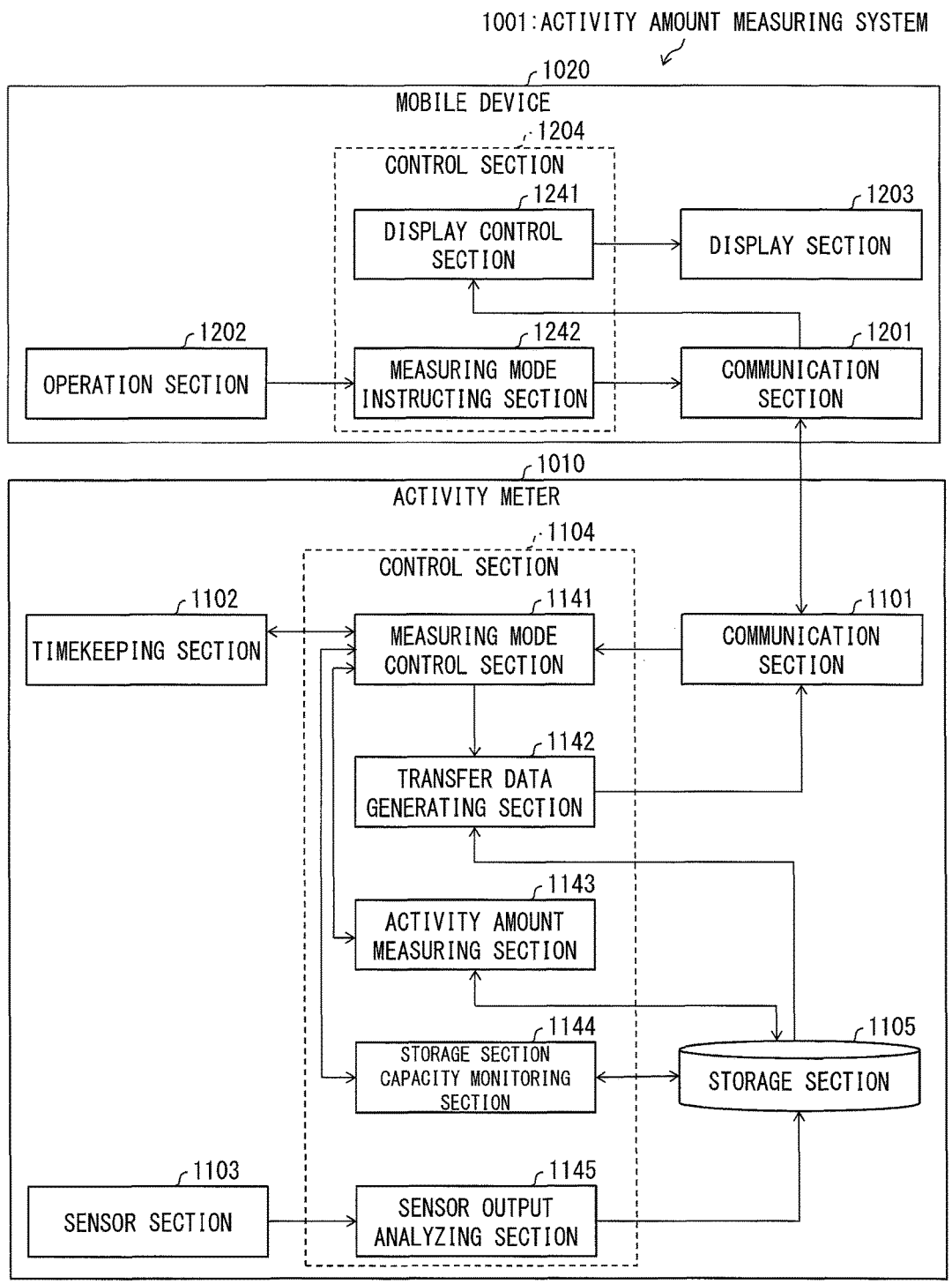
FIG. 10 is a block diagram illustrating an activity amount measuring system according to Embodiment 4.
Figure 12:
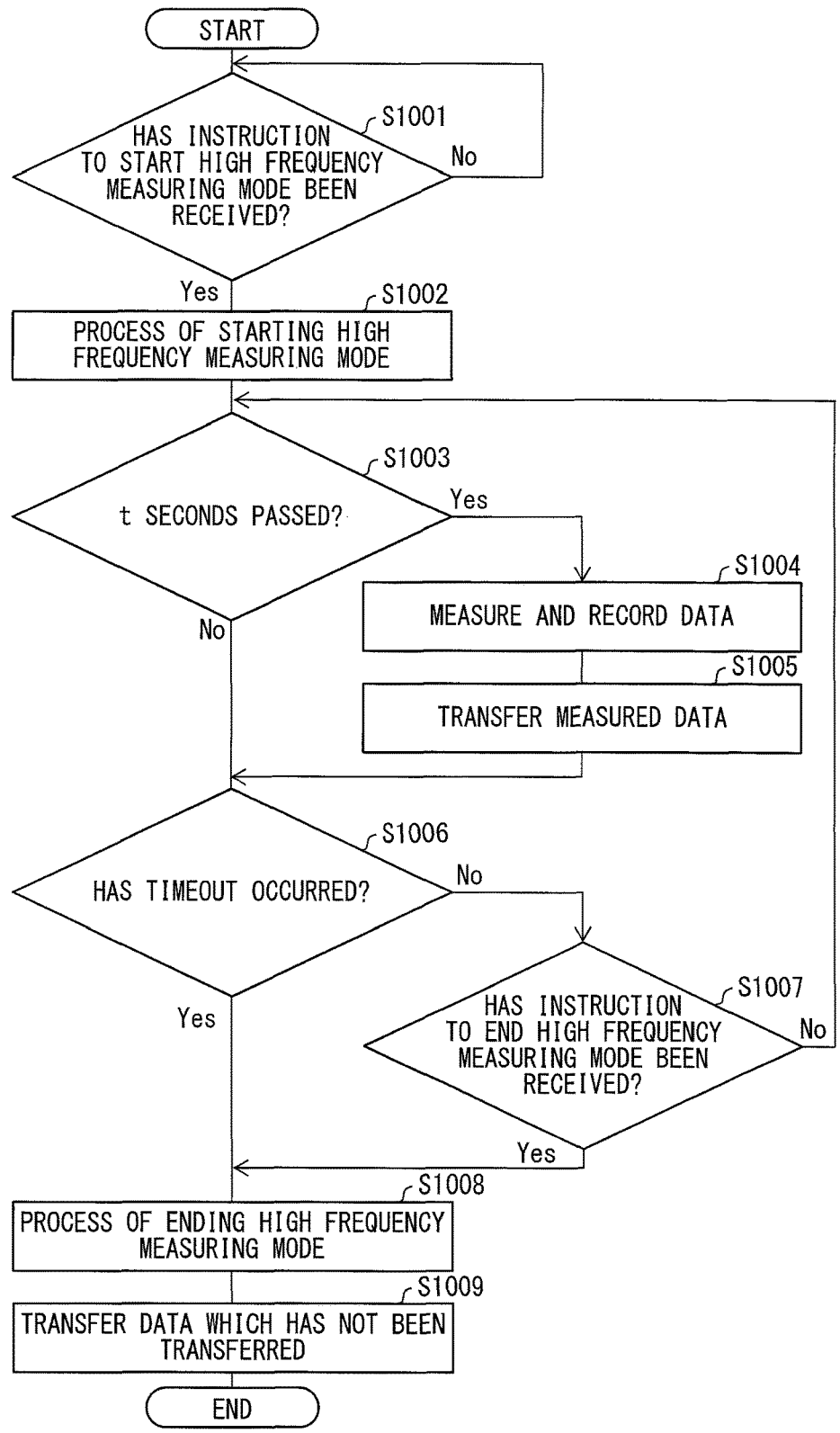
FIG. 12 is a flow chart illustrating a flow of a process from a start to an end of a high frequency measuring mode, which process is carried out by an activity meter included in an activity amount measuring system of Embodiment 4.

The following description will discuss Embodiment 4 of the present invention with reference to FIGS. 10 through 12.

(Configuration of Activity Amount Measuring System 1)

An overview of an activity amount measuring system 1001 according to Embodiment 4 will be provided below with reference to FIG. 11. FIG. 11 is a view illustrating an appearance of the activity amount measuring system 1001.

As illustrated in FIG. 11, the activity amount measuring system 1001 includes (i) an activity meter (activity amount measuring device) 1010 and (ii) a mobile device 1020. The activity meter 1010 and the mobile device 1020 are able to establish communication via short-distance wireless communication. In Embodiment 4, the short-distance wireless communication between the activity meter 1010 and the mobile device 1020 is carried out by use of low-power-consumption short-distance wireless communication. Examples of the low-power-consumption short-distance wireless communication encompass Bluetooth (registered trademark) 4.0 (known as Bluetooth Low Energy) and ANT (registered trademark).

The activity meter 1010 measures an activity amount of a user and then transmits, to the mobile device 1020, activity amount information which indicates the activity amount thus measured. Meanwhile, in a case where the mobile device 1020 has received the activity amount information from the activity meter 1010, the mobile device 1020 presents, to the user, the activity amount indicated by the activity amount information thus received. This is how an activity amount of a user, which has been measured by the activity meter 1010, is presented to the user by the mobile device 1020.

The activity amount thus measured by the activity meter 1010 is categorized into (i) a primary activity amount (e.g., the number of steps) sequentially outputted from a sensor (e.g., acceleration sensor) and (ii) a secondary activity amount (e.g., any activity amount other than the number of steps) which is, as needed, calculated based on the primary activity amount. In Embodiment 4, the term "activity amount measurement" mainly refers to calculation of a secondary activity amount based on a primary activity amount.

On the mobile device 1020, an application for presenting an activity amount to the user (e.g., a walking application for supporting walking) is executed. In a case where the walking application is executed, the mobile device 1020 displays, on a display (touch panel) as illustrated in FIG. 11, (i) a map showing a walking route and (ii) some activity amounts (EX quantity, the number of steps, walking distance, walking pace, and consumed calorie in the example of FIG. 11).

In Embodiment 4, the activity meter 1010 is a wrist band-type activity meter which can be put on a wrist of a user as illustrated in FIG. 11. Note, however, that the a of the activity meter 1010 is not limited to a wrist band-type, provided that the activity meter 1010 can be put on the user's body, directly or indirectly. Examples of the activity meter 1010 encompass (i) a necklace-type activity meter which can be put on the user's neck and (ii) a clip-type activity meter which can be put on the user's body via clothing.

In Embodiment 4, the mobile device 1020 is a smartphone as illustrated in FIG. 11. Note, however, that the mobile device 1020 is not limited to a smartphone, provide that the mobile device 1020 is a portable information processing device. Examples of the mobile device 1020 encompass a mobile phone, a PDA (Personal Digital Assistant), and a tablet PC (Personal Computer).

The activity amount measuring system 1001 according to Embodiment 4 is mainly characterized in that (1) the activity meter 1010 has a plurality of measuring modes that differ in length of period during which to measure an activity amount, (2) the mobile device 1020 transmits, to the activity meter 1010, a mode change command that instructs a change in measuring mode (i.e., change in length of period during which to measure an activity amount), and (3) the activity meter 1010 changes a measuring mode in accordance with the mode change command thus received.

In a case where the mobile device 1020 detects a specific user operation (e.g., tapping "start button") while the walking application is being executed, the mobile device 1020 transmits, to the activity meter 1010, a mode change command that instructs a change in measuring mode, from a normal mode (first measuring mode) to a high frequency measuring mode (second measuring mode). Note that a "normal mode" refers to a measuring mode in which an activity amount is measured during a predetermined first period (e.g., 24 hours). Note also that a "high frequency measuring mode" refers to a measuring mode in which an activity amount is measured during a predetermined second period (e.g., 5 minutes) which is shorter than the first period in addition to the measurement in the normal mode (i.e., the high frequency measuring mode according to Embodiment 4 can be described as a measuring mode in which activity amount measurement during first periods and activity amount measurement during second periods are both carried out). In a case where the activity meter 1010 has received a mode change command, the activity meter 1010 changes a measuring mode from the normal mode to the high frequency measuring mode. This allows a user to confirm, substantially in real time, an activity amount which is updated with high frequency.

(Configuration of Activity Meter 1010 and Mobile Device 1020)

Configurations of the activity meter 1010 and the mobile device 1020 will be described next with reference to FIG. 10. FIG. 10 is a block diagram illustrating the configurations of the activity meter 1010 and of the mobile device 1020.

The activity meter 1010 measures an activity amount of a user and then transmits, to the mobile device 1020, activity amount information which indicates the activity amount thus measured. As illustrated in FIG. 10, the activity meter 1010 includes a communication section (receiving section) 1101, a timekeeping section 1102, a sensor section 1103, a control section 1104, and a storage section 1105.

The communication section 1101 communicates with the mobile device 1020 via short-distance wireless communication. Specifically, the communication section 1101 transmits, to the mobile device 1020, activity amount information which indicates an activity amount measured. The communication section 1101 also receives, from the mobile device 1020, a mode change command which instructs a change in measuring mode.

The timekeeping section 1102 is a timer for notifying the control section 1104 that an amount of time specified by the control section 1104 has passed. For example, in a case where time t is specified by the control section 1104 at time t0, the timekeeping section 1102 notifies the control section 1104 at times t0+t, t0+2×t, t0+3×t . . . . In a case where a plurality of times t1, t2, . . . , to are specified by the control section 1104 at time t0, the timekeeping section 1102 notifies, in a parallel manner, the control section 1104 at times time t0+t1, t0+2×t1, . . . , at times time t0+t2, t0+2×t2, . . . , and at times time t0+tn, t0+2×tn, . . . .

The sensor section 1103 includes at least an acceleration sensor. The sensor section 1103 supplies, to the control section 1104, a sensor signal which indicates acceleration detected. In Embodiment 4, the sensor section 1103 includes a three-axis acceleration sensor. Alternatively, the sensor section 1103 can include a two-axis acceleration sensor or a one-axis acceleration sensor, instead of a three-axis acceleration sensor. Alternatively, the sensor section 1103 can include, in addition to an acceleration sensor, a gyrosensor, an altitude (atmospheric pressure) sensor, a temperature sensor, a humidity sensor, and/or the like. Referring to sensor signals supplied from these sensors, it is possible to more accurately calculate an activity amount which depends on a posture of a user and on a surrounding environment.

The storage section 1105 stores various data such as data received by the communication section 1101 and data generated by the control section 1104.

The control section 1104 comprehensively controls the sections of the activity meter 1010. The control section 1104 is configured by, for example, a CPU (central processing unit) or the like. As illustrated in FIG. 10, the control section 1104 includes a measuring mode control section 1141, a transfer data generating section 1142, an activity amount measuring section (measuring section) 1143, a storage section capacity monitoring section (storage section capacity monitoring section) 1144, and a sensor output analyzing section 1145.

The sensor output analyzing section 1145 counts the number of steps (primary activity amount) by referring to a sensor signal supplied from the sensor section 1103. Counting of the number of steps in accordance with a sensor signal indicative of acceleration can be carried out by use of a known algorithm. The number of steps thus counted by the sensor output analyzing section 1145 is stored as sensor information in the storage section 1105.

The activity amount measuring section 1143 calculates various activity amounts (secondary activity amount) based on the number of steps stored in the storage section 1105. Calculation of the various activity amounts based on the number of steps can be carried out by use of a known algorithm. An activity amount calculated by the activity amount measuring section 1143 is stored as activity amount information in the storage section 1105. Note that timings with which the activity amount measuring section 1143 carries out activity amount measurement are controlled by the measuring mode control section 1141 described later.

The transfer data generating section 1142 reads out, from the storage section 1105, activity amount information which has not been transmitted. Then, the transfer data generating section 1142 generates transfer data which contains the activity amount information thus read out. Then, the transfer data thus generated is transmitted to the mobile device 1020 via the communication section 1101. Note that timings with which the transfer data generating section 1142 generates transfer data, that is, timings with which the activity amount information is transmitted to the mobile device 1020 are controlled by the measuring mode control section 1141 described later. Note also that activity amount information, which has been read out by the transfer data generating section 1142 and has been transmitted to the mobile device 1020, is preferably deleted from the storage section 1105 in order for a capacity of the storage section 1105 to be efficiently used.

The storage section capacity monitoring section 1144 judges whether or not a space available in the storage section 1105 for recording data is sufficient. A result of the judgment by the storage section capacity monitoring section 1144 is supplied to the measuring mode control section 1141. Timings with which the storage section capacity monitoring section 1144 judges the available space are controlled by the measuring mode control section 1141 described later.

According to the mode change command obtained via the communication section 1101, the measuring mode control section 1141 controls (i) a timing with which to measure the activity amount, (ii) a timing with which to transmit the activity amount information, and (iii) a timing with which to judge the available space. Specifically, the measuring mode control section 1141 supplies the activity amount measuring section 1143 with a measurement instruction with a timing corresponding to a measuring mode to which a change has been made in accordance with the mode change command. This causes the activity amount measuring section 1143 to carry out activity amount measurement. The measuring mode control section 1141 also supplies the transfer data generating section 1142 with a transfer instruction with the timing corresponding to the measuring mode to which the change has been made in accordance with the mode change command. This causes the transfer data generating section 1142 to generate transfer data. The measuring mode control section 1141 also supplies the storage section capacity monitoring section 1144 with a judgment instruction with the timing corresponding to the measuring mode to which the change has been made in accordance with the mode change command. This causes the storage section capacity monitoring section 1144 to judge an available space. Note that the following timings in each of the measuring modes will be described later with reference to other drawings: (i) a timing with which to measure an activity amount measurement, (ii) a timing with which to transmit activity amount information, and a timing with which to judge an available space.

As illustrated in FIG. 10, the mobile device 1020 includes a communication section (transmitting section) 1201, an operation section 1202, a display section 1203, and a control section 1204.

The communication section 1201 communicates with the activity meter 1010 via short-distance wireless communication. Specifically, the communication section 1201 receives activity amount information from the activity meter 1010. The communication section 1201 also transmits a mode change command to the activity meter 1010.

The operation section 1202 receives a user operation. The operation section 1202 supplies, to the control section 1204, operation information which indicates a user operation. The operation section 1202 can be a touch sensor incorporated into the display section 1203 (touch panel), or can be a hardware key such as a button and a switch.

The display section 1203 displays information which has been obtained from the control section 1204. The display section 1203 can be configured by a transmissive liquid crystal panel having a backlight. Note, however, that the display section 1203 is not limited as such, but can be of other types such as an organic EL display. Alternatively, the display section 1203 can be a section that simply displays the information by turning on and off a light-emitting element such as an LED.

The control section 1204 comprehensively controls the sections of the mobile device 1020. The control section 1204 is configured by, for example, a CPU (central processing unit) or the like. As illustrated in FIG. 10, the control section 1204 also includes a display control section 1241 and a measuring mode instructing section 1242.

The display control section 1241 controls the display section 1203 to display information obtained. Specifically, the display control section 1241 controls the display section 1203 to display an activity amount which is indicated by the activity amount information obtained from the communication section 1201.

The measuring mode instructing section 1242 obtains the operation information from the operation section 1202. In a case where the operation information thus obtained indicates a specific user operation, the measuring mode instructing section 1242 supplies a mode change command to the communication section 1201.

(Process of Activity Meter 1010)

FIG. 12 is a flow chart illustrating a flow of a high frequency measuring mode process from a start to an end of a high frequency measuring mode, which process is carried out by the activity meter 1010 included in the activity amount measuring system 1001 of Embodiment 4. In the example of FIG. 12, a second period, during which the activity meter 1010 measures an activity amount in the high frequency measuring mode, is t seconds.

The measuring mode control section 1141 first judges whether or not the communication section 1101 has received, from the mobile device 1020, a mode change command which instructs a change in measuring mode to the high frequency measuring mode, that is, whether or not the communication section 1101 has received an instruction to start the high frequency measuring mode (Step S1001).

In a case where it is judged in the step S1001 that "an instruction to start the high frequency measuring mode has not been received" (Step S1001: No), the high frequency measuring mode process returns to the step S1001 so as to continue a process of judging whether or not the instruction to start the high frequency measuring mode has been received.

In a case where it is judged in the step S1001 that "the instruction to start the high frequency measuring mode has been received" (Step S1001: Yes), the measuring mode control section 1141 (i) supplies, to the timekeeping section 1102, time information indicative of a second period of t seconds and time information indicative of a 3-hour timeout and then (ii) starts the high frequency measuring mode (Step S1002).

Next, the measuring mode control section 1141 judges whether or not the measuring mode control section 1141 has obtained, from the timekeeping section 1102, a notification that t seconds have passed, that is, whether or not t seconds have passed (Step S1003).

In a case where it is judged in the step S1003 that "t seconds have passed" (Step S1003: Yes), the measuring mode control section 1141 supplies a measurement instruction to the activity amount measuring section 1143. In a case where the activity amount measuring section 1143 has obtained the measurement instruction, the activity amount measuring section 1143 measures a most recent activity based on sensor information which is among the sensor information stored in the storage section 1105 and which has not been referred to for measuring the activity amount. Then, the measuring mode control section 1141 records the thus measured activity amount information in the storage section 1105 (Step S1004).

Then, the measuring mode control section 1141 supplies a transfer instruction to the transfer data generating section 1142. In a case where the transfer data generating section 1142 has obtained the transfer instruction, the transfer data generating section 1142 (i) obtains, from the storage section 1105, activity amount information which is among data recorded in the storage section 1105 and which has not been transmitted to the mobile device 1020 and (ii) supplies the activity amount information to the communication section 1101. Then, the communication section 1101 transfers the activity amount information to the mobile device 1020 (Step S1005).

On the other hand, in a case where it is judged in the step S1003 that "t seconds have not passed" (Step S1003: No) and where a process in the step S1005 has been carried out, the measuring mode control section 1141 judges whether or not the measuring mode control section 1141 has obtained, from the timekeeping section 1102, a notification that 3 hours have passed, that is, whether or not a 3-hour timeout has occurred since the high frequency measuring mode was started (Step S1006).

In a case where it is judged in the step S1006 that "timeout has not occurred" (Step S1006: No), the measuring mode control section 1141 judges whether or not the communication section 1101 has received, from the mobile device 1020, a mode change command which instructs a change in measuring mode to a normal mode, that is, whether or not the communication section 1101 has received an instruction to end the high frequency measuring mode (Step S1007).

In a case where it is judged in the step S1007 that "the instruction to end the high frequency measuring mode has not been received" (Step S1007: No), the frequency measuring mode process returns to the step S1003 in which to judge whether or not t seconds have passed, so that the measuring mode control section 1141 continues the high frequency measuring mode.

On the other hand, in a case where it is judged in the step S1007 that "the instruction to end the high frequency measuring mode has been received" (Step S1007: Yes) and where it is judged in the step S1006 that "timeout has occurred" (Step S1006: Yes), the measuring mode control section 1141 (i) supplies, to the timekeeping section 1102, an end signal that ends the judging of whether or not t seconds have passed and whether or not 3 hours have passed and then (ii) ends the high frequency measuring mode (Step S1008).

Then, the measuring mode control section 1141 controls the activity amount measuring section 1143 to measure, in a manner similar to that described above, an activity amount of sensor information which was recorded during a period between (i) a time point at which a most recent activity amount measurement was carried out before the high frequency measuring mode was ended and (ii) a time point at which the high frequency measuring mode was ended. That is, the measuring mode control section 1141 controls the activity amount measuring section 1143 to measure an activity amount which has not been measured. Then, in order to transfer information on the measured activity amount to the mobile device 1020, the measuring mode control section 1141 controls the transfer data generating section 1142 to transfer, to the mobile device 1020, an activity amount information which has not been transferred (Step S1009).

Note that the activity amount information transferred to the mobile device 1020 is received by the communication section 1201. Then, the communication section 1201 supplies, to the display control section 1241, the activity amount information thus received. Then, the display control section 1241 controls the display section 1203 to display an activity amount which is indicated by the activity amount information thus received. This allows a user to confirm, by use of the mobile device 1020, an activity amount which has been measured by the activity meter 1010.

According to the activity amount measuring system 1001 of Embodiment 4, a mode change command, which is a command that instructs a change in a measuring mode, is thus transmitted from the mobile device 1020 to the activity meter 1010. Then, in a case where the activity meter 100 has received the mode change command, the activity meter 1010 changes the measuring mode for measuring the activity amount. This allows the user to change the measuring mode by operating only the mobile device 1020, and therefore prevents the user from being bothered by having to operate the activity meter 1010. In addition, since it is possible to easily end a high frequency measuring mode in which an increased number of activity amount measurements causes an increase in electric power consumption of the activity meter 1010, it is possible to restrict excess electric power consumption. Furthermore, since the activity meter 1010 transfers an activity amount to the mobile device 1020 every time an activity amount is measured, it is unnecessary to record a measured activity amount in the storage section 1105 even if the number of activity amount measurements is increased as a result of an operation in the high frequency measuring mode. This allows a capacity of the storage section 1105 to be small.

Embodiment 5

Figure 13:
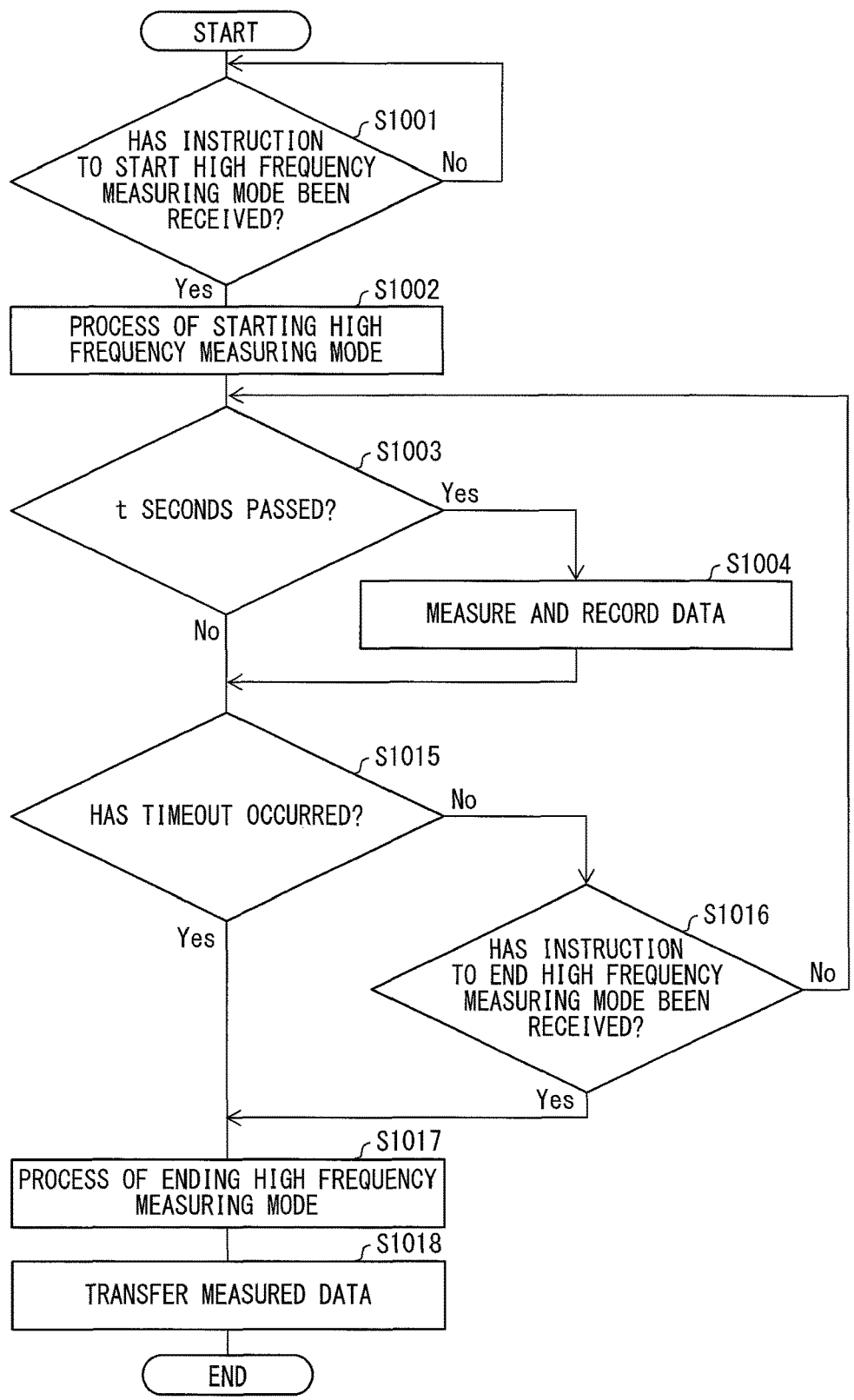
FIG. 13 is a flow chart illustrating a flow of a process from a start to an end of a high frequency measuring mode, which process is carried out by an activity meter included in an activity amount measuring system of Embodiment 5.

The following description will discuss Embodiment 5 of the present invention with respect to FIG. 13. Note that a configuration of an activity amount measuring system 1001 according to Embodiment 5 is similar to the configuration of the activity amount measuring system 1001 according to Embodiment 4 (see FIG. 10), and therefore will not be described.

FIG. 13 is a flow chart illustrating a flow of a high frequency measuring mode process from a start to an end of a high frequency measuring mode, which process is carried out by an activity meter 1010 included in the activity amount measuring system 1001 of Embodiment 5. In Embodiment 4, the activity meter 1010 transmits activity amount information to the mobile device 1020 every time an activity amount is measured in the high frequency measuring mode. According to this configuration, however, a frequency, with which the activity meter 1010 transmits activity amount information to the mobile device 1020, becomes high. This causes a load of the process to be heavy. Therefore, the activity amount measuring system 1001 of Embodiment 5 is configured so that when the activity meter 1010 ends a high frequency measuring mode, that is, after the activity meter 1010 has received a mode change command (second command) that instructs a change in intervals at which to measure an activity amount, from a second period to a first period, the activity meter 1010 collectively transmits, to a mobile device 1020, pieces of activity amount information on respective active amounts measured in the high frequency measuring mode.

First, the following process of Embodiment 5 is identical to that of Embodiment 4, and therefore will not be described in detail: A process which (i) starts from a step S1001 in which a measuring mode control section 1141 judges whether or not a communication section 1101 has received an instruction (first command) to start the high frequency measuring mode and (ii) ends in a step S1004 in which the activity amount measuring section 1143 measures and records an activity amount in a case where it is judged that t seconds have passed during a step S1003 in which it is judged whether or not t seconds have passed.

In a case where it is judged in the step S1003 that "t seconds have not passed" (Step S1003: No) and where a process in the step S1004 has been carried out, the measuring mode control section 1141 judges whether or not the measuring mode control section 1141 has obtained, from the timekeeping section 1102, a notification that 3 hours have passed, that is, whether or not a 3-hour timeout has occurred since the high frequency measuring mode was started (Step S1015).

In a case where it is judged in the step S1015 that "timeout has not occurred" (Step S1015: No), the measuring mode control section 1141 judges whether or not the communication section 1101 has received, from the mobile device 1020, a mode change command (second command) which is an instruction to end the high frequency measuring mode (Step S1016).

In a case where it is judged in the step S1016 that "the instruction to end the high frequency measuring mode has not been received" (Step S1016: No), the frequency measuring mode process returns to the step S1003 in which to judge whether or not t seconds have passed, so that the measuring mode control section 1141 continues the high frequency measuring mode.

On the other hand, in a case where it is judged in the step S1016 that "the instruction to end the high frequency measuring mode has been received" (Step S1016: Yes) and where it is judged in the step S1015 that "timeout has occurred" (Step S1015: Yes), the measuring mode control section 1141 (i) supplies, to the timekeeping section 1102, an end signal that ends the judging of whether or not t seconds have passed and whether or not 3 hours have passed and then (ii) ends the high frequency measuring mode (Step S1017).

Then, the measuring mode control section 1141 supplies a transfer instruction to a transfer data generating section 1142 so as to transfer activity amounts which have been measured in the high frequency measuring mode. In a case where the transfer data generating section 1142 has obtained the transfer instruction, the measuring mode control section 1141 (i) obtains, from the storage section 1105, activity amount information which is among data recorded in the storage section 1105 and which has not been transmitted to the mobile device 1020, that is, the activity amount information measure in the high frequency measuring mode and (ii) supplies the activity amount information to the communication section 1101. Then, the communication section 1101 transfers the activity amount information to the mobile device 1020 (Step S1018).

According to the activity amount measuring system 1001 of Embodiment 5, measured activity amounts are collectively transferred to the mobile device 1020 when the high frequency measuring mode ends. This causes the activity meter 1010 carry out transfer once, and therefore allows a load of the process of the activity meter 1010 to be lighter than that in Embodiment 4.

Embodiment 6

Figure 14:
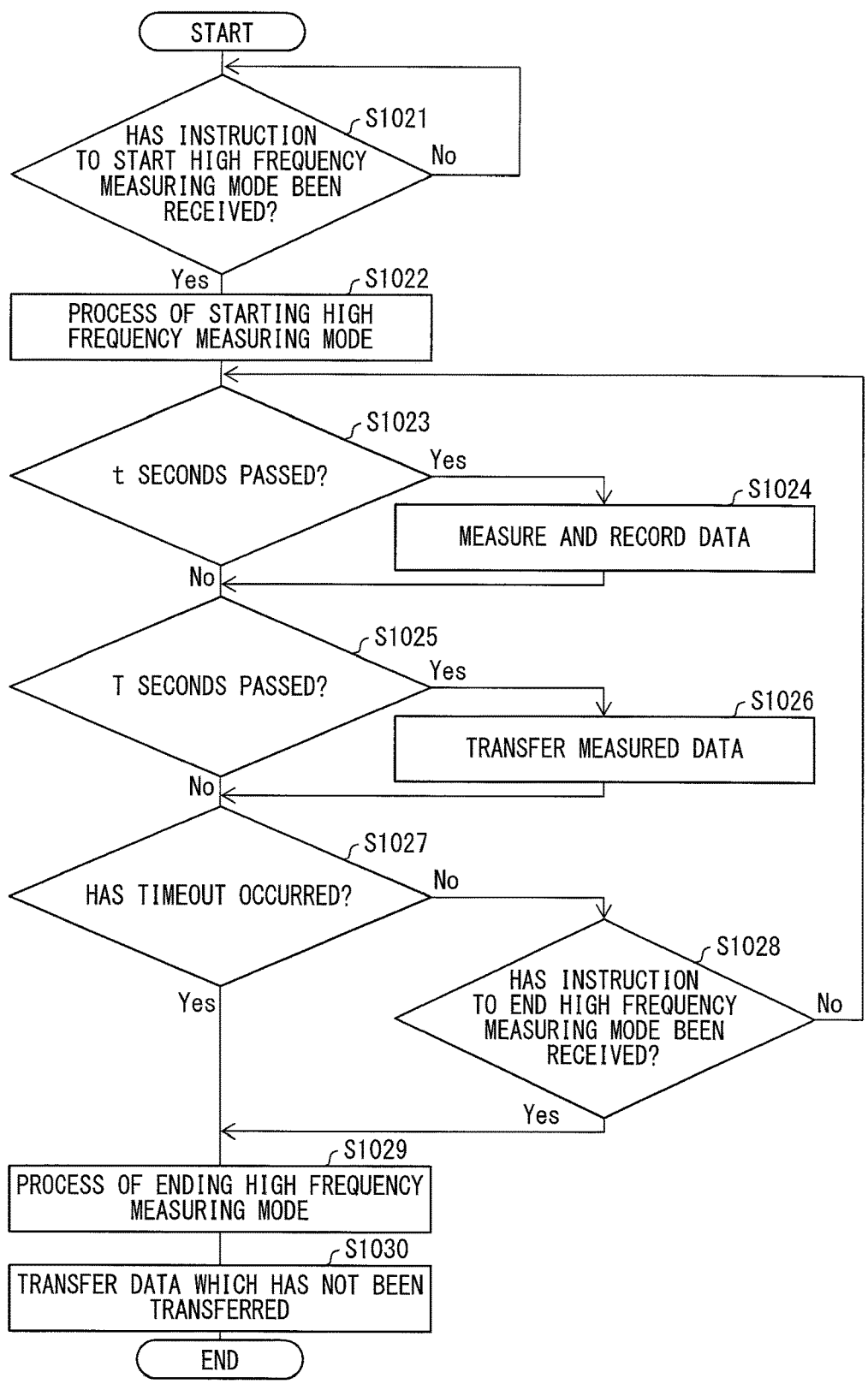
FIG. 14 is a flow chart illustrating a flow of a process from a start to an end of a high frequency measuring mode, which process is carried out by an activity meter included in an activity amount measuring system of Embodiment 6.

The following description will discuss Embodiment 6 of the present invention with reference to FIG. 14. Note that a configuration of an activity amount measuring system 1001 according to Embodiment 6 is similar to the configuration of the activity amount measuring system 1001 according to Embodiment 4 (see FIG. 10), and therefore will not be described.

FIG. 14 is a flow chart illustrating a flow of a high frequency measuring mode process from a start to an end of a high frequency measuring mode, which process is carried out by an activity meter 1010 included in the activity amount measuring system 1001 of Embodiment 6. In Embodiment 5, in order to cause the activity meter 1010 and the mobile device 1020 to communicate less frequently, the activity meter 1010 collectively transmits, to the mobile device 1020, pieces of activity amount information on respective activity amounts measured in the high frequency measuring mode when the high frequency measuring mode ends. According to this configuration, however, it is necessary to enlarge the capacity of the storage section 1105 in which the activity amount information is to be recorded. Therefore, in Embodiment 6, the activity meter 1010 transfers, in a high frequency measuring mode, measured activity amount information to the mobile device 1020 every period of T seconds which is longer than a second period of t seconds during each of which an activity amount is measured.

First, a measuring mode control section 1141 judges whether or not a communication section 1101 has received an instruction to start the high frequency measuring mode (Step S1021). In a case where it is judged in the step S1021 that "the instruction to start the high frequency measuring mode has not been received" (Step S1021: No), the frequency measuring mode process returns to the step S1021 so as to continue the process of judging whether or not the instruction to start the high frequency measuring mode has been received.

In a case where it is judged in the step S1021 that "the instruction to start the high frequency measuring mode has been received" (Step S1021: Yes), the measuring mode control section 1141 (i) supplies, to the timekeeping section 1102, time information indicative of a second period of t seconds, time information indicative of a 3-hour timeout, and time information indicative of a period of T seconds at which a measured activity amount is to be transferred and then (ii) starts the high frequency measuring mode (Step S1022).

Then, the measuring mode control section 1141 judges whether or not the t seconds have passed (Step S1023).

In a case where it is judged in the step S1023 that "t seconds have passed" (Step S1023: Yes), the measuring mode control section 1141 supplies a measurement instruction to an activity amount measuring section 1143. In a case where the activity amount measuring section 1143 received the measurement instruction, the activity amount measuring section 1143 (i) obtains sensor information which is among sensor information recorded in a storage section 1105 and which has not been measured and (ii) measures an activity amount. Then, the activity amount measuring section 1143 records, in the storage section 1105, activity amount information which indicates the activity amount thus measured (Step S1024).

On the other hand, in a case where it is judged in the step S1023 that "t seconds have not passed" (Step S1023: No) and where a process in a step S1024 has been carried out, the measuring mode control section 1141 judges whether or not the measuring mode control section 1141 has obtained, from the timekeeping section 1102, a notification that T seconds have passed, that is, the measuring mode control section 1141 judges whether or not T seconds have passed (Step S1025)

In a case where it is judged in the step S1025 that "T seconds have passed" (Step S1025: Yes), the measuring mode control section 1141 supplies, to a transfer data generating section 1142, a transfer instruction so that the activity amount information is transferred. In a case where the transfer data generating section 1142 has obtained the transfer instruction, the transfer data generating section 1142 (i) obtains, from the storage section 1105, activity amount information which is among data recorded in the storage section 1105 and which has not been transmitted and then (ii) supplies the activity amount information to the communication section 1101. Then, the communication section 1101 transfers, to the mobile device 1020, the activity amount information thus obtained (Step S1026).

On the other hand, in a case where it is judged in the step S1025 that "T seconds have not passed" (Step S1025: No) and where a process in the step S1026 has been carried out, the measuring mode control section 1141 judges whether or not the measuring mode control section 1141 has obtained, from the timekeeping section 1102, a notification that 3 hours have passed, that is, whether or not a 3-hour timeout has occurred since the high frequency measuring mode was started (Step S1027).

In a case where it is judged in the step S1027 that "timeout has not occurred" (Step S1027: No), the measuring mode control section 1141 judges whether or not the communication section 1101 has received, from the mobile device 1020, an instruction to end the high frequency measuring mode has been received (Step S1028). In a case where it is judged in the step S1028 that "an instruction to end the high frequency measuring mode has not been received" (Step S1028: No), the frequency measuring mode process returns to the step S1023 in which to judge whether or not t seconds have passed, so that the measuring mode control section 1141 continues the high frequency measuring mode.

On the other hand, in a case where it is judged in the step S1028 that "the instruction to end the high frequency measuring mode has been received" (Step S1028: Yes) and where it is judged in the step S1027 that "timeout has occurred" (Step S1027: Yes), the measuring mode control section 1141 supplies, to the timekeeping section 1102, an end signal that ends the judging of whether or not t seconds have passed, whether or not 3 hours have passed, and whether or not T seconds have passed and then (ii) ends the high frequency measuring mode (Step S1029).

Then, the measuring mode control section 1141 controls the activity amount measuring section 1143 to measure, in a manner similar to that described above, an activity amount of sensor information which was recorded during a period between (i) a time point at which a most recent activity amount measurement was carried out before the high frequency measuring mode was ended and (ii) a time point at which the high frequency measuring mode was ended. That is, the measuring mode control section 1141 controls the activity amount measuring section 1143 to measure an activity amount which has not been measured. Then, in order to transfer information on the measured activity amount to the mobile device 1020, the measuring mode control section 1141 controls the transfer data generating section 1142 to transfer, to the mobile device 1020, an activity amount information which has not been transferred (Step S1030).

According to the activity amount measuring system 1001 of Embodiment 6, the activity meter 1010 thus transfers, in the high frequency measuring mode, measured activity amount information to the mobile device 1020 every period of T seconds which is longer than a second period of t seconds during each of which an activity amount is measured. This allows a load of the process of the activity meter 1010 to be lighter than that in Embodiment 4, and allows a capacity of the storage section 1105 to be smaller than that in Embodiment 5.

Embodiment 7

Figure 15:
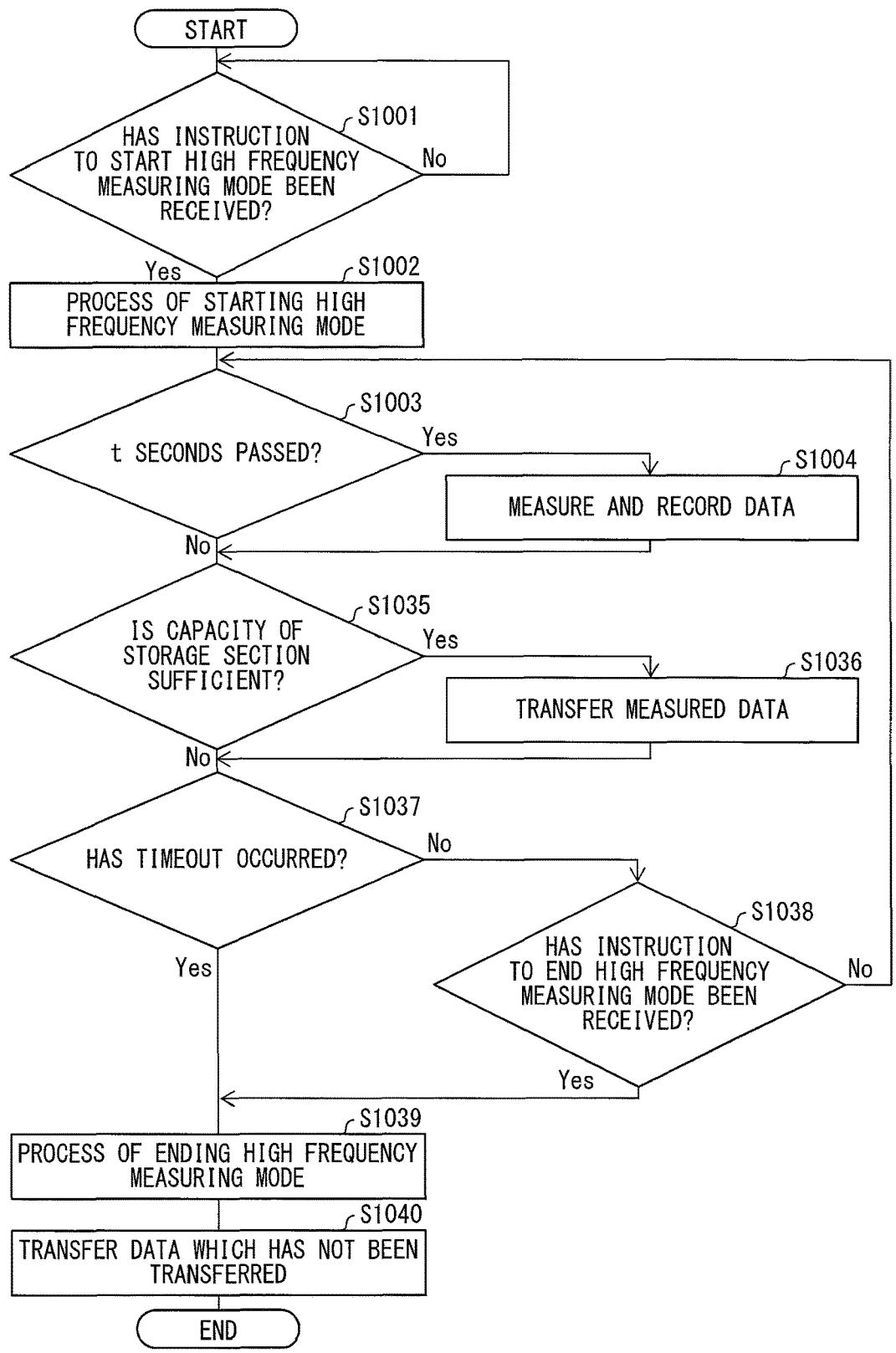
FIG. 15 is a flow chart illustrating a flow of a process from a start to an end of a high frequency measuring mode, which process is carried out by an activity meter included in an activity amount measuring system of Embodiment 7.

The following description will discuss Embodiment 7 of the present invention with reference to FIG. 15. Note that a configuration of an activity amount measuring system 1001 according to Embodiment 7 is similar to the configuration of the activity amount measuring system 1001 according to Embodiment 4 (see FIG. 10), and therefore will not be described.

FIG. 15 is a flow chart illustrating a flow of a high frequency measuring mode process from a start to an end of a high frequency measuring mode, which process is carried out by the activity meter 1010 included in the activity amount measuring system 1001 of Embodiment 7. In each of the above described embodiments, the activity meter 1010 transfers activity amount information to the mobile device 1020 with predetermined timings. In this configuration, however, an available space of the storage section 1105 is not taken into consideration in real time. This may cause a space for recording activity amount information, which indicates an activity amount measured, to be insufficient. Therefore, in Embodiment 7, in a case where an available space of a storage section 1105 is insufficient during a high frequency measuring mode, an activity meter 1010 transfers, to a mobile device 1020, activity amount information which indicates an activity amount measured.

First, the following process of Embodiment 5 is identical to that of Embodiment 4, and therefore will not be described in detail: A process which (i) starts from a step S1001 in which a measuring mode control section 1141 judges whether or not a communication section 1101 has received an instruction to start the high frequency measuring mode and (ii) ends in a step S1004 in which the activity amount measuring section 1143 measures and records an activity amount in a case where it is judged that t seconds have passed during a step S1003 in which it is judged whether or not t seconds have passed.

In a case where it is judged in the step S1003 that "t seconds have not passed" (Step S1003: No) and where a process in a step S1004 has been carried out, the measuring mode control section 1141 supplies a judgment instruction to a storage section capacity monitoring section 1144. In a case where the storage section capacity monitoring section 1144 has obtained the judgment instruction, the storage section capacity monitoring section 1144 judges whether or not a capacity of the storage section 1105 is sufficient (Step S1035).

In a case where it is judged in the step S1035 that "the capacity of the storage section 1105 is insufficient" (Step S1035: Yes), the measuring mode control section 1141 supplies a transfer instruction to a transfer data generating section 1142 for the purpose of freeing the capacity of the storage section 1105. In a case where the transfer data generating section 1142 has obtained the transfer instruction, the transfer data generating section 1142 (i) obtains, from the storage section 1105, activity amount information which is among data recorded in the storage section 1105 and which has not been transmitted and (ii) supplies the activity amount information to the communication section 1101. Then, the communication section 1101 transfers the activity amount information to the mobile device 1020 (Step S1036).

On the other hand, in a case where it is judged in the step S1035 that "the capacity of the storage section 1105 is sufficient" (Step S1035: No) and where a process in a step S1036 has been carried out, the measuring mode control section 1141 judges whether or not the measuring mode control section 1141 has obtained, from a timekeeping section 1102, a notification that 3 hours have passed, that is, whether or not a 3-hour timeout has occurred since the high frequency measuring mode was started (Step S1037).

In a case where it is judged in the step S1037 that "timeout has not occurred" (Step S1037: No), the measuring mode control section 1141 judges whether or not the communication section 1101 has received, from the mobile device 1020, an instruction to end the high frequency measuring mode has been received (Step S1038). In a case where it is judged in the step S1038 that "the instruction to end the high frequency measuring mode has not been received" (Step S1038: No), the frequency measuring mode process returns to the step S1003 in which to judge whether or not t seconds have passed, so that the measuring mode control section 1141 continues the high frequency measuring mode.

On the other hand, in a case where it is judged in the step S1038 that "the instruction to end the high frequency measuring mode has been received" (Step S1038: Yes) and where it is judged in the step S1037 that "timeout has occurred" (Step S1037: Yes), the measuring mode control section 1141 (i) supplies, to the timekeeping section 1102, an end signal that ends the judging of whether or not t seconds have passed and whether or not 3 hours have passed and then (ii) ends the high frequency measuring mode (Step S1039).

Then, the measuring mode control section 1141 controls the activity amount measuring section 1143 to measure, in a manner similar to that described above, an activity amount of sensor information which was recorded during a period between (i) a time point at which a most recent activity amount measurement was carried out before the high frequency measuring mode was ended and (ii) a time point at which the high frequency measuring mode was ended. That is, the measuring mode control section 1141 controls the activity amount measuring section 1143 to measure an activity amount which has not been measured. Then, in order to transfer information on the measured activity amount to the mobile device 1020, the measuring mode control section 1141 controls the transfer data generating section 1142 to transfer, to the mobile device 1020, an activity amount information which has not been transferred (Step S1040).

The activity amount measuring system 1001 of Embodiment 7 is thus configured so that in a case where an available space of the storage section 1105 is insufficient during the high frequency measuring mode, the activity meter 1010 transfers, to the mobile device 1020, activity amount information which indicates an activity amount measured. This prevents the activity meter 1010 from encountering a case where it is not possible to record, in the storage section, activity amount information which indicates an activity amount measured.

Embodiment 8

The following description will discuss Embodiment 8 of the present invention with reference to FIG. 16. Note that a configuration of an activity amount measuring system 1001 according to Embodiment 8 is similar to the configuration of the activity amount measuring system 1001 according to Embodiment 4 (see FIG. 10), and therefore will not be described.

(a) of FIG. 16 is a flow chart illustrating a flow of a frequency measuring mode process carried out at a start of a high frequency measuring mode, which process is carried out by an activity meter 1010 included in an activity amount measuring system 1001 according to Embodiment 8. (b) of FIG. 16 illustrates a table which shows relationships between mode numbers and corresponding measurement periods. The activity amount measuring system 1001 of Embodiment 8 is configured so that in a case where a mobile device 1020 transmits (i) an instruction to start a high frequency measuring mode and (ii) a mode number which is associated with a measurement period, the activity meter 1010 measures an activity amount by use of a value specified by the measurement period associated with the mode number. In a case where the mode number is 1 as illustrated in (b) of FIG. 16, intervals, at which the activity meter 1010 measures an activity amount, are of T1 (seconds). In a case where the mode number is 2 as illustrated in (b) of FIG. 16, the intervals are of T2 (seconds).

First, the measuring mode control section 1141 judges whether or not a communication section 1101 has received, from the mobile device 1020, (i) an instruction to start the high frequency measuring mode and (ii) a mode number (n) (Step S1041). In a case where it is judged in the step S1041 that "the instruction to start the high frequency measuring mode and the mode number (n) have not been received" (Step S1041: No), the frequency measuring mode process returns to the step S1041, so that the measuring mode control section 1141 continues the process of judging whether or not the instruction to start the high frequency measuring mode and the mode number (n) have been received.

In a case where it is judged in the step S1041 that "the instruction to start the high frequency measuring mode and the mode number (n) have been received" (Step S1041: Yes), the measuring mode control section 1141 judges the mode number thus received (Step S1042).

In a case where it is judged in the step S1042 that "mode number (n)=1", the measuring mode control section 1141 sets the measurement period to T1 (Step S1043).

In a case where it is judged in the step S1042 that "mode number (n)=2" the measuring mode control section 1141 sets the measurement period to T2 (Step S1044).

In a case where it is judged in the step S1042 that "mode number (n)=N", the measuring mode control section 1141 sets the measurement period to TN (Step S1045).

Then, the measuring mode control section 1141 decides the measurement period, and then starts the high frequency measuring mode (Step S1046).

The activity amount measuring system 1001 of Embodiment 8 is thus configured so that, in the high frequency measuring mode, the activity meter 1010 (i) receives, from the mobile device 1020, a mode number which is period information that specifies a value of each of periods during which the activity meter 1010 measures activity amounts and then (ii) measures the activity amounts during the periods. This allows periods of activity amount measurement carried out by the activity meter 1010 to be changed according to the types of activities. For example, it is possible to measure activity amounts every 5 minutes during jogging and measure activity amounts every 10 minutes during walking.

Embodiment 9

The following description will discuss Embodiment 9 of the present invention with reference to FIG. 17. Note that a configuration of an activity amount measuring system 1001 according to Embodiment 9 is similar to the configuration of the activity amount measuring system 1001 according to Embodiment 4 (see FIG. 10), and therefore will not be described.

FIG. 17 is a flow chart illustrating a flow of a frequency measuring mode process carried out at a start of a high frequency measuring mode, which process is carried out by an activity meter 1010 included in an activity amount measuring system 1001 according to Embodiment 9. In Embodiment 8, the activity meter 1010 changes a measurement period in response to reception of a mode number which is associated with the measurement period. However, there may not be a mode number set to correspond to a measurement period which is desirable to a user. Therefore, in Embodiment 9, (i) a mobile device 1020 transmits, to an activity meter 1010, measurement period information which specifies a value of a measurement period and then (ii) the activity meter 1010 measures the activity amount by use of the value of the measurement period specified by the measurement period information thus received. Note that in the following description, measurement period information, which specifies a measurement period tm, will be described as measurement period information (tm).

First, a measuring mode control section 1141 judges whether or not a communication section 1101 has received, from the mobile device 1020, (i) an instruction to start a high frequency measuring mode and (ii) measurement period information (tm) (Step S1051). In a case where it is judged in the step S1051 that "the instruction to start the high frequency measuring mode and the measurement period information (tm) have not been received" (Step S1051: No), the frequency measuring mode process returns to the step S1051, so that the measuring mode control section 1141 continues the process of judging whether or not the instruction to start the high frequency measuring mode and the measurement period information (tm) have been received.

On the other hand, in a case where it is judged that "the instruction to start the high frequency measuring mode and the measurement period information (tm) have been received (Step S1051: Yes), the measuring mode control section 1141 sets the measurement period to tm (Step S1052). Then, the measuring mode control section 1141 starts the high frequency measuring mode (Step S1053).

The activity amount measuring system 1001 of Embodiment 9 is thus configured so that (i) the mobile device 1020 transmits, to the activity meter 1010, measurement period information which specifies a value of a measurement period and then (ii) the activity meter 1010 measures the activity amount by use of the value of the measurement period specified by the measurement period information thus received. This allows the activity meter 1010 to measure activity amounts during specified measurement periods.

Embodiment 10

The following description will discuss, with reference to FIGS. 18 through 21, an embodiment of the information sharing system of the present invention. Note, however, that the configurations in this embodiment merely exemplify an embodiment of the present invention, and therefore should not be construed as limiting the scope of the invention only to them unless otherwise noted.

[Configuration of Information Sharing System]

First, the following description will discuss an information sharing system of Embodiment 10 with reference to FIG. 19. FIG. 19 is a view illustrating an appearance of an information sharing system 2001 according to Embodiment 10.

As illustrated in FIG. 19, the information sharing system 2001 includes an activity meter (activity amount measuring device) 2010, a mobile device 2020, and a server (information sharing support device) 2030. Moreover, as illustrated in FIG. 19, the information sharing system 2001 includes a plurality of activity meters 2010 and a plurality of mobile devices 2020. In FIG. 19, an activity meter 2010 and a mobile device 2020 which are possessed (used) by a user A are referred to as "activity meter 2010A" and "mobile device 2020A", respectively, and an activity meter 2010 and a mobile device 2020 which are possessed (used) by a user B are referred to as "activity meter 2010B" and "mobile device 2020B", respectively.

In Embodiment 10, the short-distance wireless communication between the activity meter 2010 and the mobile device 2020 is carried out by use of low-power-consumption short-distance wireless communication. Examples of the low-power-consumption short-distance wireless communication encompass Bluetooth (registered trademark) 4.0 (known as Bluetooth Low Energy) and ANT.

The activity meter 2010 measures an activity amount of a user and transmits activity amount information, which indicates the activity amount thus measured, to a server 2030 via the mobile device 2020.

In Embodiment 10, the activity meter 2010 is a wrist band-type activity meter which can be put on a wrist of a user as illustrated in FIG. 19. Note, however, that the a of the activity meter 2010 is not limited to a wrist band-type, provided that the activity meter 2010 can be put on the user's body, directly or indirectly. Examples of the activity meter 2010 encompass (i) a necklace-type activity meter which can be put on the user's neck and (ii) a clip-type activity meter which can be put on the user's body via clothing.

In Embodiment 10, the mobile device 2020 is a smartphone as illustrated in FIG. 19. Note, however, that the mobile device 2020 is not limited to a smartphone, provided that the mobile device 2020 is a portable information processing device. Examples of the mobile device 2020 encompass a mobile phone, a PDA (Personal Digital Assistant), and a tablet PC (Personal Computer).

The following description will schematically discuss, with reference to FIG. 18, configurations of the activity meter 2010, the mobile device 2020, and the server 2030 which are included in the information sharing system 2001 according to Embodiment 10. FIG. 18 is a block diagram illustrating configurations of the activity meter 2010, the mobile device 2020, and the server 2030 which are included in the information sharing system 2001 according to Embodiment 10.

[Activity Meter 2010]

The activity meter 2010 is a device for measuring an activity amount of a user who is wearing the activity meter 2010. As illustrated in FIG. 18, the activity meter 2010 includes a sensor section 2101, a timekeeping section 2102, a communication section (receiving section) 2103, a control section 2104, a storage section 2105, and a reporting section 2106.

Here, the activity amount indicates (i) a value obtained by quantifying information on movement of a user and (ii) information obtained from the value thus quantified. Examples of the activity amount encompass the number of steps, a consumed calorie, a walking distance, an exercise intensity (METs, Metabolic equivalents), an exercise (EX) quantity, an activity time (i.e., time of activity with a momentum of 3 METs or more), and the like.

(Sensor Section 2101)

The sensor section 2101 includes at least an acceleration sensor. The sensor section 2101 supplies, to the control section 2104, a sensor signal which indicates acceleration detected. In Embodiment 10, the sensor section 2101 includes a three-axis acceleration sensor. Alternatively, the sensor section 2101 can include a two-axis acceleration sensor or a one-axis acceleration sensor, instead of a three-axis acceleration sensor. Alternatively, the sensor section 2101 can include, in addition to an acceleration sensor, a gyrosensor, an altitude (atmospheric pressure) sensor, a temperature sensor, a humidity sensor, and/or the like. Referring to sensor signals supplied from these sensors, it is possible to more accurately calculate an activity amount which depends on a posture of a user and on a surrounding environment.

(Timekeeping Section 2102)

The timekeeping section 2102 is a timer for notifying the control section 2104 that an amount of time specified by the control section 2104 has passed. Specifically, the timekeeping section 2102 judges whether or not a predetermined time period has elapsed. In a case where the timekeeping section 2102 has determined that the predetermined time period has elapsed, the timekeeping section 2102 notifies the control section 2104 that the predetermined time period has elapsed. The timekeeping section 2102 repeatedly carries out a sequence of processes including (i) the judging of whether or not the predetermined time period has elapsed and (ii) the notifying of the fact that the predetermined time period has elapsed.

The predetermined time period is not limited to a particular one and can be, for example, 1 hour, 10 minutes, or 1 minute. Moreover, the predetermined time period can be arbitrarily set by the user. In this case, the predetermined time period can be set by operating an operation section (not illustrated) included in the activity meter 2010 or can be set by operating an operation section 2204 (later described) included in the mobile device 2020.

The timekeeping section 2102 can further include a clock. In this case, the timekeeping section 2102 can notify the control section 2104 of the time.

(Communication Section 2103)

The communication section 2103 communicates with the mobile device 2020 via short-distance wireless communication. The communication section 2103 (i) transmits, to the mobile device 2020, activity amount information which has been supplied from the control section 2104 and (ii) receives a reporting instruction transmitted from the mobile device 2020 (details of the activity amount information and the reporting instruction will be described later).

(Control Section 2104)

The control section 2104 comprehensively controls the sections of the activity meter 2010. The control section 2104 is configured by, for example, a CPU (central processing unit) or the like. The control section 2104 includes an activity amount calculating section 2141, and a report control section 2142 (see FIG. 18).

The activity amount calculating section 2141 included in the control section 2104 calculates information (activity amount information) which relates to an activity amount of the user by quantifying, based on a predetermined algorithm, a sensor signal supplied from the sensor section 2101.

Specifically, the activity amount calculating section 2141 quantifies a waveform signal (sensor signal) supplied from the sensor section 2101 and thus calculates, per unit time, activity amount information such as user's activity (at rest, walking, running, or the like) or the number of steps in walking. Note that the unit time is not limited to a particular one and can be, for example, 1 minute, 10 seconds, or 1 hour. The activity amount calculating section 2141 can calculate the activity amount information every time the activity amount calculating section 2141 is notified, by the timekeeping section 2102, that the unit time has elapsed.

The control section 2104 transmits the activity amount information which has been calculated by the activity amount calculating section 2141 to the mobile device 2020 via the communication section 2103. In this case, the control section 2104 can transmit the activity amount information to the mobile device 2020 every time the activity amount calculating section 2141 has calculated the activity amount information. Alternatively, the control section 2104 can carry out transmission of activity amount information to the mobile device 2020 at a time point at which a predetermined number of pieces of activity amount information have been accumulated in the storage section 2105.

In Embodiment 10, a configuration example is described in which the activity amount calculating section 2141 included in the control section 2104 calculates activity amount information based on a sensor signal supplied from the sensor section 2101. Note, however, that the present invention is not limited as such. For example, it is possible to employ a configuration in which the sensor section 2101 (i) includes an activity amount calculating section, (ii) calculates activity amount information by quantifying a sensor signal, and (iii) supplies the calculated activity amount information to the control section 2104.

The report control section 2142 included in the control section 2104 controls, based on a reporting instruction received from the mobile device 2020, a reporting operation carried out by the reporting section 2106. Examples of the reporting instruction encompass an instruction on making a report relating to an activity amount of a friend, an instruction on making a report relating to a cheer received from a friend, and the like. Note that details of the reporting operation carried out by the reporting section 2106 will be described later.

(Storage Section 2105)

The storage section 2105 stores data received by the communication section 2103, activity amount information calculated by the activity amount calculating section 2141 included in the control section 2104, and the like.

(Reporting Section 2106)

The reporting section 2106 carries out, in accordance with control by the report control section 2142 included in the control section 2104, reporting operations for making various reports to the user who uses the activity meter 2010.

The reporting section 2106 is not limited to a particular one and can be configured by at least any of a light-emitting section such as an LED (Light-Emitting Diode); a display section such as an LCD (Liquid Crystal Display); an audio output section such as a speaker; a vibrating section; and the like. In Embodiment 10, an example configuration is described in which the reporting section 2106 is configured by an LED and reports relating to a momentum of one friend, a cheer from a friend, and the like are made by one LED. Note, however, that, in a case where the reporting section 2106 is configured by a display section, one display section can make reports relating to momentums of a plurality of friends, cheers received from a plurality of friends, and the like.

[Mobile Device 2020]

The mobile device 2020 is a device which cooperates with the activity meter 2010 so as to measure an activity amount of the user. As illustrated in FIG. 18, the mobile device 2020 includes a communication section 2201, an auxiliary information obtaining section 2202, a control section 2203, an operation section 2204, and a storage section 2205. In Embodiment 10, an example is described in which the mobile device 2020 is configured by a smartphone. Note, however, that Embodiment 10 is not limited as such and it is possible to employ a configuration in which the mobile device 2020 is configured by a mobile phone, a tablet PC, or the like.

(Communication Section 2201)

The communication section 2201 communicates with the activity meter 2010 via short-distance wireless communication and communicates with the server 2030 via wireless communication. Note that the wireless communication between the communication section 2201 and the server 2030 is not limited to a particular one, provided that the wireless communication is carried out via a network such as the Internet.

(Auxiliary Information Obtaining Section 2202)

The auxiliary information obtaining section 2202 obtains subsidiary information (activity amount auxiliary information) which relates to an activity amount of the user. In Embodiment 10, the auxiliary information obtaining section 2202 can be configured by, for example, GPS (Global Positioning System). In this case, the auxiliary information obtaining section 2202 obtains, as activity amount auxiliary information, a latitudinal value and a longitudinal value of a location of the user.

The auxiliary information obtaining section 2202 supplies obtained activity amount auxiliary information to the control section 2203.

(Control Section 2203)

The control section 2203 comprehensively controls the sections of the mobile device 2020. The control section 2203 is configured by, for example, a CPU (central processing unit) or the like.

The control section 2203 transmits, to the activity meter 2010 via the communication section 2201, an instruction on carrying out a reporting operation. Note that the reporting instruction can be generated by the control section 2203 or notified by the server 2030, and is thus not limited in particular.

Moreover, the control section 2203 transmits, to the server 2030 via the communication section 2201, activity amount information of the user obtained from the activity meter 2010 and activity amount auxiliary information supplied from the auxiliary information obtaining section 2202. Specifically, the control section 2203 causes activity amount information and activity amount auxiliary information to be stored in the storage section 2205 and, each time a predetermined time period (e.g., 10 minutes) elapses, the control section 2203 transmits, to the server 2030, activity amount information and activity amount auxiliary information which have been stored in the storage section 2205 during the predetermined time period.

(Operation Section 2204)

The operation section 2204 accepts a user operation. The operation section 2204 is not limited to a particular one and can be configured by a plurality of physical buttons, a touch panel, or the like.

Examples of the user operation accepted by the operation section 2204 encompass an apparatus registering operation for registering, in the server 2030, a certain activity meter 2010 and a certain mobile device 2020 as an activity meter 2010 and a mobile device 2020 to be used by a certain user; an event registering operation for registering, in the server 2030, an event in which the user of the mobile device 2020 participates; and the like.

(Storage Section 2205)

The storage section 2205 is controlled by the control section 2203 to temporarily store user's activity amount information which has been obtained from the activity meter 2010 and activity amount auxiliary information which has been obtained by the auxiliary information obtaining section 2202.

[Server 2030]

The server 2030 is a device which integrally controls sharing of information regarding an activity amount of the user between a plurality of activity meters 2010 which are registered in the server 2030 (the registration and the sharing will be described later). As illustrated in FIG. 18, the server 2030 includes a communication section 2301, a control section 2302, and a management information storage section 2303. In Embodiment 10, an example is described in which the server 2030 is configured by one server. Note, however, that the present invention is not limited as such and the server 2030 can be configured by servers which are different in at least any of functions of the sections.

(Communication Section 2301)

The communication section 2301 wirelessly communicates with the mobile device 2020 via, for example, a network such as the Internet.

(Control Section 2302)

The control section 2302 comprehensively controls the sections included in the server 2030. The control section 2302 includes a sharing control section (reporting ability judging section) 2321, and a notification control section (generating section) 2322.

The sharing control section 2321 controls sharing of information between an activity meter 2010 used by a certain user and an activity meter 2010 used by another user. Note that, in this specification, the term "sharing" indicates that reporting of information, which relates to an activity amount of a certain user measured by an activity meter 2010 used by the certain user, is carried out with an activity meter 2010 used by another user.

The sharing control section 2321 judges whether or not information regarding an activity amount of a certain user measured by a certain activity meter 2010 can be reported with an activity meter 2010 used by another user (i.e., whether or not the information can be shared). Note that a judging method will be described later.

The notification control section 2322 generates a reporting instruction which (i) is on making a report in accordance with activity amount information supplied from a certain activity meter 2010 via the mobile device 2020 and (ii) is given to another activity meter 2010 which is different from the certain activity meter 2010. Moreover, the notification control section 2322 notifies an activity meter 2010, which has been determined by the sharing control section 2321 to be able to carry out a reporting operation, of a reporting instruction. Specifically, the notification control section 2322 transmits a reporting instruction to the mobile device 2020 via the communication section 2301, and the mobile device 2020 transmits the received reporting instruction to the activity meter 2010, and thus the activity meter 2010 is notified of the reporting instruction from the server 2030.

Note that the notification control section 2322 can generate a reporting instruction based on activity amount auxiliary information supplied from the mobile device 2020, instead of the activity amount information.

(Management Information Storage Section 2303)

The management information storage section 2303 is a storage section for storing various kinds of management information. As illustrated in FIG. 18, the management information storage section 2303 has a user registration information management region 2331, a friend registration information management region 2332, and a schedule information management region 2333.

In the user registration information management region 2331, information (i.e., user registration information) relating to a user using an activity meter 2010 is stored. Examples of the user registration information encompass personal information such as an age, a gender, a height, a weight, and a birth Date of the user; and information regarding a mobile device 2020 used by the user and an activity meter 2010 that is used with respect to the user.

For example, the user can register user registration information in the server 2030 by operating the operation section 2204 of the mobile device 2020 so that the mobile device 2020 used by the user and the activity meter 2010 are associated with each other in the server 2030. Moreover, the user can register, as user registration information, personal information such as an age, a gender, a height, a weight, and a birth Date of the user in the server 2030 by operating the operation section 2204 of the mobile device 2020.

Note that registration of the activity meter 2010 and the mobile device 2020, registration of the user's personal information, and the like can be carried out, for example, by executing, with the mobile device 2020, functions which relate to user registration and are included in an application provided from the server 2030.

In the friend registration information management region 2332, friend registration information regarding mutual friend registration of users is stored. Examples of the friend registration information encompass information which indicates that a certain user and another user are friends.

The friend registration information can be registered, for example, as follows: that is, a certain user operates the operation section 2204 of the mobile device 2020 so as to send, to another user, a request for registration as friends, and then the another user approves the request from the certain user. As such, the certain user and the another user are registered as friends. Note that registration of friends can be carried out, for example, by executing, with the mobile device 2020, functions which relate to friend registration and are included in an application provided from the server 2030.

The schedule information management region 2333 stores schedule information (schedule management information) such as information regarding an event in which the user participates and information regarding a plan of the user. Examples of the information regarding an event encompass a Date on which the event is held, a start time and an end time of the event, contents of the event, a place at which the event is held, a type of participation (e.g., participants, spectators, or the like) in the event. Examples of the information regarding a plan of the user encompass plans such as a work, a meal, going-out, and sleep, and a start time and an end time of each of such plans.

Note that registration of the schedule information can be carried out, for example, by executing, with the mobile device 2020, functions which relate to registration of schedule information and are included in an application provided from the server 2030.

[Sharing/Reporting Process]

The following description will discuss, with reference to FIGS. 20 and 21, a sharing/reporting process which is carried out by the information sharing system 2001 so that a certain activity meter 2010 carries out a reporting operation based on activity amount information which indicates an activity amount measured by another activity meter 2010. Note that the sharing/reporting process of Embodiment 10 encompasses processes such as (i) an exerciser information sharing/reporting process for reporting information on an exercising user (exerciser) to a user (spectator) who is watching the event and (ii) a spectator information sharing/reporting process for reporting information on a spectator to an exerciser.

In Embodiment 10, an example is described in which the event is a marathon, a user A is registered (i.e., participates) in the marathon as an exerciser (i.e., runner), and a user B is registered (i.e., watches the marathon) as a spectator.

(Exerciser Information Sharing/Reporting Process)

First, the following description will discuss the exerciser information sharing/reporting process with reference to FIG. 20. FIG. 20 is a sequence diagram illustrating the exerciser information sharing/reporting process carried out by the information sharing system 2001 in Embodiment 10.

As illustrated in FIG. 20, in a case where the marathon has begun, an activity meter 2010A which is used by the user A who has been registered as a participant obtains an activity amount of the user A which activity amount has been measured by the sensor section 2101 (activity amount measuring) (Step S2101). The control section 2104 of the activity meter 2010A (i) controls the activity amount calculating section 2141 to calculate activity amount information based on a sensor signal and then (ii) transmits the activity amount information thus calculated to the mobile device 2020B via the communication section 2103.

In a case where the mobile device 2020A has obtained the activity amount information of the user A from the activity meter 2010A, the auxiliary information obtaining section 2202 of the mobile device 2020A obtains activity amount auxiliary information such as a current location of the user A (auxiliary information obtaining) (Step S2102). The control section 2203 of the mobile device 2020A transmits, via the communication section 2201, the activity amount auxiliary information of the user A, which information has been obtained by the auxiliary information obtaining section 2202, to the server 2030 together with the activity amount information of the user A which information has been supplied from the activity meter 2010A.

Upon receipt of the activity amount information and the activity amount auxiliary information of the user A from the mobile device 2020A, the server 2030 judges whether or not a reporting operation can be carried out with the activity meter 2010B used by the user B (sharing ability judging process) (Step S2103). Specifically, first, the sharing control section 2321 included in the control section 2302 of the server 2030 specifies, with reference to schedule information stored in the schedule information management region 2333, an event (i.e., marathon in Embodiment 10) which is held at the time at which the activity amount information and the activity amount auxiliary information of the user A are obtained. Then, the sharing control section 2321 judges whether or not the event thus specified has been registered (as an event to be watched) in the schedule of the user B. In a case where the specified event has been registered, in the schedule of the user B, as an event to be watched, the sharing control section 2321 determines that the reporting operation can be carried out with the activity meter 2010B.

In a case where the sharing control section 2321 has determined that the reporting operation can be carried out with the activity meter 2010B, the notification control section 2322 included in the control section 2302 of the server 2030 transmits a reporting instruction to the activity meter 2010B via the mobile device 2020B. Specifically, the notification control section 2322 transmits a reporting instruction on carrying out the reporting operation with the activity meter 2010B to the mobile device 2020B via the communication section 2301. Then, the control section 2203 included in the mobile device 2020B transmits the reporting instruction, which has been obtained from the server 2030, to the activity meter 2010B via the communication section 2201 (Step S2104).

For example, based on the activity amount information of the user A, the server 2030 notifies, via the mobile device 2020B, the activity meter 2010B of an instruction on carrying out a reporting operation relating to a physical strength condition (e.g., fatigue degree) of the user A. Moreover, based on the activity amount auxiliary information of the user A, the mobile device 2020B notifies, via the mobile device 2020B, the activity meter 2010B of a reporting instruction on carrying out a reporting operation relating to a distance from the user A to a goal of a marathon course. Note that a method of judging a fatigue degree of the user A (runner) will be described later.

On the other hand, in a case where the server 2030 has determined that the reporting operation cannot be carried out with the activity meter 2010B (i.e., in a case where the user B is not registered as a spectator of the marathon event), no reporting instruction is transmitted.

The activity meter 2010B carries out a reporting operation in accordance with the reporting instruction which has been obtained from the server 2030 via the mobile device 2020B (Step S2105).

In Embodiment 10, a configuration example is described in which a reporting instruction based on activity amount information and activity amount auxiliary information of the user A is transmitted from the server 2030 to the activity meter 2010B via the mobile device 2020B. Note, however, that the present invention is not limited as such. For example, it is possible to employ a configuration in which the mobile device 2020B transmits, to the activity meter 2010B, a reporting instruction that is based on activity amount information and activity amount auxiliary information of the user A which have been obtained from the server 2030. Alternatively, it is possible to employ a configuration in which the activity meter 2010B carries out a reporting operation based on activity amount information and activity amount auxiliary information of the user A which have been obtained from the mobile device 2020B.

(Method of Judging Fatigue Degree of Runner)

Here, the following description will discuss an example of a method of judging a fatigue degree of the user A (runner). Note that, in Embodiment 10, the fatigue degree of the runner is classified into a normal state, a fatigue state, and a danger state.

Note that, in this specification, the fatigue degree of "normal state" means a state in which the runner is not suffering from fatigue, i.e., a state in which the runner is not tired. The fatigue degree of "fatigue state" means a state in which the runner is suffering from fatigue, i.e., a state in which the runner is tired. The fatigue degree of "danger state" means a state in which the runner is extremely suffering from fatigue, i.e., a state in which the runner is extremely tired.

For example, in a case where a waveform of a sensor signal supplied by the acceleration sensor included in the sensor section 2101 indicates "standard running pace", the activity amount calculating section 2141 included in the control section 2104 of the activity meter 2010A can determine that the fatigue degree of the user A is the normal state. In a case where a moving speed which is at a location of the user A and is obtained by the auxiliary information obtaining section 2202 per predetermined time indicates "standard running pace", the control section 2203 included in the mobile device 2020A can determine that the fatigue degree of the user A is the normal state. In a case where a moving speed of the user A with respect to a total distance of the marathon course indicates "standard running pace", the control section 2302 included in the server 2030 can also determine that the fatigue degree of the user A is the normal state.

In a case where a waveform of a sensor signal supplied by the acceleration sensor included in the sensor section 2101 indicates "slower than standard running pace", the activity amount calculating section 2141 included in the control section 2104 of the activity meter 2010A can determine that the fatigue degree of the user A is the fatigue state. In a case where a moving speed which is at a location of the user A and is obtained by the auxiliary information obtaining section 2202 per predetermined time indicates "slower than standard running pace", the control section 2203 included in the mobile device 2020A can determine that the fatigue degree of the user A is the fatigue state. In a case where a moving speed of the user A with respect to a total distance of the marathon course indicates "slower than standard running pace", the control section 2302 included in the server 2030 can also determine that the fatigue degree of the user A is the fatigue state.

In a case where a waveform of a sensor signal supplied by the acceleration sensor included in the sensor section 2101 indicates "considerably slower than standard running pace", the activity amount calculating section 2141 included in the control section 2104 of the activity meter 2010A can determine that the fatigue degree of the user A is the danger state. In a case where a moving speed which is at a location of the user A and is obtained by the auxiliary information obtaining section 2202 per predetermined time indicates "considerably slower than standard running pace", the control section 2203 included in the mobile device 2020A can determine that the fatigue degree of the user A is the danger state. In a case where a moving speed of the user A with respect to a total distance of the marathon course indicates "considerably slower than standard running pace", the control section 2302 included in the server 2030 can also determine that the fatigue degree of the user A is the danger state.

In Embodiment 10, configuration examples are described in which (i) the activity meter 2010A judges the fatigue degree of the user based on a waveform of a sensor signal, (ii) the mobile device 2020A judges the fatigue degree of the user based on a moving speed of the runner, and (iii) the server 2030 judges the fatigue degree of the user based on a lap time. Note, however, that the present invention is not limited to these. For example, it is possible to employ a configuration in which the server 2030 judges a fatigue degree of a runner based on a moving speed of the runner which speed has been calculated from (i) a waveform of a sensor signal obtained from the activity meter 2010A or (ii) location information of the runner which information has been obtained from the mobile device 2020A.

In the above example, the configuration is described in which the fatigue degree of the runner is classified into the normal state, the fatigue state, and the danger state. Note, however, that the present invention is not limited as such. For example, it is possible to employ a configuration in which the fatigue degree of the runner includes a state in which the runner is cheating (cheating state) and a state in which the runner is out of the marathon course (loitering state).

With the configuration, for example, in a case where a waveform of a sensor signal supplied from the acceleration sensor provided in the sensor section 2101 of the activity meter 2010A does not indicate a state of running (e.g., in a case where the waveform indicates a state of riding a bicycle), it is possible to determine that the fatigue degree is the cheating state.

(Reporting Operation Carried Out by Activity Meter Used by Spectator)

Next, the following description will discuss an example of a reporting operation that is carried out by the reporting section 2106 included in the activity meter 2010B according to Embodiment 10.

In a case where the report control section 2142 included in the control section 2104 of the activity meter 2010B has been notified of a reporting instruction from the server 2030 via the mobile device 2020B, the report control section 2142 controls, in accordance with the reporting instruction, the reporting section 2106 to carry out a reporting operation.

Here, in a case where the reporting instruction thus notified is a reporting instruction on carrying out a reporting operation relating to the fatigue degree of the user A, the report control section 2142 controls the reporting section 2106 to carry out a reporting operation of reporting the fatigue degree of the user A to the user B.

For example, in a case where the fatigue degree of the user A is the normal state, the report control section 2142 can control an LED of the reporting section 2106 to emit green light; in a case where the fatigue degree of the user A is the fatigue state, the report control section 2142 can control the LED to emit yellow light; and in a case where the fatigue degree of the user A is the danger state, the report control section 2142 can control the LED to emit red light. In a case where the user A is in the cheating state, the report control section 2142 can control the LED to sequentially emit red light, green light, and blue light. In a case where the user A is in the loitering state, the report control section 2142 can control the LED to sequentially emit red light, yellow light, green light, and blue light.

In a case where the notified reporting instruction is a reporting instruction on carrying out a reporting operation relating to a distance from the user A to the goal of the marathon course, the report control section 2142 controls the reporting section 2106 to carry out a reporting operation of reporting, to the user B, information which relates to a distance from the user A to the goal.

For example, the report control section 2142 can control the LED included in the reporting section 2106 to emit light such that green light becomes brighter as the distance from the user A to the goal becomes shorter.

In a case where the notified reporting instruction is a reporting instruction on carrying out a reporting operation of presenting a response from the user A to a cheer given from a spectator (later described), the report control section 2142 carries out the reporting operation relating to the response from the user A.

Note that the reporting instruction on presenting a response from the user A to a cheer given from a spectator is sent from the server 2030 to the activity meter 2010B in a case where, for example, the activity meter 2010A has obtained an activity amount which relates to an action (gesture) (hereinafter, also referred to as "response action") of indicating a response from the user A to the cheer given from the spectator. The response action can be, for example, an action of turning the arm round and round.

In the above described example, the reporting section 2106 includes only one LED for carrying out a reporting operation relating to the user A. Note, however, that the present invention is not limited as such example. For example, in a case where the reporting section 2106 includes a plurality of LEDs for carrying out a reporting operation relating to the user A, it is possible to simultaneously report the fatigue degree of the user A, the distance to the goal, and the response to the cheer with respective different LEDs.

(Spectator Information Sharing/Reporting Process)

Next, the following description will discuss the spectator information sharing/reporting process with reference to FIG. 21. FIG. 21 is a sequence diagram illustrating a flow of the spectator information sharing/reporting process carried out by the information sharing system 2001 according to Embodiment 10.

As illustrated in FIG. 21, in a case where the marathon has begun, the activity meter 2010B which is used by the user B registered as a spectator obtains an activity amount which relates to an action (gesture) (hereinafter, also referred to as "cheering action") which indicates a cheer from the user B to the user A (cheering action detection) (Step S2201). Examples of the cheering action encompass an action of swinging the arm up and down, an action of swinging the arm right and left, and the like. In Embodiment 10, an action of strongly swinging the arm up and down which action means "hang in there" is carried out as a cheering action. The activity amount calculating section 2141 included in the control section 2104 of the activity meter 2010B (i) calculates activity amount information of cheering action (also referred to as cheering activity amount information) based on a sensor signal which indicates cheering action and has been supplied from the acceleration sensor included in the sensor section 2101 and (ii) transmits the cheering activity amount information thus calculated to the mobile device 2020A via the communication section 2103.

The mobile device 2020B which has obtained the cheering activity amount information of the user B from the activity meter 2010B transmits the cheering activity amount information thus obtained to the server 2030.

In a case where the sharing control section 2321 of the server 2030 has obtained the cheering activity amount information of the user B from the mobile device 2020B, the sharing control section 2321 judges whether or not a reporting operation can be carried out with the activity meter 2010A used by the user A at the time at which the sharing control section 2321 obtained the cheering activity amount information (sharing ability judging process) (Step S2202).

In a case where the sharing control section 2321 has determined that the reporting operation can be carried out with the activity meter 2010A, the notification control section 2322 included in the control section 2302 of the server 2030 transmits a reporting instruction to the activity meter 2010A via the mobile device 2020A. Specifically, the notification control section 2322 transmits a reporting instruction on carrying out the reporting operation with the activity meter 2010A to the mobile device 2020A via the communication section 2301. Then, the control section 2203 included in the mobile device 2020A transmits the reporting instruction, which has been obtained from the server 2030, to the activity meter 2010A via the communication section 2201 (Step S2203).

In a case where, for example, the cheering activity amount information of the user B indicates an action of strongly swinging the arm up and down, the server 2030 can transmit a reporting instruction for causing the activity meter 2010A to carry out a reporting operation for representing "hang in there".

On the other hand, in a case where the server 2030 has determined that the reporting operation cannot be carried out with the activity meter 2010A (i.e., in a case where the user A is not registered as a participant of the marathon event), no reporting instruction is transmitted.

The activity meter 2010A carries out a reporting operation in accordance with the reporting instruction which has been obtained from the server 2030 via the mobile device 2020A (Step S2204).

In Embodiment 10, a configuration example is described in which a reporting instruction based on cheering activity amount information of the user B is transmitted from the server 2030 to the activity meter 2010A via the mobile device 2020A. Note, however, that the present invention is not limited as such. For example, it is possible to employ a configuration in which the mobile device 2020A transmits, to the activity meter 2010A, a reporting instruction based on cheering activity amount information of the user B which information has been obtained from the server 2030. Alternatively, it is possible to employ a configuration in which the activity meter 2010A carries out a reporting operation based on cheering activity amount information of the user B which information has been obtained from the mobile device 2020A.

(Reporting Operation Carried Out by Activity Meter Used by Exerciser)

Next, the following description will discuss an example of a reporting operation that is carried out by the reporting section 2106 included in the activity meter 2010A according to Embodiment 10.

In a case where the report control section 2142 included in the control section 2104 of the activity meter 2010A has been notified of a reporting instruction from the server 2030 via the mobile device 2020A, the report control section 2142 controls, in accordance with the reporting instruction, the reporting section 2106 to carry out a reporting operation.

Here, in a case where the reporting instruction thus notified is a reporting instruction on carrying out a reporting operation relating to cheering by the user B, the report control section 2142 controls the reporting section 2106 to carry out a reporting operation of representing content of cheer given from the user B. For example, the report control section 2142 can control the reporting section 2106 to blink blue light of the LED so as to carry out a reporting operation of representing that the content of cheer given from the user B is "hang in there".

In Embodiment 10, an example is described in which the reporting section 2106 is configured by the LED. Note, however, that the present invention is not limited as such. For example, it is possible to employ a configuration in which the reporting section 2106 includes a vibrating section in addition to the LED. In this case, the report control section 2142 of the activity meter 2010A can control the vibrating section included in the reporting section 2106 to vibrate so as to report the cheer given from the user B. With this, the user A can recognize, by the vibration, the report relating to the cheer given from the user B, without confirming light emitted by the LED provided as the reporting section 2106 of the activity meter 2010A.

Further, it is possible to carry out, with the reporting section 2106 of the activity meter 2010A used by the user A who is the exerciser, (i) reporting of the number of spectators (spectator number) and (ii) reporting of the number of spectators who cheer the user A (cheerer number).

For example, the report control section 2142 included in the control section 2104 of the activity meter 2010A can carry out report relating to the spectator number by controlling the LED of the reporting section 2106 to emit light such that green light becomes brighter as the spectator number increases. Moreover, the report control section 2142 can carry out report relating to the cheerer number by controlling the LED of the reporting section 2106 to emit light such that blue light becomes brighter as the cheerer number increases.

As above described, in a case where the exerciser information sharing/reporting process is carried out so that the activity meter 2010 used by the spectator reports information regarding an activity amount of the exerciser, the information regarding the activity amount of the exerciser can be shared between the exerciser and the spectator who have been registered as friends. Moreover, in a case where the spectator information sharing/reporting process is carried out so that the activity meter 2010 used by the exerciser reports information regarding a momentum of the spectator, the information regarding the activity amount of the spectator can be shared between the exerciser and the spectator who have been registered as friends.

Further, according to the above configuration, the exerciser and the spectator do not need to operate their mobile devices 2020 in both cases where (i) information regarding the activity amount of the exerciser is shared between the exerciser and the spectator and (ii) information regarding the activity amount of the spectator is shared between the exerciser and the spectator. That is, the exerciser and the spectator who register the same event as schedule information can share information regarding their activity amounts without operating their mobile devices 2020.

In Embodiment 10, the configuration is described in which the sharing/reporting process is carried out between the activity meter 2010 used by the participant of the event and the activity meter 2010 used by the spectator. Note, however, that the present invention is not limited as such. For example, the sharing/reporting process can be carried out between activity meters 2010 which are used by participants of an event, or the sharing/reporting process can be carried out between activity meters 2010 which are used by spectators.

From these, exercisers who register the same event as schedule information or spectators who register the same event as schedule information can share information regarding their activity amounts without operating their mobile devices 2020.

Moreover, in Embodiment 10, a configuration example is described in which the sharing ability judging process (Step S2103 in FIG. 20, Step S2202 in FIG. 21) is carried out by the server 2030 (specifically, the sharing control section 2321 included in the control section 2302 of the server 2030). However, the present invention is not limited as such. For example, it is possible to employ a configuration in which the sharing ability judging process is carried out by the control section 2104 of the activity meter 2010 or the control section 2203 of the mobile device 2020.

Embodiment 11

In Embodiment 10, sharing of an activity amount in a case where the user A and the user B participate in an event is described. Of course, the present invention is not limited as such. For example, even in a case where the user A carries out exercise during a period of time in which neither plan nor event is registered as schedule information, information regarding an activity amount can be shared between the user A and the user B.

The sharing control section 2321 included in the control section 2302 of the server 2030 judges, with reference to schedule information of the user B stored in the schedule information management region 2333, whether or not a reporting operation can be carried out with the activity meter 2010B used by the user B, as with the sharing ability judging process in the exerciser information sharing/reporting process of Embodiment 10 (Step S2103 in FIG. 20).

Here, in a case where no plan is registered, in which the user B cannot confirm a reporting operation carried out with the activity meter 2010B, in a time period which has been referred to by the sharing control section 2321, the sharing control section 2321 determines that a reporting operation can be carried out with the activity meter 2010B. Meanwhile, in a case where a plan is registered, in which the user B cannot confirm a reporting operation carried out with the activity meter 2010B, in a time period which has been referred to by the sharing control section 2321, the sharing control section 2321 determines that a reporting operation cannot be carried out with the activity meter 2010B.

The plan in which the user B cannot confirm a reporting operation carried out with the activity meter 2010B can be, for example, a plan to sleep, a plan to move by car, and the like.

In a case where the sharing control section 2321 has determined that a reporting operation can be carried out with the activity meter 2010B, the notification control section 2322 included in the control section 2302 of the server 2030 notifies the activity meter 2010B of a reporting instruction.

Further, the sharing control section (activity status judging section) 321 included in the control section 2302 of the server 2030 can judge an activity status of the user B (i) based on activity amount information indicative of an activity amount of the user B which activity amount has been measured by the activity meter 2010B and (ii) at a time point at which activity amount information indicative of an activity amount which has been measured by the activity meter 2010A is obtained. Examples of the activity status of the user encompass statuses in which the user is currently walking, running, resting, sleeping, and the like.

With the configuration, in a case where the activity status of the user B indicates a state in which the user B can confirm a reporting operation carried out with the activity meter 2010B (e.g., in a status where the user B is walking, running, or the like), the sharing control section 2321 can determine that a reporting operation can be carried out with the activity meter 2010B. On the other hand, in a case where the activity status of the user B indicates a state in which the user B cannot confirm a reporting operation carried out with the activity meter 2010B (e.g., in a status where the user B is sleeping or the like), the sharing control section 2321 can determine that a reporting operation cannot be carried out with the activity meter 2010B.

It is possible to employ a configuration in which the schedule information includes information (also referred to as activity status information) indicative of a current activity status of the user, in addition to information regarding a plan and an event of the user.

For example, it is possible that the control section 2302 of the server 2030 (i) obtains, for each predetermined time period (e.g., per 1 hour), activity amount information which has been calculated by the activity amount calculating section 2141 included in the control section 2104 of the activity meter 2010 and (ii) updates, for each of the predetermined time period, activity status information stored in the schedule information management region 2333 based on the obtained activity amount information. Moreover, it is possible that the control section 2302 of the server 2030 (i) calculates, for each predetermined time period, activity status information of the user based on activity amount information obtained from the activity meter 2010 and (ii) updates, for each of the predetermined time period, activity status information stored in the schedule information management region 2333 based on the calculated activity status information. With the configuration, the schedule information stored in the schedule information management region 2333 is to contain latest activity status information for each predetermined time period.

In this case, the sharing control section 2321 judges, with reference to latest activity information contained in the schedule information of the user B, whether or not a reporting operation can be carried out with the activity meter 2010B used by the user B. For example, in a case where the current activity information of the user B indicates a state in which the user B can confirm a reporting operation carried out with the activity meter 2010B (e.g., in a status where the user B is walking, running, or the like), the sharing control section 2321 can determine that a reporting operation can be carried out with the activity meter 2010B. On the other hand, in a case where the current activity information of the user B indicates a state in which the user B cannot confirm a reporting operation carried out with the activity meter 2010B (e.g., in a status where the user B is sleeping or the like), the sharing control section 2321 can determine that a reporting operation cannot be carried out with the activity meter 2010B.

Embodiment 12

In Embodiment 10, the server 2030 judges whether or not a reporting operation can be carried out, in the sharing ability judging process (Step S2103 in FIG. 20, Step S2202 in FIG. 21) in the sharing/reporting process. Note, however, that the present invention is not limited as such. For example, whether or not a reporting operation can be carried out can be judged by carrying out a synchronization ability judging process for judging whether or not another activity meter 2010 which is to carry out a reporting operation is ready for communication.

Note that the judging of whether or not the another activity meter 2010 is ready for communication in Embodiment 12 can be carried out instead of the sharing ability judging process or can be carried out together with the sharing ability judging process.

[Configuration of Information Sharing System]

In Embodiment 12, an example is described in which a reporting operation is carried out with the activity meter 2010B in accordance with activity amount information which has been measured by the activity meter 2010A.

The communication section 2201 of the mobile device 2020B which is included in the information sharing system 2001 constantly communicates with the activity meter 2010B via short-distance wireless communication. The control section 2203 successively judges whether or not the communication section 2201 can wirelessly communicate with the activity meter 2010B (i.e., judges a communication status). Examples of a case where wireless communication cannot be carried out encompass a case where a battery of the activity meter 2010B has run out, a case where the activity meter 2010B is out of service range, and the like.

In a case where a communication status between the communication section 2201 and the activity meter 2010B has been switched (i) from a state where the wireless communication is available to a state where the wireless communication is unavailable, or (ii) from a state where the wireless communication is unavailable to a state where the wireless communication is available, the control section 2203 notifies the server 2030 of the communication status thus changed.

The control section 2302 of the server 2030 causes the communication status of the activity meter 2010B, which communication status has been obtained from the mobile device 2020B, to be stored in the management information storage section 2303.

Moreover, the control section 2302 judges, for each predetermined time period (e.g., per 10 minutes), the communication status between the communication section 2301 and the mobile device 2020B. Examples of a case where wireless communication cannot be carried out encompass a case where a battery of the mobile device 2020B has run out, a case where the mobile device 2020B is out of service range, and the like.

In a case where a communication status between the communication section 2301 and the mobile device 2020B has been switched (i) from a state where the wireless communication is available to a state where the wireless communication is unavailable, or (ii) from a state where the wireless communication is unavailable to a state where the wireless communication is available, the control section 2302 causes the changed communication status with the mobile device 2020B to be stored in the management information storage section 2303.

The control section 2302 refers to latest communication statuses which are of the activity meter 2010B and the mobile device 2020B, respectively, and are stored in the management information storage section 2303 at a time point at which the control section 2302 has obtained activity amount information from the activity meter 2010A via the mobile device 2020A. In a case where both the referred latest communication statuses of the activity meter 2010B and the mobile device 2020B indicate that communication is available, the control section 2302 transmits a reporting instruction to the activity meter 2010B via the mobile device 2020B.

Embodiment 13

The following description will discuss, with reference to FIGS. 22 through 29, an embodiment of the activity support system of the present invention. Note, however, that the configurations in this embodiment merely exemplify an embodiment of the present invention, and therefore should not be construed as limiting the scope of the invention only to them unless otherwise noted.

[Configuration of Activity Support System]

First, the following description will discuss an activity support system of Embodiment 13 with reference to FIG. 23. FIG. 23 is a view illustrating an appearance of an activity support system 3001 according to Embodiment 13.

As illustrated in FIG. 23, the activity support system 3001 includes an activity meter (activity amount measuring device) 3010, a mobile device 3020, and a server (activity support device) 3030. Moreover, as illustrated in FIG. 23, the activity support system 3001 according to Embodiment 13 includes a plurality of activity meters 3010 and a plurality of mobile devices 3020. In FIG. 23, a mobile device 3020 corresponding to the activity meter 3010, that is, a mobile device 3020 which communicates with the activity meter 3010 via short-distance wireless communication (i.e., a mobile device 3020 that is possessed by a user (another user) who possesses the activity meter 3010) is referred to as "mobile device 3020A". Moreover, a mobile device 3020 which does not communicate with the activity meter 3010 via short-distance wireless communication (i.e., a mobile device 3020 used by a user (target user) who does not use the activity meter 3010) is referred to as "mobile device 3020B".

In Embodiment 13, the short-distance wireless communication between the activity meter 3010 and the mobile device 3020A is carried out by use of low-power-consumption short-distance wireless communication. Examples of the low-power-consumption short-distance wireless communication encompass Bluetooth (registered trademark) 4.0 (known as Bluetooth Low Energy) and ANT.

The activity meter 3010 measures an activity amount of a user and transmits activity amount information, which indicates the activity amount thus measured, to a server 3030 via the mobile device 3020A.

On the mobile device 3020, an application for presenting an activity amount to the user (e.g., a walking application for supporting walking) is executed. In a case where the walking application is executed, the mobile device 3020 displays a map (later described, illustrated in FIGS. 25 and 29) showing a walking route and also displays some activity amounts (e.g., an EX amount, the number of steps, a walking distance, a consumed calorie, and the like).

In Embodiment 13, the activity meter 3010 is a wrist band-type activity meter which can be put on a wrist of a user as illustrated in FIG. 23. Note, however, that the a of the activity meter 3010 is not limited to a wrist band-type, provided that the activity meter 3010 can be put on the user's body, directly or indirectly. Examples of the activity meter 3010 encompass (i) a necklace-type activity meter which can be put on the user's neck and (ii) a clip-type activity meter which can be put on the user's body via clothing.

In Embodiment 13, the mobile device 3020 is a smartphone as illustrated in FIG. 23. Note, however, that the mobile device 3020 is not limited to a smartphone, provide that the mobile device 3020 is a portable information processing device. Examples of the mobile device 3020 encompass a mobile phone, a PDA (Personal Digital Assistant), and a tablet PC (Personal Computer).

The following description will schematically discuss, with reference to FIG. 22, configurations of the activity meter 3010, the mobile device 3020, and the server 3030 which are included in the activity support system 3001 according to Embodiment 13. FIG. 22 is a block diagram illustrating configurations of the activity meter 3010, the mobile device 3020, and the server 3030 which are included in the activity support system 3001 according to Embodiment 13.

[Activity Meter 3010]

The activity meter 3010 is a device for measuring an activity amount of a user who is wearing the activity meter 3010 and transmits, to the mobile device 3020, activity amount information indicative of a measured activity amount. As illustrated in FIG. 22, the activity meter 3010 includes a sensor section 3101, a timekeeping section 3102, a communication section 3103, a control section 3104, and a storage section 3105.

(Sensor Section 3101)

The sensor section 3101 includes at least an acceleration sensor. The sensor section 3101 supplies, to the control section 3104, a sensor signal which indicates acceleration detected. In Embodiment 13, the sensor section 3101 includes a three-axis acceleration sensor. Alternatively, the sensor section 3101 can include a two-axis acceleration sensor or a one-axis acceleration sensor, instead of a three-axis acceleration sensor. Alternatively, the sensor section 3101 can include, in addition to an acceleration sensor, a gyrosensor, an altitude (atmospheric pressure) sensor, a temperature sensor, a humidity sensor, and/or the like. Referring to sensor signals supplied from these sensors, it is possible to more accurately calculate an activity amount which depends on a posture of a user and on a surrounding environment.

(Timekeeping Section 3102)

The timekeeping section 3102 is a timer for notifying the control section 3104 that an amount of time specified by the control section 3104 has passed. Specifically, the timekeeping section 3102 judges whether or not a predetermined time period has elapsed. In a case where the timekeeping section 3102 has determined that the predetermined time period has elapsed, the timekeeping section 3102 notifies the control section 3104 that the predetermined time period has elapsed. The timekeeping section 3102 repeatedly carries out a sequence of processes including (i) the judging of whether or not the predetermined time period has elapsed and (ii) the notifying of the fact that the predetermined time period has elapsed.

The predetermined time period is not limited to a particular one and can be, for example, 1 hour, 10 minutes, or 1 minute. Moreover, the predetermined time period can be arbitrarily set by the user. In this case, the predetermined time period can be set by operating an operation section (not illustrated) included in the activity meter 3010 or can be set by operating an operation section 3204 (later described) included in the mobile device 3020.

The timekeeping section 3102 can further include a clock. In this case, the timekeeping section 3102 can notify the control section 3104 of the time.

(Communication Section 3103)

The communication section 3103 communicates with the mobile device 3020 via short-distance wireless communication. The communication section 3103 transmits, to the mobile device 3020, activity amount information which has been supplied from the control section 3104 and receives a reporting instruction transmitted from the mobile device 3020 (details of the activity amount information and the reporting instruction will be described later).

(Control Section 3104)

The control section 3104 comprehensively controls the sections of the activity meter 3010. The control section 3104 is configured by, for example, a CPU (central processing unit) or the like. The control section 3104 includes a sensor output analyzing section 3141, an activity amount measuring section 3142, and a transfer data generating section 3143 (see FIG. 22).

The sensor output analyzing section 3141 counts the number of steps (primary activity amount) by referring to a sensor signal supplied from the sensor section 3101. Counting of the number of steps in accordance with a sensor signal indicative of acceleration can be carried out by use of a known algorithm. The number of steps thus counted by the sensor output analyzing section 3141 is stored as activity amount information in the storage section 3105.

The activity amount measuring section 3142 calculates various activity amounts (secondary activity amount) based on the number of steps stored in the storage section 3105. Calculation of the various activity amounts based on the number of steps can be carried out by use of a known algorithm. An activity amount calculated by the activity amount measuring section 3142 is stored as activity amount information in the storage section 3105.

The transfer data generating section 3143 reads out, from the storage section 3105, activity amount information which has not been transmitted. Then, the transfer data generating section 3143 generates transfer data which contains the activity amount information thus read out. The transfer data thus generated is transmitted to the mobile device 3020 via the communication section 3103. Note that timings with which the transfer data generating section 3143 generates the transfer data, that is, timings with which the activity amount information is transmitted to the mobile device 3020 can be controlled by the timekeeping section 3102. In order to efficiently use a capacity of the storage section 3105, the transfer data generating section 3143 preferably deletes, from the storage section 3105, the activity amount information which has been read out to be transmitted.

(Storage Section 3105)

The storage section 3105 stores data received by the communication section 3103, activity amount information calculated by the activity amount measuring section 3142 included in the control section 3104, and the like.

[Mobile Device 3020]

The mobile device 3020 is a device which cooperates with the activity meter 3010 so as to measure an activity amount of the user. As illustrated in FIG. 22, the mobile device 3020 includes a communication section (receiving section) 3201, an auxiliary information obtaining section 3202, a control section 3203, an operation section 3204, a storage section 3205, and a display section (presenting section) 3206. In Embodiment 13, the mobile device 3020A and the mobile device 3020B have identical configurations, and therefore each of the mobile device 3020A and the mobile device 3020B is described as a mobile device 3020.

(Communication Section 3201)

The communication section 3201 communicates with the activity meter 3010 via short-distance wireless communication and communicates with the server 3030 via wireless communication. Note that the wireless communication between the communication section 3201 and the server 3030 is not limited to a particular one, provided that the wireless communication is carried out via a network such as the Internet.

(Auxiliary Information Obtaining Section 3202)

The auxiliary information obtaining section 3202 obtains subsidiary information (activity amount auxiliary information) which relates to an activity amount of the user. In Embodiment 13, the auxiliary information obtaining section 3202 can be configured by, for example, GPS (Global Positioning System). In this case, the auxiliary information obtaining section 3202 obtains, as activity amount auxiliary information, a latitudinal value and a longitudinal value of a location of the user.

(Operation Section 3204)

The operation section 3204 accepts a user operation and supplies, to the control section 3203, operation information indicative of the user operation thus accepted. The operation section 3204 is not limited to a particular one and can be configured by, for example, a plurality of physical buttons (hardware key), a touch panel, or the like.

Moreover, the operation section 3204 accepts a user instruction on generating an activity route for an activity (e.g., walking, jogging, or the like). The operation section 3204 accepts, as the user instruction on generating a route, for example, input of route information such as a start point of the user's activity, a destination, and a condition (route condition) of a route intended by the user.

(Control Section 3203)

The control section 3203 comprehensively controls the sections of the mobile device 3020. The control section 3203 is configured by, for example, a CPU (central processing unit) or the like.

The control section 3203 transmits, to the server 3030 via the communication section 3201, activity amount information of the user obtained from the activity meter 3010 and activity amount auxiliary information obtained by the auxiliary information obtaining section 3202. Specifically, the control section 3203 causes activity amount information and activity amount auxiliary information to be stored in the storage section 3205 and, each time a predetermined time period (e.g., 1 second, 1 minute, or 10 minutes) elapses, the control section 3203 transmits, to the server 3030, activity amount information and activity amount auxiliary information which have been stored in the storage section 3205 during the predetermined time period.

Based on the user instruction on generating an activity route which instruction has been accepted via the operation section 3204, the control section 3203 transmits, to the server 3030 via the communication section 3301, a route request instruction on requesting the server 3030 to generate the activity route. Note that the route request instruction includes the above described route information.

The control section 3203 controls, in accordance with map information indicative of a map including the route generated in accordance with the route request instruction, the display section 3206 to display the map including the route generated in accordance with the route request instruction.

(Storage Section 3205)

The storage section 3205 is controlled by the control section 3203 to temporarily store user's activity amount information which has been obtained from the activity meter 3010 and activity amount auxiliary information which has been obtained by the auxiliary information obtaining section 3202.

(Display section 3206)

The display section 3206 displays an activity amount which is indicated by activity amount information supplied from the control section 3203. The display section 3206 can be configured by a transmissive liquid crystal panel having a backlight. Note, however, that the display section 3206 is not limited as such, but can be configured by another display such as an organic EL display.

[Server 3030]

The server 3030 is a device which integrally controls a process relating to presenting an activity amount to the user with the activity meter 3010 and the mobile device 3020. As illustrated in FIG. 22, the server 3030 includes a communication section 3301, a control section 3302, and a storage section 3303. In Embodiment 13, an example is described in which the server 3030 is configured by one server. Note, however, that the present invention is not limited as such and the server 3030 can be configured by servers which are different in at least any of functions of the sections.

(Communication Section 3301)

The communication section 3301 wirelessly communicates with the mobile device 3020 via, for example, a network such as the Internet.

(Control Section 3302)

The control section 3302 comprehensively controls the sections included in the server 3030. The control section 3302 includes a route generating section 3321, an activity amount managing section (obtaining section, recording section, environment information obtaining section) 3322, and an activity amount extracting section (providing section) 3323.

The route generating section 3321 generates, based on a route request instruction transmitted from the mobile device 3020, an activity route which the user refers to in the activity. In Embodiment 13, an example is described in which the activity of the user is walking and a walking route is generated as the activity route. Note, however, that the present invention is not limited as such. For example, in a case where the activity of the user is jogging, the route generating section 3321 can generate a jogging course.

Examples of the route condition encompass a condition that a required time from a start point to a destination is approximately 1 hour; a condition that a distance from a start point to a destination is approximately 1 km; a condition that it is required to pass through a specified store during walking from a start point to a destination; and the like.

The route generating section 3321 transmits map information, which indicates a map including a generated walking route, to the mobile device 3020 via the communication section 3301.

The activity amount managing section 3322 obtains, from the mobile device 3020A via the communication section 3301, (i) activity amount information which indicates an activity amount of a predetermined exercise carried out by the user using the activity meter 3010 and (ii) activity amount auxiliary information obtained by the mobile device 3020. Here, in this specification, "predetermined exercise" collectively indicates, for example, exercises such as yoga, gymnastics, and swimming; moving along a predetermined route such as jogging and cycling; and activities of ordinary days such as household chores. In Embodiment 13, an example is described in which moving along a predetermined route is carried out as the predetermined exercise.

The activity amount managing section 3322 causes the activity amount information and the activity amount auxiliary information, which have been obtained, to be stored in the storage section 3303 in a form of an activity amount management table in which the activity amount information and the activity amount auxiliary information are associated with the route. The activity amount management table will be described later.

Note that examples of the moving along a route encompass walking, jogging, cycling, and the like.

The activity amount extracting section 3323 reads out the activity amount management table from the storage section 3303 and further reads out momentum information from the activity amount management table which has been read out. Thus, the activity amount extracting section 3323 carries out a process of presenting an activity amount to a user who is not using the activity meter 3010 (i.e., who uses the mobile device 3020B).

Specifically, the activity amount extracting section 3323 first reads out the activity amount management table in which (i) route information is registered which is identical with route information contained in a route request instruction transmitted from the mobile device 3020B and (ii) user information is registered which is similar to user information (user attribute information) of the user of the mobile device 3020B. Then, the activity amount extracting section 3323 extracts, from the activity amount management table which has been read out, activity amount information which is associated with location information similar to location information indicated by momentum auxiliary information which has been transmitted from the mobile device 3020B. Note that the process carried out by the activity amount extracting section 3323 will be described later in detail.

(Storage Section 3303)

The storage section 3303 stores various pieces of management information. As illustrated in FIG. 22, the storage section 3303 stores the activity amount management table. Note that details of the activity amount management table will be described later.

(Example of Activity Amount Auxiliary Information)

The following description will discuss, with reference to FIG. 24, a concrete example of data indicated by activity amount auxiliary information transmitted from the mobile device 3020A to the server 3030. FIG. 24 is a view illustrating data that is indicated by activity amount auxiliary information transmitted from the mobile device 3020A to the server 3030, according to Embodiment 13.

As illustrated in FIG. 24, the activity amount auxiliary information transmitted from the mobile device 3020A contains time information (timestamp), latitude, longitude, altitude, and accuracy. In the example illustrated in FIG. 24, the activity amount auxiliary information is transmitted from the mobile device 3020A every second, as the time information (timestamp) indicates.

[Route Generating Process]

The following description will discuss, with reference to FIG. 25, a route generating process for generating a walking route by the activity support system 3001 (specifically, by the route generating section 3321 of the control section 3302 included in the server 3030). FIG. 25 is a view schematically illustrating an example of a map which (i) includes a route generated by the route generating section 3321 of the server 3030 and (ii) is displayed by the display section 3206 of the mobile device 3020, according to Embodiment 13. (a) of FIG. 25 illustrates a map in which a start point is a point E, a destination is a point F, and a route condition is set so that a distance from the point E to the point F becomes 1 km. (b) of FIG. 25 illustrates a map in which a start point is a point G, a destination is a point H, and a route condition is set so that the route passes through a point I.

First, in the activity support system 3001, the operation section 3204 included in the mobile device 3020 accepts input of route information such as a start point, a destination, and a route condition which are intended by the user. For example, in a case where the operation section 3204 has accepted input of determining a route in which a start point is a point E, a destination is a point F, and a distance from the start point and the destination is approximately 1 km as a route condition, the mobile device 3020 transmits the accepted route information to the server 3030.

The route generating section 3321 of the control section 3302 included in the server 3030, which has received the route information from the mobile device 3020, first sets a start point E and a destination F. Then, the route generating section 3321 selects a route that satisfies the route condition from among routes each of which connects the start point E with the destination F (that is, selects a route in which the distance from the start point E to the destination F is approximately 1 km).

In this case, in a case where there are a plurality of routes which satisfy the route condition, it is possible to employ (i) a configuration in which the route generating section 3321 automatically selects one route from the plurality of routes or (ii) a configuration in which the user selects one of the plurality of routes which are displayed on the display section 3206 of the mobile device 3020.

The route generating section 3321 generates a walking route which connects the point E (set as the start point) with the point F (set as the destination) while satisfying the route condition. Further, the route generating section 3321 generates route data indicating a map in which the generated walking route is emphasized (e.g., highlighted in a color different from those of the other routes) (see (a) of FIG. 25).

Alternatively, in a case where the operation section 3204 of the mobile device 3020 has accepted input of determining a route in which a start point is a point G and a destination is a point H and which passes through a point I as a route condition, the route generating section 3321 generates a walking route which connects the point E (set as the start point) with the point F (set as the destination) and passes through the point I (see (b) of FIG. 25).

[Activity Amount Management Table]

Next, the following description will discuss the activity amount management table with reference to FIG. 26. FIG. 26 is a view illustrating the activity amount management table according to Embodiment 13. (a) of FIG. 26 is a view illustrating a fixed data table in the activity amount management table, and (b) of FIG. 26 is a view illustrating a variable data table in the activity amount management table.

The activity amount table includes (i) a fixed data table for managing fixed data (such as route information) which does not sequentially change and (ii) a variable data table for managing variable data (such as the number of steps and location information) which sequentially changes (see (a) and (b) of FIG. 26).

The fixed data table includes (i) user information such as a height, a weight, an age, a gender and a stride of a user using the activity meter 3010 (i.e., using the mobile device 3020A), (ii) route information such as a start point, a destination, and a route condition, and (iii) environment information such as weather, an air temperature, and humidity (see (a) of FIG. 26). The environment information can further contain information (e.g., mud state of road, presence/absence of baggage, and the like) from which METs can be known based on a METs table (which is published by National Institute of Health and Nutrition and in which activity contents are associated with activity amounts).

The variable data table includes (i) time information, (ii) activity amount information such as the number of steps, a momentum, an EX amount, and a consumed calorie which correspond to each of time points indicated by the time information, and (iii) activity amount auxiliary information such as a latitude, a longitude, and an altitude which correspond to each of the time points (see (b) of FIG. 26). The activity amount auxiliary information can further include a value indicating accuracy of the latitude, the longitude, and the altitude which have been obtained by the auxiliary information obtaining section 3202 of the mobile device 3020A (see (b) of FIG. 26).

In Embodiment 13, an example is described in which moving along a predetermined route is carried out as the predetermined exercise. Note, however, that, in a case where the predetermined exercise is yoga, it is possible to register, in the activity amount management table, information such as a pose of yoga and duration of the pose, instead of the route information.

(Activity Amount Management Table Generating Process)

Next, the following description will discuss a process of generating an activity amount management table by the activity amount managing section 3322 of the control section 3302 included in the server 3030.

In a case where the activity amount managing section 3322 has received a route request instruction from the mobile device 3020A, the activity amount managing section 3322 obtains user information of the user using the mobile device 3020A from which the route request instruction has been transmitted. The user information, for example, can be obtained from the mobile device 3020A together with the route request instruction or can be registered in the storage section 3303 of the server 3030 in advance. The activity amount managing section 3322 causes route information contained in the route request instruction and the obtained user information to be stored in the storage section 3303 so that the route information and the user information are associated with each other in a fixed data table in an activity amount management table as illustrated in (a) of FIG. 26.

Moreover, the activity amount managing section 3322 obtains, via a network such as the Internet for example, environment information of an area in which the walking route exists which has been generated by the route generating section 3321 in accordance with the route request instruction. The activity amount managing section 3322 causes the obtained environment information to be stored in the storage section 3303 so that the environment information is associated with the route information and the user information in the fixed data table in the activity amount management table as illustrated in (a) of FIG. 26.

Further, the activity amount managing section 3322 obtains, from the mobile device 3020A, activity amount information regarding walking of the user and activity amount auxiliary information for each predetermined time period. The activity amount managing section 3322 causes the activity amount information and the activity amount auxiliary information, which have been thus obtained, to be temporarily stored in the storage section 3303 together with time information that indicates the time at which the activity amount information and the activity amount auxiliary information have been obtained. In a case where the user has ended walking (i.e., in a case where the user has reached the destination), the activity amount managing section 3322 causes the time information, the activity amount information, and the activity amount auxiliary information, which have been temporarily stored in the storage section 3303, to be stored in the storage section 3303 in a form of a variable data table in the activity amount management table so that the variable data table is associated with the fixed data table.

In Embodiment 13, a configuration example is described in which, in a case where the user has reached the destination, the time information, the activity amount information, and the activity amount auxiliary information which have been temporarily stored in the storage section 3303 are collectively recorded in the activity amount management table. Note, however, that the present invention is not limited as such. For example, it is possible to employ a configuration in which, every time the activity amount managing section 3322 obtains time information, activity amount information, and activity amount auxiliary information from the mobile device 3020A, the activity amount managing section 3322 records the time information, the activity amount information, and the activity amount auxiliary information in the activity amount management table.

In Embodiment 13, a configuration example is described in which an activity amount management table is generated for each user. Note, however, that the present invention is not limited as such. For example, it is possible that an activity amount management table is generated by averaging activity amounts indicated by pieces of activity amount information of users whose pieces of user information fall within a predetermined range. Note that a case where pieces of user information fall within a predetermined range indicates, for example, a case where a height is 165 cm to 174 cm, a case where a weight is 65 kg to 74 kg, and the like.

[Activity Amount Presenting Process]

Next, the following description will discuss, with reference to FIGS. 27 and 28, a flow of a process (activity amount presenting process) which is carried out in the activity support system 3001 and in which a walking route is presented to a user and an activity amount relating to walking along the presented route is presented. FIG. 27 is a sequence diagram illustrating an activity amount presenting process which is carried out in the activity support system 3001 with respect to a user who uses the activity meter 3010, according to Embodiment 13. FIG. 28 is a sequence diagram illustrating a flow of an activity amount presenting process carried out with respect to a user who does not use the activity meter 3010.

(Activity Amount Presenting Process with Respect to User Who Uses Activity Meter)

First, the following description will discuss, with reference to FIG. 27, a flow of an activity amount presenting process carried out with respect to a user who uses the activity meter 3010.

As illustrated in FIG. 27, first, the operation section 3204 of the mobile device 3020A accepts input of route information indicating a start point, a destination, a route condition, and the like (Step S3101). When the input of the route information has been accepted, the control section 3203 of the mobile device 3020A notifies, via the communication section 3201, the server 3030 of a route request instruction which contains the route information which has been accepted.

In a case where the route generating section 3321 included in the control section 3302 of the server 3030 has obtained the route request instruction, the route generating section 3321 generates a walking route in accordance with the route information included in the route request instruction thus obtained (Step S3102). The route generating section 3321 transmits map information indicative of a map including the generated walking route to the mobile device 3020A via the communication section 3301.

In a case where the control section 3203 of the mobile device 3020A has obtained the map information from the server 3030, the control section 3203 controls the display section 3206 to display the map indicated by the obtained map information, and thus presents, to the user of the mobile device 3020A, the walking route intended by the user (Step S3103). Moreover, the control section 3203 of the mobile device 3020A notifies the activity meter 3010 of a measurement start instruction on starting measurement of an activity amount of the user.

The auxiliary information obtaining section 3202 of the mobile device 3020A obtains activity amount auxiliary information which indicates a current location of the user on the walking route.

In a case where the activity meter 3010 has obtained the measurement start instruction, the sensor output analyzing section 3141 and the activity amount measuring section 3142 which are included in the control section 3104 of the activity meter 3010 start measuring an activity amount relating to walking of the user (Step S3104). Then, the transfer data generating section 3143 (i) generates transfer data every time a predetermined time period elapses and (ii) accordingly transmits the transfer data thus generated to the mobile device 3020A via the communication section 3103.

Every time the control section 3203 of the mobile device 3020A has received transfer data, the control section 3203 controls the display section 3206 to display an activity amount indicated by activity amount information included in the transfer data which has been received (Step S3105). Moreover, the mobile device 3020A transmits, to the server 3030 via the communication section 3201, (i) obtained transfer data and (ii) activity amount auxiliary information which has been obtained by the auxiliary information obtaining section 3202.

The activity amount managing section 3322 of the control section 3302 included in the server 3030 causes the activity amount information and the activity amount auxiliary information, which are indicated by the received transfer data, to be temporarily stored in the storage section 3303 (Step S3106).

Moreover, the control section 3302 judges, based on a user's current location indicated by the received activity amount auxiliary information, whether or not the user has reached the destination (Step S3107). The control section 3302 can judge whether or not the user has reached the destination by comparing values of a latitude and a longitude of a point set as the destination with values of a latitude and a longitude contained in the activity amount auxiliary information.

In a case where the control section 3302 has determined that the user has not reached the destination (NO in Step S3107), the server 3030 carries out the process of the step S3106 again. In other words, the server 3030 repeats the processes of the steps S3106 and S3107 until the control section 3302 determines that the user has reached the destination (YES in Step S3107).

In a case where the control section 3302 has determined that the user has reached the destination (YES in Step S3107), the control section 3302 of the server 3030 transmits, to the activity meter 3010 via the mobile device 3020A, a stop instruction for causing the activity meter 3010 to stop measuring the activity amount of the user. Upon receipt of the stop instruction, the activity meter 3010 stops measuring the activity amount, and the mobile device 3020A stops obtaining the activity amount auxiliary information.

The activity amount managing section 3322 of the control section 3302 records, in the storage section 3303, an activity amount management table in which pieces of activity amount information and pieces of activity amount auxiliary information, which have been obtained while the user moves from the start point to the destination, are associated with time information indicating time points at which the pieces of activity amount information and the pieces of activity amount auxiliary information have been obtained (Step S3108). In this case, the activity amount managing section 3322 further records, in the activity amount management table, route information such as the route condition inputted at the step S3101, user information of the mobile device 3020A, and environment information such as weather at the time at which the walking has been carried out, so that these pieces of information in the activity amount management table are associated with each other.

Note that, in Embodiment 13, in a case where the user is out of the walking route, the activity amount managing section 3322 does not need to record an activity amount of the user while the user is walking out of the route. This makes it possible to prevent a situation where an activity amount of the user of the mobile device 3020A while the user is on a route other than the walking route is recorded as an activity amount of a case where the user has walked along the walking route generated by the route generating section 3321.

In Embodiment 13, a configuration example is described in which the mobile device 3020A periodically transmits, to the server 3030, transfer data and activity amount auxiliary information for each predetermined time period. Note, however, that the present invention is not limited as such.

For example, it is possible to employ a configuration in which, in the mobile device 3020A, transfer data and activity amount auxiliary information are temporarily stored in the storage section 3205 and then the transfer data and the activity amount auxiliary information which have been stored in the storage section 3205 are collectively transmitted to the server 3030 after walking is ended. According to the configuration, the mobile device 3020A can supply an activity amount of walking to the server 3030 even in a case where, for example, the walking has been carried out along a walking route on which a communication status between the mobile device 3020A and the server 3030 is poor (i.e., communication cannot be maintained).

(Activity Amount Presenting Process with Respect to User Who does not Use Activity Meter)

Next, the following description will discuss, with reference to FIG. 28, a flow of an activity amount presenting process carried out with respect to a user who does not use the activity meter 3010.

As illustrated in FIG. 28, first, the mobile device 3020B accepts input of route information (Step S3201). When the input of the route information has been accepted, the control section 3203 of the mobile device 3020B notifies, via the communication section 3201, the server 3030 of a route request instruction which contains the route information which has been accepted.

In a case where the route generating section 3321 included in the control section 3302 of the server 3030 has obtained the route request instruction, the route generating section 3321 generates a walking route in accordance with the route information included in the route request instruction thus obtained (Step S3202). The route generating section 3321 transmits map information indicative of a map including the generated walking route to the mobile device 3020B via the communication section 3301.

The activity amount extracting section 3323 of the control section included in the server 3030 reads out, from among a plurality of activity amount management tables stored in the storage section 3303, an activity amount management table which (i) contains route information that is identical with route information contained in the route request instruction accepted in the step S3201 and (ii) contains user information that is similar to user information of the user of the mobile device 3020B (Step S3203).

Here, the activity amount extracting section 3323 can determine that user information is similar in a case where, for example, a height of the user of the mobile device 3020B is 170 cm and a height indicated by user information registered in an activity amount management table falls within a predetermined range (e.g., 165 cm to 174 cm).

In a case where the control section 3203 of the mobile device 3020B has obtained the map information from the server 3030, the control section 3203 controls the display section 3206 to display the map indicated by the obtained map information, and thus presents, to the user of the mobile device 3020B, the walking route intended by the user (Step S3204).

The auxiliary information obtaining section 3202 of the mobile device 3020B obtains activity amount auxiliary information, which indicates a current location of the user on the walking route, every time a predetermined time period (e.g., 1 second, 1 minute, or the like) elapses (Step S3205). The mobile device 3020B transmits activity amount auxiliary information obtained by the auxiliary information obtaining section 3202 to the server 3030 via the communication section 3201 every time the activity amount auxiliary information is obtained.

The activity amount extracting section 3323 of the control section 3302 included in the server 3030 extracts, from the activity amount management table which has been read out in the step S3203, activity amount information which is associated with activity amount auxiliary information indicative of a location substantially identical with a current location of the user which current location is indicated by activity amount auxiliary information obtained from the mobile device 3020B (Step S3206). The activity amount extracting section 3323 transmits the activity amount information, which has been extracted from the activity amount management table, to the mobile device 3020B via the communication section 3301.

The control section 3203 of the mobile device 3020B controls the display section 3206 to display an activity amount that is indicated by the received activity amount information (Step S3207).

The control section 3302 included in the server 3030 transmits the extracted activity amount information to the mobile device 3020B, and then judges, based on a current location of the user indicated by the activity amount auxiliary information obtained from the mobile device 3020B, whether or not the user has reached the destination (Step S3208).

In a case where the control section 3302 has determined that the user has not reached the destination (NO in Step S3208), the server 3030 carries out the process of the step S3206 again. In other words, the server 3030 repeats the processes of the steps S3206 and S3208 until the control section 3302 determines that the user has reached the destination (YES in Step S3208).

In a case where the control section 3302 has determined that the user has reached the destination (YES in Step S3208), the control section 3302 of the server 3030 notifies the mobile device 3020B a stop instruction for causing the activity meter 3010 to stop measuring the activity amount of the user. Upon receipt of the stop instruction, the mobile device 3020B stops obtaining the activity amount auxiliary information by the auxiliary information obtaining section 3202.

As such, in a case where the user of the mobile device 3020B carries out walking from the start point G to the start point H via the point I as illustrated in FIG. 29, an activity amount is to be supplied to the mobile device 3020B while an activity amount management table is referred to which is in a case of walking along the walking route illustrated in (b) of FIG. 25 and with which user information similar to user information of the user of the mobile device 3020 is associated.

FIG. 29 is a view schematically illustrating an example of a map which includes a walking route and is displayed by the display section 3206 of the mobile device 3020B, according to Embodiment 13.

In a case where the user of the mobile device 3020B passes through a halfway point (midway point) X illustrated in FIG. 29, the activity amount extracting section 3323 of the control section 3302 included in the server 3030 can (i) extract, from the activity amount management table which the activity amount extracting section 3323 refers to, activity amount information which is associated with activity amount auxiliary information that indicates the halfway point X among pieces of activity amount auxiliary information and (ii) transmit the activity amount information thus extracted to the mobile device 3020B. From this, the user of the mobile device 3020B can know an accurate activity amount at the point X on the walking route without using the activity meter 3010.

In Embodiment 13, a configuration example is described in which the mobile device 3020B periodically obtains activity amount information regarding walking from the server 3030 for each predetermined time period. Note, however, that the present invention is not limited as such.

For example, it is possible to employ a configuration in which, (i) in the mobile device 3020B, pieces of activity amount auxiliary information obtained at every predetermined time period during walking are temporarily stored in the storage section 3205 and then the pieces of activity amount auxiliary information which have been stored in the storage section 3205 are collectively transmitted to the server 3030 after walking is ended, and (ii) the mobile device 3020B obtains all momentums for the walking as responses to the pieces of activity amount auxiliary information. According to the configuration, the mobile device 3020B can receive an activity amount of walking from the server 3030 even in a case where, for example, the walking has been carried out along a walking route on which a communication status between the mobile device 3020B and the server 3030 is poor (i.e., communication cannot be maintained).

Note that in a case where an activity amount at the halfway point X which activity amount is registered in the activity amount management table is an activity amount from the start point G to the halfway point X, the activity amount extracting section 3323 can transmit, to the mobile device 3020B, activity amount information which indicates the activity amount at the halfway point X which activity amount is registered in the activity amount management table.

Meanwhile, in a case where an activity amount at the halfway point X which activity amount is registered in the activity amount management table is an activity amount from a halfway point immediately before the halfway point X to the halfway point X, the activity amount extracting section 3323 extracts activity amounts from the start point G to the halfway point X which activity amounts are registered in the activity amount management table and transmits, to the mobile device 3020B, a total of the extracted activity amounts as activity amount information indicating an activity amount from the start point G to the halfway point X.

According to the configuration, in a case where the user who does not possess the activity meter 3010 carries out walking along the walking route, the server 3030 can supply, to the mobile device 3020B possessed by the user, an activity amount which has been measured during actual walking carried out along the same walking course by another user. From this, the server 3030 can supply, to the mobile device 3020B possessed by the user who does not possess an activity meter 3010, an accurate activity amount corresponding to an activity amount which has been actually measured by an activity meter 3010 possessed by another user, instead of an activity amount which has been automatically calculated from generally defined parameters.

The server 3030 supplies, to the mobile device 3020B, activity amount information that is associated with user attribute information similar to user attribute information of the user of the mobile device 3020B from among pieces of activity amount information obtained from a plurality of mobile devices 3020A. Therefore, in a case where a user who does not possess an activity meter 3010 carries out walking along a walking route, the server 3030 can supply a more accurate activity amount to the mobile device 3020B which is possessed by the user.

This allows the user, who does not possess an activity meter 3010, to know an accurate activity amount for walking, as with a user who possesses an activity meter 3010.

In Embodiment 13, the configuration is employed in which the activity amount extracting section 3323 extracts, from the activity amount management table, activity amount information that is associated with location information indicating a point corresponding to each point on the walking route and transmits the extracted activity amount information to the mobile device 3020B. Note, however, that the present invention is not limited as such. For example, it is possible to employ a configuration in which (i) activity amount information which indicates a total activity amount for moving on the entire walking route is managed in the activity amount management table and (ii) an activity amount at each of points on the walking route is calculated from the total activity amount.

In this case, an activity amount at the point X illustrated in FIG. 29 can be calculated from, for example, as follows:

Activity amount at point $X$ (i.e., activity amount from point $G$ to point $X$)=total activity amount from point $G$ to point $H$×distance from point $G$ to point $X$/distance from point $G$ to point $H$ Note, however, that a calculation method is not limited to a particular one.

Software Implementation Example

Control blocks of the activity meter 100 (100a, 100b) (particularly, activity amount measurement section 111, sleep level judging section 112, notifying section 113 (113a), setting information obtaining section 114, and smartphone control section 115) and control blocks of a smartphone 200 (200a) (particularly, incoming message processing section 211 (211a) and activity meter setting processing section 212) can be realized by a logic circuit (hardware) provided in an integrated circuit (IC chip) or the like or can be alternatively realized by software as executed by a CPU (Central Processing Unit).

In addition, control blocks of respective of the activity meter 1010 and the mobile device 1020 can be realized by a logic circuit (hardware) provided in an integrated circuit (IC chip) or the like or can be alternatively realized by software as executed by a CPU (Central Processing Unit).

In addition, each member included in each of the activity meter 2010, the mobile device 2020, and the server 2030 can be realized by a logic circuit (hardware) provided in an integrated circuit (IC chip) or the like or can be alternatively realized by software as executed by a CPU (Central Processing Unit).

In addition, each member included in each of the activity meter 3010, the mobile device 3020, and the server 3030 can be realized by a logic circuit (hardware) provided in an integrated circuit (IC chip) or the like or can be alternatively realized by software as executed by a CPU (Central Processing Unit).

In the latter case, each of the devices includes a CPU that executes instructions of a program that is software realizing the foregoing functions; ROM (Read Only Memory) or a storage device (each referred to as "storage medium") in which the program and various kinds of data are stored so as to be readable by a computer (or a CPU); and RAM (Random Access Memory) in which the program is loaded. An object of the present invention can be achieved by a computer (or a CPU) reading and executing the program stored in the storage medium. Examples of the storage medium encompass "a non-transitory tangible medium" such as a tape, a disk, a card, a semiconductor memory, and a programmable logic circuit. The program can be supplied to the computer via any transmission medium (such as a communication network or a broadcast wave) which allows the program to be transmitted. Note that the present invention can also be achieved in the form of a computer data signal in which the program is embodied via electronic transmission and which is embedded in a carrier wave.

SUMMARY

In Aspect 1 of the present invention, an activity meter (activity meter 100, 100a, 100b) is an activity meter to be worn by a user, including: a judging section (sleep level judging section 112) for repeatedly judging a sleep level of the user; and a notifying section (notifying section 113, 113a) for automatically notifying the user of specific information only during a period during which a most recent sleep level is less than a predetermined level (threshold TH).

According to the configuration, the activity meter does not notify the user of the specific information during a period during which the most recent sleep level of the user is the predetermined level or greater (i.e., during a period during which it is judged that the user is in the deep sleep state).

Therefore, the activity meter has such an advantage of being unlikely to disturb a user in a deep sleep by notifying the user of the specific information.

In Aspect 2 of the present invention, the activity meter according to Aspect 1 of the present invention can be configured so that the notifying section notifying the user of, as the specific information, information regarding a measurement result only during a period during which a most recent sleep level indicates that the user is not in a specific state, and the specific state being an asleep state or a deep sleep state.

In Aspect 3 of the present invention, the activity meter according to Aspect 1 of the present invention can be configured so as to further include a receiving section (communication module 140) for receiving, from a telephone (smartphone 200), incoming message information indicating that the telephone has received an incoming message, the notifying section notifying the user of the incoming message information as the specific information only during a period during which a most recent sleep level indicates that the user is not in a specific state, and the specific state being an asleep state or a deep sleep state.

In Aspect 4 of the present invention, the activity meter (activity meter 100a) according to Aspect 3 of the present invention can be configured so that in a case where a most recent sleep level at a time point at which the receiving section received the incoming message information indicates that the user is in the specific state, the notifying section (notifying section 113a) notifies the user of the incoming message information at a start of a period during which the most recent sleep level indicates that the user is not in the specific state.

According to the configuration, in a case where the telephone receives an incoming message while the user is in a deep sleep, the activity meter notifies, soon after the use wakes up (or after the sleep level has become lighter), the user of the incoming message information indicating that the telephone received the incoming message. Therefore, the activity meter further brings about such an effect as allowing the user to recognize, not much after waking up, that telephone received the incoming message.

In Aspect 5 of the present invention, the activity meter according to Aspect 3 or 4 of the present invention can be configured so that only in a case where the incoming message information indicates that the incoming message was received from a specific sender, the notifying section notifies the user that the incoming message has been received, regardless of the depth of the sleep level.

In Aspect 6 of the present invention, the activity meter (activity meter 100b) according to any one of Aspects 3 through 5 can be configured so as to further include a control section (smartphone control section 115) for controlling the telephone (smartphone 200a), in a case where an incoming message has been received, the telephone (i) transmitting, to the activity meter, incoming message information indicating that the incoming message has been received and then (ii) outputting an incoming message sound, and only in a case where a most recent sleep level at a time point at which the incoming message information has been received indicates that the user is in the deep sleep state, the control section carrying out prevention control of the telephone so as to prevent the telephone from outputting the incoming message sound.

According to the configuration, the activity meter prevents the telephone from outputting the incoming message sound in a case where the telephone has received an incoming message while the user is in a deep sleep. Therefore, the activity meter further brings about such an effect as preventing the telephone from disturbing the user in a sleep by an incoming message sound.

In Aspect 7 of the present invention, the activity meter according to Aspect 6 of the present invention can be configured so that in a case where the incoming message information indicates that the incoming message has been received from a specific sender, the control section does not carry out the prevention control of the telephone.

According to the configuration, the activity meter prevents the telephone from outputting the incoming message sound in a case where the telephone receives an incoming message from any sender other than the specific sender while the user is in a deep sleep. Meanwhile, the activity meter does not prevent the telephone from outputting the incoming message sound in a case where the telephone receives an incoming message from the specific sender while the user is in a deep sleep.

For example, in a case where the telephone receives an incoming message from an important sender (e.g., business client) while the user is in a deep sleep in a train on a business trip, the activity meter does not prevent the telephone from outputting the incoming message sound. In addition, in a case where, for example, the telephone receives an incoming message from an important sender (e.g., wife) while the user is in a deep sleep in a train on his way home from work, the activity meter does not prevent telephone from outputting the incoming message sound.

Therefore, the activity meter further brings about such an effect as preventing the user from missing a favorable opportunity or suffering damage as a result of the user failing to receive an incoming message from an important sender.

In Aspect 8 of the present invention, the activity meter according to any one of Aspects 1 through 7 can be configured so as to further include a vibration unit, the notifying section notifying the user of the specific information by vibrating the vibration unit.

In Aspect 9 of the present invention, the activity meter according to any one of Aspects 1 through 7 can be configured so as to further include a buzzer, the notifying section notifying the user of the specific information by sounding the buzzer.

In Aspect 10 of the present invention, the activity meter according to any one of Aspects 1 through 9 can be configured so as to further include a mounting fixture.

In Aspect 11 of the present invention, the activity meter according to Aspect 1 of the present invention can be configured so that the mounting fixture is a wrist band, a clip, a strap, or a neck-worn object.

In Aspect 12 of the present invention, a mobile device serves as an activity meter, the mobile device including each of the members included in the activity meter according to any one of Aspects 1 through 9.

In Aspect 12 of the present invention, the mobile device can be realized by a computer. In such a case, the scope of the present invention also encompasses (i) a program which controls the mobile device to be realized by the computer through controlling the computer to serve as each of the members included in the mobile device and (ii) a computer-readable storage medium in which the program is stored.

In Aspect 13 of the present invention, an activity amount measuring device (activity meter 1010) is an activity amount measuring device for measuring an activity amount of a user and transmitting, to a mobile device (1020), activity amount information that indicates the activity amount thus measured, the activity amount measuring device having (i) a first measuring mode in which measurement of the activity amount is carried out during a first period and (ii) a second measuring mode in which, in addition to the measurement during the first period, measurement of the activity amount is carried out during a second period which is shorter than the first period, said activity amount measuring device comprising: a receiving section (communication section 1101) for receiving, from the mobile device, a command that instructs a change in a measuring mode; and a measuring section (activity amount measuring section 1143) for measuring the activity amount, the measuring section changing the measuring mode in accordance with the command thus received by the receiving section.

According to the configuration, the activity amount measuring device changes the measuring mode in which an activity amount is changed, the measuring mode being changed in a case where the activity amount measuring device receives, from the mobile device, a command that instructs a change in measuring mode from one measuring mode to another having a differing period during which the activity amount is measured. This allows the activity amount measuring device to change, via the mobile device, a period during which to measure an activity amount. In addition, the user can change, by operating only the mobile device, a period during which the activity amount measuring device measures an activity amount. This allows the user to easily check an activity amount during a specific exercise time. In addition, since the user can easily change the period during which the activity amount measuring device measures an activity amount, it is possible to restrict excess electric power consumption of the activity amount measuring device.

In Aspect 14 of the present invention, the activity amount measuring device according to Aspect 13 of the present invention can be configured so as to further include a transmitting section (communication section 1101) for transmitting the activity amount information to the mobile device (i) after the receiving section receives a command that instructs a change in the measuring mode from the first measuring mode to the second measuring mode and (ii) each time the measuring section measures the activity amount.

According to the configuration, the activity amount measuring device transmits activity amount information to the mobile device each time an activity amount is measured. This allows the activity amount measuring device to cause a capacity of the storage section, in which activity amount information is to be recorded, to be small.

In Aspect 15 of the present invention, the activity amount measuring device according to Aspect 13 of the present invention can be configured so as to further include a transmitting section for transmitting, in a case where the receiving section receives a command that instructs a change in the measuring mode from the second measuring mode to the first measuring mode, activity amount information which indicates an activity amount measured during the second measuring mode, the activity amount information being transmitted to the mobile device.

According to the configuration, the activity amount measuring device transmits the measured activity amount information to the mobile device in a case where the activity amount measuring device has received a command that changes the measuring mode to measure an activity amount, from the second measuring mode to the first measuring mode. This allows the activity amount measuring device to collectively transmit, to the mobile device, pieces of activity amount information, and therefore allows a load of the process of the activity amount measuring device to be light.

In Aspect 16 of the present invention, the activity amount measuring device according to Aspect 13 of the present invention can be configured so as to further include a transmitting section for transmitting the activity amount information to the mobile device during a period which is longer than the second period, the transmitting section transmitting the activity amount information to the mobile device in a case where the receiving section receives a command that instructs a change in the measuring mode from the first measuring mode to the second measuring mode.

According to the configuration, the activity amount measuring device transmits measured activity amount information to the mobile device during a period which is longer than the second period, the activity amount measuring section transmitting the measured activity amount information to the mobile device in a case where the activity amount measuring device has received the command that instructs the change in the measuring mode from the first measuring mode to the second measuring mode. This allows (i) the activity amount measuring device and the mobile device to communicate with a proper frequency and (ii) a capacity of the storage section, in which the activity amount measuring device records activity amount information, to be proper.

In Aspect 17 of the present invention, the activity amount measuring device according to Aspect 13 of the present invention can be configured so as to further include: a storage section (1105) for recording the activity amount information; a storage section capacity monitoring section (storage section capacity monitoring section 1144) for judging whether or not there is an available capacity space in the storage section; and a transmitting section for transmitting the activity amount information, which is recorded in the storage section, to the mobile device in a case where the storage section capacity monitoring section has judged that there is no available capacity space in the storage section.

According to the configuration, the activity amount measuring device transmits activity amount information to the mobile device in a case where there is no available capacity space in the storage section in which to record activity amount information. This prevents the activity amount measuring device from encountering a case where, because of a lack of the capacity of the storage section, it is not possible to record, in the storage section, activity amount information which indicates an activity amount measured.

In Aspect 18 of the present invention, the activity amount measuring device according to Aspect 13 of the present invention can be configured so that the receiving section receives (i) a command that instructs a change in the measuring mode from the first measuring mode to the second measuring mode and (ii) period information that specifies a value of the second period; and in a case where the receiving section has received the command that instructs the change in the measuring mode from the first measuring mode to the second measuring mode, the measuring section sets, to a value specified by the period information, the value of the second period during which the activity amount is measured in the second measuring mode.

According to the configuration, the activity amount measuring device receives period information from the mobile device, and then measures an activity amount by use of a value of a period specified by the period information thus received. This allows the activity amount measuring device to measure an activity amount during proper periods.

In Aspect 19 of the present invention, an mobile device (1020) is an mobile device for (i) receiving, from an activity amount measuring device (activity meter 1010), activity amount information which indicates an activity amount of a user and (ii) presenting, to the user, the activity amount indicated by the activity amount information thus received, the activity amount measuring device having (i) a first measuring mode in which measurement of the activity amount is carried out during a first period and (ii) a second measuring mode in which, in addition to the measurement during the first period, measurement of the activity amount is carried out during a second period which is shorter than the first period, said mobile device comprising: a transmitting section (communication section 1201) for transmitting, in a case where a predetermined user operation has been detected, a command to the activity amount measuring device, a command that instructs a change in a measuring mode in which the activity amount measuring device measures the activity amount, the command being transmitted to the activity amount measuring device.

According to the configuration, in a case where the mobile device has detected a user operation to change in measuring mode to a measuring mode having differing periods during which the activity amount measuring device measures an activity amount, the mobile device transmits, to the activity amount measuring device, a command that instructs a change in the measuring mode in which the activity amount measuring device measures an activity amount. This allows the mobile device to change a period during which the activity amount measuring device measures an activity amount. In addition, a user can change the period by operating only the mobile device. This allows the user to easily check an activity amount of a specific exercise. In addition, since it is possible to easily change the period, it is possible to restrict excess electric power consumption of the activity amount measuring device.

In Aspect 20 of the present invention, the mobile device according to Aspect 19 of the present invention can be configured so that the mobile device receives the activity amount information from the activity amount measuring device in a case where the mobile device has transmitted a command to instruct a change in the measuring mode from the second measuring mode to the first measuring mode.

According to the configuration, the mobile device receives activity amount information from the activity amount measuring device in a case where the mobile device has transmitted a command to instruct a change in the measuring mode in which the activity amount measuring device measures an activity amount, from the second measuring mode to the first measuring mode. This allows the mobile device to collectively receives, from the activity amount measuring device, activity amount information indicative of pieces of activity amounts measured by the activity amount measuring device. Therefore a load the process of the mobile device becomes light.

In Aspect 21 of the present invention, the mobile device according to Aspect 19 of the present invention can be configured so that in a case where the transmitting section has transmitted a command that instructs a change in the measuring mode from the first measuring mode to the second measuring mode, the mobile device receives the activity amount information during a period longer than the second period.

According to the configuration, in a case where a command to change the measuring mode in which the activity amount measuring device measures an activity amount has been transmitted, the mobile device receives activity amount information during a period longer than a period during which an activity amount is measured. This allows the mobile device to receive activity amount information with a proper frequency.

In Aspect 22 of the present invention, the mobile device according to Aspect 19 of the present invention can be configured so that the transmitting section transmits (i) a command that instructs a change in the measuring mode from the first measuring mode to the second measuring mode and (ii) period information that specifies a value of the second period.

According to the configuration, the mobile device transmits, to the activity amount measuring device, period information that specifies a value of the second period. Therefore, the mobile device can allow the activity amount measuring device to measure an activity amount during a proper period.

In Aspect 23 of the present invention, the activity amount measuring system (1001) includes (i) the activity amount measuring device according to any one of Aspects 13 through 18 and (ii) the mobile device according to any one of Aspects 19 through 22.

With the configuration, it is possible to realize an activity amount measuring system that includes (i) an activity amount measuring device according to any one of Aspects 13 through 18 and (ii) a mobile device according to any one of Aspects 19 through 22.

The activity amount measuring devices according to each aspect of the present invention and the mobile devices according to any one of Aspects 19 through 22 can each be realized by a computer. In such a case, the scope of the present invention also encompasses (i) a control program for the activity amount measuring device, which program controls a computer to serve as the foregoing sections of the activity amount measuring device so that the activity amount measuring device can be realized by the computer, (ii) a control program for the mobile device, which program controls a computer to serve as the foregoing sections of the mobile device so that the mobile device can be realized by the computer, (iii) a computer-readable storage medium in which the control program for the activity amount measuring device is stored, and (iv) a computer-readable storage medium in which the control program for the mobile device is stored.

In Aspect 24 of the present invention, the activity amount measuring device (activity meter 1010) is an activity amount measuring device for measuring an activity amount of a user and transmitting, to a mobile device (1020), activity amount information indicative of the activity amount thus measured, said activity amount measuring device including: a receiving section (communication section 1101) for receiving, from the mobile device, a command that instructs a change in period during which the activity amount is measured; and a measuring section (activity amount measuring section 1143) for measuring the activity amount, the measuring section changing the period in a case where the receiving section has received the command.

According to the configuration, in a case where the activity amount measuring device has received the command from the mobile device, the activity amount measuring device changes the period during which an activity amount is measured. This allows the activity amount measuring device to change, via the mobile device, a period during which to measure an activity amount. In addition, the user can change, by operating only the mobile device, a period during which the activity amount measuring device measures an activity amount. This allows the user to easily check an activity amount during a specific exercise. In addition, since the user can easily change the period during which the activity amount measuring device measures an activity amount, it is possible to restrict excess electric power consumption of the activity amount measuring device.

In Aspect 25 of the present invention, an information sharing support device is an information sharing support device (server 2030) including: an obtaining section (communication section 2301) for obtaining, from a first mobile device (mobile device 2020A or mobile device 2020B), first activity amount information which indicates an activity amount measured by a first activity amount measuring device (activity meter 2010A or activity meter 2010B) that measures an activity amount of a first user, the first mobile device communicating with the first activity amount measuring device via short-distance wireless communication; a generating section (notification control section 2322) for generating a reporting instruction which (i) instructs reporting in accordance with the first activity amount information and (ii) instructs reporting by a second activity amount measuring device (activity meter 2010B or activity meter 2010A) that measures an activity amount of a second user who is different from the first user; and a transmitting section (communication section 2301) for transmitting the reporting instruction to a second mobile device (mobile device 2020B or mobile device 2020A) which communicates with the second activity amount measuring device via short-distance wireless communication.

According to the configuration, the information sharing support device transmits, to the second activity amount measuring device via the second mobile device, a reporting instruction that indicates reporting in accordance with the first activity amount information which has been obtained from the first activity amount measuring device via the first mobile device. This allows the second activity amount measuring device to carry out, in accordance with the reporting instruction transmitted from the information sharing support device, reporting according to the first activity amount information.

Therefore, the information sharing support device can allow the first and second activity amount measuring devices to easily share the first activity amount information without causing the first and second users to operate any devices (first and second mobile devices and first and second activity amount measuring devices). In other words, the users can share the first activity amount information without operating any devices.

In Aspect 26 of the present invention, the information sharing support device according to Aspect 25 of the present invention can be configured to further include a reporting ability judging section (sharing control section 2321) for judging whether or not the reporting by the second activity amount measuring device is possible, the transmitting section transmitting the reporting instruction in a case where the reporting ability judging section judges that the reporting by the second activity amount measuring device is possible.

According to the configuration, in a case where it is judged that reporting by the second activity amount measuring device, the information sharing support device transmits the reporting instruction, whereas in a case where it is judged that the reporting by the second activity amount measuring device is not possible, the information sharing support device does not transmit the reporting instruction.

Therefore, the information sharing support device can be prevented from transmitting the notification instruction even in a case where the reporting by the second activity amount measuring device is not possible. This allows an increase in convenience of the user.

In Aspect 27 of the present invention, the information sharing support device according to Aspect 26 of the present invention can be configured so as to further include a storage section (schedule information management region 2333) for storing schedule management information which manages a schedule of the first user and a schedule of the second user, in a case where (i) an event, which is among events registered in the schedule of the first user and which is held at a time point at which the first activity amount information is obtained, is specified and (ii) the event thus specified is registered in the schedule of the second user, the reporting ability judging section judging that the reporting by the second activity amount measuring device is possible.

According to the configuration, even in a case where the same event is registered in schedule information of the first user and in schedule information of the second user, the information sharing support device transmits the reporting instruction if the same event is held at the time point at which the first activity amount information is obtained.

Therefore, in a case where the first user and the second user are participating in the same event at the time point at which the first activity amount information is obtained, the information sharing support device can allow the first activity amount measuring device and the second activity amount measuring device to share the first activity amount information.

In Aspect 28 of the present invention, the information sharing support device according to Aspect 26 of the present invention can be configured so as to further include a storage section (schedule information management region 2333) for storing schedule management information which manages a schedule of the first user and a schedule of the second user, in a case where the time point at which the first activity amount information is obtained falls, as a time period during which the second user cannot check reporting, within a time period which is preregistered in the schedule of the second user, the reporting ability judging section judging that the reporting by the second activity amount measuring device is impossible.

According to the configuration, in a case where the time point at which the first activity information is obtained falls within the time period during which the second user cannot check reporting, the information sharing support device does not transmit the reporting instruction.

Therefore, the information sharing support device can prevent a case where the reporting instruction is transmitted and therefore the second activity amount measuring device carries out reporting even during the time period during which the second user cannot check reporting. Note that examples of the time period during which is preregistered by the second user in the schedule of the second user and during which the second user cannot check reporting encompass (i) a time period during which the second user plans to sleep and (ii) a time period during which the second user plans to be travelling by car.

In Aspect 29 of the present invention, the information sharing support device according to Aspect 26 of the present invention can be configured so as to further include: an activity status judging section (sharing control section 2321) for judging an activity status of the second user according to second activity amount information which has been measured by the second activity amount measuring device and which indicates an activity amount of the second user, in a case where a judgment result of the judging by the activity status judging section at the time point at which the first activity amount information is obtained is a predetermined judgment result, the reporting ability judging section judging that reporting by the second activity amount measuring device is impossible.

According to the configuration, the information sharing support device does not transmit the reporting instruction in a case where the judgment result of the judging by the activity status judging section at the time point at which the first activity information is obtained is a predetermined judgment result. Note that the predetermined judgment result is more specifically a judgment result which indicates that the second user cannot check reporting. Examples of the predetermined judgment result encompass a judgment result which indicates that the second user is in an asleep state.

Therefore, the information sharing support device can prevent a case where the reporting instruction is transmitted and therefore the second activity amount measuring device carries out reporting even in a case where the second user cannot check reporting. For example, it is possible to prevent a case where the second activity amount measuring device carries out reporting so as to wake up the second user even in a case where the second user is in an asleep state.

In Aspect 30 of the present invention, an activity amount measuring device (activity meter 2010) can be configured so as to further include: a receiving section (communication section 2103) for obtaining activity amount information which indicates an activity amount of another user, the activity amount of the another user being measured by another activity amount measuring device other than the activity amount measuring device, the receiving section receiving the activity amount information from an information sharing support device (server 2030) via a mobile device (mobile device 2020) which communicates with the activity amount measuring device via short-distance wireless communication; and a reporting section for reporting in accordance with the activity amount information thus obtained by the receiving section.

According to the configuration, the activity amount measuring device (i) obtains activity amount information from the information sharing support device via the second mobile device, the activity amount information indicating an activity amount of another user which activity amount having been measured by the another activity amount measuring device and (ii) carries out reporting in accordance with the activity amount information thus obtained.

Therefore, the activity amount measuring device can allow the activity amount measuring device and the another activity amount measuring device to easily share the activity amount information without causing the user to operate any devices (the mobile device and the activity amount measuring device). In other words, the activity amount measuring device and the another activity amount measuring device can share the activity amount information without user operating any devices.

In Aspect 31 of the present invention, an information sharing system (information sharing system 2001) includes: a first activity amount measuring device (activity meter 2010A or activity meter 2010B) for measuring an activity amount of a first user; a second activity amount measuring device (activity meter 2010B or activity meter 2010A) for measuring an activity amount of a second user; a first mobile device (mobile device 2020A or mobile device 2020B) for communicating with the first activity amount measuring device via short-distance wireless communication; a second mobile device (mobile device 2020B or mobile device 2020A) for communicating with the second activity amount measuring device via short-distance wireless communication; and an information sharing support device (server 2030) for communicating with the first mobile device and with the second mobile device, the information sharing support device transmitting a reporting instruction to the second activity amount measuring device via the second mobile device, the reporting instruction being an instruction which (i) instructs reporting in accordance with activity amount information indicative of the activity amount of the first user, the activity amount information having been transmitted from the first activity amount measuring device via the first mobile device and (ii) instructs reporting by the second activity amount measuring device, and the second activity amount measuring device reporting in accordance with the reporting instruction.

According to the configuration, the information sharing support device transmits reporting instruction to the second activity amount measuring device via the second mobile device, which reporting instruction instructs reporting according to the activity amount information obtained from the first activity amount measuring device via the first mobile device. Then, the second activity amount measuring device carries out reporting according to the activity amount information in accordance with the reporting instruction transmitted from the information sharing support device.

Therefore, the information sharing support device can allow the first and second activity amount measuring devices to easily share the activity amount information without causing the first and second users to operate any devices (the first and second mobile devices and the first and second activity amount measuring devices). In other words, the users can share the activity amount information without operating any devices.

In Aspect 32 of the present invention, an information sharing support method is a method of supporting sharing information of information sharing support device (server 2030), the method including the steps of: obtaining, from a first mobile device (mobile device 2020A or mobile device 2020B), first activity amount information which indicates an activity amount measured by a first activity amount measuring device (activity meter 2010A or activity meter 2010B) that measures an activity amount of a first user, the first mobile device communicating with the first activity amount measuring device via short-distance wireless communication; generating a reporting instruction which (i) instructs reporting in accordance with the first activity amount information and (ii) instructs reporting by a second activity amount measuring device (activity meter 2010B or activity meter 2010A) that measures an activity amount of a second user who is different from the first user; and transmitting the reporting instruction to a second mobile device (mobile device 2020B or mobile device 2020A) which communicates with the second activity amount measuring device via short-distance wireless communication.

The information sharing support device according to each of the aspects of the present invention can be realized by use of a computer. In such a case, the scope of the present invention also encompasses (i) a program for the information sharing support device, which program controls a computer to serve as the foregoing sections of the information sharing support device so that the information sharing support device can be realized by the computer and (ii) a computer-readable storage medium in which the record is stored.

In Aspect 33 of the present invention, an activity support device (server 3030) includes: a providing section (activity amount extracting section 3323) for providing, in a case where a target user carries out predetermined exercise, a mobile device (mobile device 3020B) of the target user with target user activity amount information indicative of a target user activity amount corresponding to the predetermined exercise; and an obtaining section (activity amount managing section 3322) for obtaining another user activity amount information indicative of an another user activity amount of the predetermined exercise carried out by another user, the obtaining section obtaining the another user activity amount information from another mobile device (mobile device 3020A) which corresponds to an activity amount measuring device (activity meter 3010) that measures the another user activity amount of the another user, the providing section providing, as the target user activity amount information, the another user activity amount information which has been obtained by the obtaining section.

According to the configuration, in a case where the target user carries out the predetermined exercise, the activity support device can provide the mobile device of the user with, as activity amount information indicative of the activity amount of the target user, activity amount information indicative of the activity amount of the predetermined exercise carried out by the another user. In other words, in a case where the target user carries out the predetermined exercise, the activity support device can provide the target user with, instead of an activity amount automatically calculated by use of generally defined parameters, activity amount information which indicates the activity amount measured in a case where the another user has actually carried out the predetermined exercise.

Therefore, the activity support device can provide, to the mobile device of the target user who does not possess an activity amount measuring device, activity amount information which indicates an accurate activity amount corresponding to the actual activity amount obtained in a case where the predetermined exercise has been carried out.

Note that in this specification, "mobile device corresponding an activity amount measuring device" refers to, for example, a mobile device (mobile device 3020A) capable of communicating with the activity amount measuring device (activity meter 3010) via short-distance wireless communication.

In Aspect 34 of the present invention, the activity support device according to Aspect 33 of the present invention can be configured so that the obtaining section obtains plural user activity amount information indicative of a plural user activity amount of the predetermined exercise carried out by each of a plurality of users, the obtaining section obtaining the plural user activity amount information from a yet another mobile device which corresponds to an activity amount measuring device that measures the plural user activity amount of the each of the plurality of users, said activity support device further including: a recording section (activity amount managing section 3322) for recording the plural user activity amount information in a storage section (storage section 3303) such that the plural user activity amount information is associated with user attribute information (user information) indicative of an attribute of the each of the plurality of users, the providing section providing, as the target user activity amount information, activity amount information which is among pieces of plural user activity amount information recorded in the storage section and which is associated with user attribute information indicative of an attribute similar to an attribute of the target user.

According to the configuration, the activity support device obtains, from each of the mobile devices of the respective plurality of users, (i) activity amount information and (ii) user attribute information indicative of an attribute of the user. Then, the activity support device records, in the storage section, the activity amount information and the user attribute information so as to be associated with each other. Then, the activity support device provides, with the mobile device, activity amount information which is among pieces of activity amount information recorded in the storage section and which is associated with the user attribute information indicative of an attribute similar to an attribute of the target user, the activity support device providing the activity amount information with the mobile device as activity amount information which indicates an activity amount of the target user.

Therefore, the activity support device can provide, to the mobile device of the target user who does not possess an activity amount measuring device, activity amount information which indicates an actual activity amount obtained in a case where the predetermined exercise is carried out by another user having an attribute similar to the attribute of the target user. This allows the activity support device to provide, in a case where the predetermined exercise is to be carried out, a more accurate activity amount for the mobile device of the user who does not possess an activity amount measuring device.

Note that examples of the user attribute information encompass a height, a weight, an age, a gender and a stride of a user.

In Aspect 35 of the present invention, the activity support device according to Aspect 33 of the present invention can be configured so as to further include: an environment information obtaining section (activity amount managing section 3322) for obtaining, in a case where each of a plurality of users has carried out the predetermined exercise, environment information indicative of an environment surrounding the each of the plurality of users; and a recording section (activity amount managing section 3322) for recording plural user activity amount information indicative of a plural user activity amount of the predetermined exercise carried out by the each of the plurality of users, the recording section recording the plural user activity amount information in a storage section (storage section 3303) such that the plural user activity amount information is associated with the environment information which has been obtained by the environment information obtaining section, the providing section providing, as the target user activity amount information, activity amount information which is among pieces of plural user activity amount information recorded in the storage section and which is associated with environment information indicative of an environment similar to an environment surrounding the target user.

According to the configuration, the activity support device can provide, to the mobile device of the target user who does not possess an activity amount measuring device, activity amount information which indicates an activity amount corresponding to an activity amount of the predetermined exercise carried out in an environment similar to a surrounding environment in a case where the target user carries out the predetermined exercise. This allows the activity support device to provide, in a case where the predetermined exercise is to be carried out, a more accurate activity amount for the mobile device of the target user who does not possess an activity amount measuring device.

Note that examples of the environment information encompass weather, climate and humidity.

In Aspect 36 of the present invention, the activity support device can be configured so that: the predetermined exercise according to each of Aspects 33 through 35 is a movement made along a predetermined route; the obtaining section obtains activity amount information which indicates an activity amount of a movement made by the another user along the predetermined route; and the providing section provides, as activity amount information which indicates an activity amount according to a movement made by the target user along the predetermined route, the activity amount information thus obtained by the obtaining section.

According to the configuration, in a case where the target user makes a movement along the predetermined route, the activity support device can provide, to the mobile device, the another activity amount information which indicates an activity amount of a movement made by the another user along the predetermined route, the activity support device providing the another activity amount information as activity amount information which indicates an activity amount of the target user.

Note that examples of a movement along the predetermined route encompass walking, jogging and cycling.

In Aspect 37 of the present invention, the activity support device can be configured so that: the obtaining section according to any one of Aspects 34 through 36 obtains activity amount information which indicates an activity amount of a movement made by the another user to each of a plurality of midway points on the predetermined route; and the providing section provides, as activity amount information which indicates an activity amount of a movement made by the target user to the each of the plurality of midway points, activity amount information which (i) has been obtained by the obtaining section and (ii) indicates the activity amount of the movement made by the another user to the each of the plurality of midway points.

In Aspect 38 of the present invention, the activity support device can be configured so that the providing section according to any one of Aspects 34 through 36 (i) calculates, by use of an activity amount of a movement made by the another user to an ending point of the predetermined route, an activity amount of a movement made by the another user to a midway point of the predetermined route and (ii) provides, as activity amount information which indicates an activity amount of a movement made by the target user to the midway point of the predetermined route, activity amount information which indicates the activity amount thus calculated.

According to the configuration, even while the user is at a halfway point during a movement along the predetermined route, the activity support device can provide the mobile device with activity amount information which indicates an activity amount of a movement made by the user to a midway point which is the halfway point.

In Aspect 39 of the present invention, a mobile device (mobile device 3020B) includes: a presenting section (display section 3206) for presenting, in a case where a target user carries out predetermined exercise, a target user activity amount corresponding to the predetermined exercise; and a receiving section (communication section 3201) for receiving another user activity amount information indicative of another user activity amount of the predetermined exercise carried out by another user, the receiving section receiving the another user activity amount information from another mobile device (mobile device 3020A) via an activity support device (server 3030), which another mobile device corresponds to an activity amount measuring device (activity meter 3010) that measures the another user activity amount of the another user, the presenting section presenting, as the target user activity amount information, an activity amount indicated by the another user activity amount information which has been received by the receiving section.

According to the configuration, in a case where the target user carries out the predetermined exercise, the mobile device can provide, as an activity amount of the target use, an activity amount which has been measured by the activity amount measuring device in a case where the another user has carried out the predetermined exercise.

Therefore, the mobile device can provide, to the target user who does not possess an activity amount measuring device, accurate activity amount corresponding to an actual activity amount obtained in a case where the target user has carried out the predetermined exercise.

In Aspect 40 of the present invention, an activity support system (activity support system 3001) includes: a mobile device (mobile device 3020B) for presenting, in a case where a target user carries out predetermined exercise, a target user activity amount corresponding to the predetermined exercise; another mobile device (mobile device 3020A) corresponding to an activity amount measuring device (activity meter 3010) that measures another user activity amount of another user; and an activity support device (server 3030) for communicating with the mobile device and with the another mobile device, the activity support device transmitting, to the mobile device, another user activity amount information which has been obtained from the another mobile device and which indicates another user activity amount of the predetermined exercise carried out by the another user, and the mobile device presenting, as the target user activity amount information, the another user activity amount indicated by the another user activity amount information transmitted from the activity support device.

According to the configuration, the activity support system can provide, in a case where the target user carries out the predetermined exercise, activity amount information which has been obtained by the activity support device and which indicates an activity amount of the predetermined exercise carried out by the another user.

Therefore, the activity support system can present, to the target user who does not possess an activity amount measuring device, an accurate activity amount corresponding to an actual activity amount obtained in a case where the predetermined exercise has been carried out.

In Aspect 41 of the present invention, a method of providing an activity amount of an activity support device is a method in which the activity support device provides, in a case where a target user carries out predetermined exercise, a mobile device of the target user with target user activity amount information indicative of a target user activity amount corresponding to the predetermined exercise, the method including the steps of: (a) obtaining another user activity amount information indicative of an another user activity amount of the predetermined exercise carried out by another user, the another user activity amount information being obtained from another mobile device which corresponds to an activity amount measuring device that measures the another user activity amount of the another user; and (b) providing, as the target user activity amount information, the another user activity amount information which has been obtained in the step (a).

In each of the aspects of the present invention, the information sharing support device can be realized by a computer. In such a case, the scope of the present invention also encompasses (i) a program for the information sharing support device which program controls the information sharing support device to be realized by the computer through controlling the computer to serve as each of the members included in the information sharing support device and (ii) a computer-readable storage medium in which the program is stored.

The present invention is not limited to the embodiments, but can be altered by a skilled person in the art within the scope of the claims. An embodiment derived from a proper combination of technical means each disclosed in a different embodiment is also encompassed in the technical scope of the present invention. Further, it is possible to form a new technical feature by combining the technical means disclosed in the respective embodiments.

INDUSTRIAL APPLICABILITY

The present invention can be suitably used for an activity meter.

The present invention can also be suitably used for, but are not limited to, (i) activity amount measuring devices for measuring activity amounts of users and (ii) mobile devices for operating activity amount measuring devices.

The information sharing support device of the present invention can be suitably used for, but are not limited to, (i) mobile devices such as smartphones, mobile phones, PDAs, and tablet PCs and (ii) servers for integrally managing activity meters.

The activity support device of the present invention can be suitably used for, but are not limited to, (i) mobile devices such as smartphones, mobile phones, PDAs, and tablet PCs and (ii) servers for integrally managing activity meters.

REFERENCE SIGNS LIST

100, 100*a*, 100*b* Activity meter
110 CPU
111 Activity amount measurement section
112 Sleep level judging section (judging section)
113, 113*a* Notifying section (receiving section)
114 Setting information obtaining section
115 Smartphone control section (control section)
140 Communication module (receiving section)
200, 200*a* Smartphone (telephone)
1001 Activity amount measuring system
1010 Activity meter (activity amount measuring device)
1020 Mobile device
1101 Communication section (receiving section, transmitting section)
1102 Timekeeping section
1103 Sensor section
1104 Control section
1105 Storage section
1141 Measuring mode control section
1142 Transfer data generating section
1143 Activity amount measuring section (measuring section)
1144 Storage section capacity monitoring section
1145 Sensor output analyzing section
1201 Communication section (transmitting section)
1202 Operation section
1203 Display section
1204 Control section
1241 Display control section
1242 Measuring mode instructing section (detecting section)
2001 Information sharing system
2010 Activity meter (activity amount measuring device)
2020 Mobile device
2030 Server (information sharing support device)
2101 Sensor section
2102 Timekeeping section
2103 Communication section (receiving section)
2104 Control section
2105 Storage section
2106 Reporting section
2141 Activity amount calculating section
2142 Report control section
2201 Communication section 2202 Assisting information obtaining section
2203 Control section
2204 Operation section
2205 Storage section
2301 Communication section (obtaining section, transmitting section)
2302 Control section
2303 Management information storage section
2321 Sharing control section (reporting ability judging section, activity status judging section)
2322 Notification control section (notification control section)
2331 User registration information management region
2332 Friend registration information management region
2333 Schedule information management region (storage section)
3001 Activity support system
3010 Activity meter (activity amount measuring device)
3020 Mobile device
3030 Server (activity support device)
3101 Sensor section
3102 Timekeeping section
3103 Communication section
3104 Control section
3105 Storage section
3141 Sensor output analyzing section
3142 Activity amount measuring section
3143 Transfer data generating section
3201 Communication section (receiving section)
3202 Assisting information obtaining section
3203 Control section
3204 Operation section
3205 Storage section
3206 Display section (presenting section)
3301 Communication section
3302 Control section
3303 Storage section
3321 Route generating section
3322 Activity amount managing section (obtaining section, recording section, environment information obtaining section)
3323 Activity amount extracting section (providing section)

The invention claimed is:

1. An activity amount measuring device that measures an activity amount of a user and transmits, to a mobile device, activity amount information that indicates the activity amount thus measured, the activity amount measuring device having (i) a first measuring mode in which measurement of the activity amount is carried out at a first interval and (ii) a second measuring mode in which, in addition to the measurement at the first interval, measurement of the activity amount is carried out at a second interval which is shorter than the first interval, said activity amount measuring device comprising:
   a receiving section that receives, from the mobile device, a command that instructs a change in a measuring mode;
   a measuring section that measures the activity amount, the measuring section changing the measuring mode in accordance with the command thus received by the receiving section; and
   a communication section that transmits, in the second measuring mode, the activity amount to the mobile device at a third interval that is longer than the second interval.

2. The activity amount measuring device as set forth in claim 1, wherein:
   the receiving section receives (i) a command that instructs a change in the measuring mode from the first measuring mode to the second measuring mode and (ii) interval information that specifies a value of the second interval; and
   in a case where the receiving section has received the command that instructs the change in the measuring mode from the first measuring mode to the second measuring mode, the measuring section sets, to a value specified by the interval information, the value of the second interval during which the activity amount is measured in the second measuring mode.

3. A mobile device that (i) receives, from an activity amount measuring device, activity amount information which indicates an activity amount of a user and (ii) presents, to the user, the activity amount indicated by the activity amount information thus received,
   the activity amount measuring device having (i) a first measuring mode in which measurement of the activity amount is carried out at a first interval and (ii) a second measuring mode in which, in addition to the measurement at the first interval, measurement of the activity amount is carried out at a second interval which is shorter than the first interval, in the second measuring mode, the activity amount measuring device transmitting the activity amount to the mobile device at a third interval that is longer than the second interval,
   said mobile device comprising:
   a transmitting section that transmits, in a case where a predetermined user operation has been detected, a command that instructs a change in a measuring mode in which the activity amount measuring device measures the activity amount, to the activity amount measuring device.

* * * * *